United States Patent
Liu et al.

(10) Patent No.: US 11,624,130 B2
(45) Date of Patent: Apr. 11, 2023

(54) CONTINUOUS EVOLUTION FOR STABILIZED PROTEINS

(71) Applicant: President and Fellows of Harvard College, Cambridge, MA (US)

(72) Inventors: David R. Liu, Cambridge, MA (US); Ahmed Hussein Badran, Cambridge, MA (US); Tina Wang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 403 days.

(21) Appl. No.: 16/648,162

(22) PCT Filed: Sep. 18, 2018

(86) PCT No.: PCT/US2018/051557
§ 371 (c)(1),
(2) Date: Mar. 17, 2020

(87) PCT Pub. No.: WO2019/056002
PCT Pub. Date: Mar. 21, 2019

(65) Prior Publication Data
US 2020/0216833 A1     Jul. 9, 2020

Related U.S. Application Data

(60) Provisional application No. 62/559,919, filed on Sep. 18, 2017.

(51) Int. Cl.
*C40B 30/04*     (2006.01)
*C12N 15/10*     (2006.01)
(Continued)

(52) U.S. Cl.
CPC .......... *C40B 30/04* (2013.01); *C12N 15/1055* (2013.01); *C12N 15/1058* (2013.01); *C12N 15/111* (2013.01); *C12N 15/70* (2013.01)

(58) Field of Classification Search
None
See application file for complete search history.

(56) References Cited

U.S. PATENT DOCUMENTS

| 5,057,432 A | 10/1991 | Wangersky et al. |
| 5,223,409 A | 6/1993 | Ladner et al. |

(Continued)

FOREIGN PATENT DOCUMENTS

| EP | 0289479 A2 | 11/1988 |
| EP | 3115457 A1 | 1/2017 |

(Continued)

OTHER PUBLICATIONS

Extended European Search Report, dated Mar. 30, 2012, in connection with Application No. EP 09812363.

(Continued)

*Primary Examiner* — Christian C Boesen
(74) *Attorney, Agent, or Firm* — Wolf, Greenfield & Sacks, P.C.

(57) ABSTRACT

Some aspects of this disclosure relate to systems, apparatuses, compositions (e.g., isolated nucleic acids and vectors), and methods for improving the stability and/or solubility of proteins evolved using phage-assisted continuous evolution (PACE). In some embodiments, vectors described herein comprise nucleic acids encoding selection systems (e.g., positive and/or negative selection systems) that link expression of genes required for production of infectious phage particles to a desirable physiochemical (e.g., stability or solubility) and/or desired function of an evolved protein.

20 Claims, 34 Drawing Sheets
Specification includes a Sequence Listing.

(51) Int. Cl.
C12N 15/11 (2006.01)
C12N 15/70 (2006.01)

(56) References Cited

U.S. PATENT DOCUMENTS

| | | | |
|---|---|---|---|
| 5,658,727 A | 8/1997 | Barbas et al. |
| 5,712,089 A | 1/1998 | Borrebaeck et al. |
| 5,821,047 A | 10/1998 | Garrard et al. |
| 5,880,275 A | 3/1999 | Fischhoff et al. |
| 5,965,124 A | 10/1999 | Feinberg et al. |
| 6,033,874 A | 3/2000 | Baum et al. |
| 6,156,509 A | 12/2000 | Schellenberger |
| 6,429,298 B1 | 8/2002 | Ellington et al. |
| 6,713,063 B1 | 3/2004 | Malvar et al. |
| 6,962,705 B2 | 11/2005 | Malvar et al. |
| 6,969,731 B1 | 11/2005 | Tang et al. |
| 7,064,249 B2 | 6/2006 | Corbin et al. |
| 7,070,982 B2 | 7/2006 | Malvar et al. |
| 9,023,594 B2 | 5/2015 | Liu et al. |
| 9,228,207 B2 | 1/2016 | Liu et al. |
| 9,267,127 B2 | 2/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,394,537 B2 | 7/2016 | Liu et al. |
| 9,526,784 B2 | 12/2016 | Liu et al. |
| 9,567,589 B2 | 2/2017 | Jin et al. |
| 9,737,604 B2 | 8/2017 | Jin et al. |
| 9,766,216 B2 | 9/2017 | Wada et al. |
| 9,771,574 B2 | 9/2017 | Liu et al. |
| 10,179,911 B2 | 1/2019 | Liu et al. |
| 10,227,581 B2 | 3/2019 | Liu et al. |
| 10,336,997 B2 | 7/2019 | Liu et al. |
| 10,392,674 B2 | 8/2019 | Liu et al. |
| 10,597,679 B2 | 3/2020 | Liu et al. |
| 10,612,011 B2 | 4/2020 | Liu et al. |
| 10,682,410 B2 | 6/2020 | Liu et al. |
| 10,920,208 B2 | 2/2021 | Liu et al. |
| 11,046,948 B2 | 6/2021 | Liu et al. |
| 11,078,469 B2 | 8/2021 | Liu et al. |
| 11,104,967 B2 | 8/2021 | Liu et al. |
| 11,214,792 B2 | 1/2022 | Liu et al. |
| 11,299,729 B2 | 4/2022 | Badran et al. |
| 2002/0132327 A1 | 9/2002 | Hay et al. |
| 2003/0119764 A1 | 6/2003 | Loeb et al. |
| 2003/0167533 A1 | 9/2003 | Yadav et al. |
| 2003/0186292 A1* | 10/2003 | MacNeil ............... C12N 15/11 506/10 |
| 2003/0203480 A1 | 10/2003 | Kovesdi et al. |
| 2005/0019753 A1 | 1/2005 | Kukolj et al. |
| 2005/0100973 A1 | 5/2005 | Steward et al. |
| 2006/0112447 A1 | 5/2006 | Bogdanova et al. |
| 2006/0160222 A1 | 7/2006 | Rozwadowski et al. |
| 2006/0166319 A1 | 7/2006 | Chan et al. |
| 2008/0220502 A1 | 9/2008 | Schellenberger et al. |
| 2009/0215110 A1 | 8/2009 | Gibson et al. |
| 2009/0227463 A1 | 9/2009 | Reif et al. |
| 2009/0300777 A1 | 12/2009 | Nakayama |
| 2010/0297180 A1 | 11/2010 | Shone |
| 2011/0177495 A1 | 7/2011 | Liu et al. |
| 2011/0318385 A1 | 12/2011 | Jackson et al. |
| 2012/0128649 A1 | 5/2012 | Chaddock et al. |
| 2012/0190825 A1 | 7/2012 | Neumann et al. |
| 2013/0059931 A1 | 3/2013 | Petersen-Mahrt et al. |
| 2013/0117869 A1 | 5/2013 | Duchateau et al. |
| 2013/0345064 A1 | 12/2013 | Liu et al. |
| 2013/0345065 A1 | 12/2013 | Liu et al. |
| 2014/0201858 A1 | 7/2014 | Ostertag et al. |
| 2015/0056177 A1 | 2/2015 | Liu et al. |
| 2015/0259721 A1 | 9/2015 | Van Brunt et al. |
| 2015/0275202 A1 | 10/2015 | Liu et al. |
| 2016/0002301 A1 | 1/2016 | Je et al. |
| 2016/0201040 A1 | 7/2016 | Liu et al. |
| 2016/0348096 A1 | 12/2016 | Liu et al. |
| 2017/0009224 A1 | 1/2017 | Liu et al. |
| 2017/0029844 A1 | 2/2017 | Ball et al. |
| 2017/0044520 A1 | 2/2017 | Liu et al. |
| 2017/0233708 A1 | 8/2017 | Liu et al. |
| 2018/0057545 A9 | 3/2018 | Liu et al. |
| 2018/0087046 A1 | 3/2018 | Liu et al. |
| 2018/0237758 A1 | 8/2018 | Liu et al. |
| 2019/0219575 A1 | 7/2019 | Gray et al. |
| 2019/0256842 A1 | 8/2019 | Liu et al. |
| 2019/0276816 A1 | 9/2019 | Liu et al. |
| 2019/0276873 A1 | 9/2019 | Dong et al. |
| 2020/0071722 A1 | 3/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2021/0163924 A1 | 6/2021 | Packer et al. |
| 2021/0238569 A1 | 8/2021 | Liu et al. |
| 2021/0261938 A1 | 8/2021 | Liu et al. |
| 2021/0403887 A1 | 12/2021 | Liu et al. |
| 2022/0073887 A1 | 3/2022 | Liu et al. |
| 2022/0154237 A1 | 5/2022 | Liu et al. |
| 2022/0195418 A1 | 6/2022 | Liu et al. |

FOREIGN PATENT DOCUMENTS

| | | |
|---|---|---|
| JP | H0937764 A | 2/1997 |
| JP | 2011-081011 | 4/2011 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 94/18316 A2 | 8/1994 |
| WO | WO 96/04403 A1 | 2/1996 |
| WO | WO 98/32845 A1 | 7/1998 |
| WO | WO 00/71694 A1 | 11/2000 |
| WO | WO 01/05950 A2 | 1/2001 |
| WO | WO 01/61049 A1 | 8/2001 |
| WO | WO 2005/081632 A2 | 9/2005 |
| WO | WO 2007/066923 A1 | 6/2007 |
| WO | WO 2008/005529 A2 | 1/2008 |
| WO | WO 2009/082488 A2 | 7/2009 |
| WO | WO 2009/108180 A2 | 9/2009 |
| WO | WO 2010/028347 A2 | 3/2010 |
| WO | WO 2011/039518 A2 | 4/2011 |
| WO | WO 2011/147590 A2 | 12/2011 |
| WO | WO 2011/066747 A1 | 6/2012 |
| WO | WO 2012/088381 A2 | 6/2012 |
| WO | WO 2012/138927 A2 | 10/2012 |
| WO | WO 2013/047844 A1 | 4/2013 |
| WO | WO 2014/039585 A2 | 3/2014 |
| WO | WO 2014/157820 A1 | 10/2014 |
| WO | WO 2014/158593 A1 | 10/2014 |
| WO | WO 2015/134121 A2 | 9/2015 |
| WO | WO 2015/193897 A1 | 12/2015 |
| WO | WO 2016/077052 A9 | 5/2016 |
| WO | WO 2016/168631 A1 | 10/2016 |
| WO | WO 2017/015559 A2 | 1/2017 |
| WO | WO 2017/070632 A2 | 4/2017 |
| WO | WO 2018/009903 A2 | 1/2018 |
| WO | WO 2018/027078 A1 | 2/2018 |
| WO | WO 2018/039438 A1 | 3/2018 |
| WO | WO 2018/109447 A1 | 6/2018 |
| WO | WO 2018/136939 A1 | 7/2018 |
| WO | WO 2019/040935 A1 | 2/2019 |
| WO | WO 2019/067815 A2 | 4/2019 |

OTHER PUBLICATIONS

Extended European Search Report, dated May 26, 2017, in connection with Application No. EP 16 20 3684.

International Search Report and Written Opinion, dated Jun. 21, 2010, in connection with Application No. PCT/US2009/056194.

International Preliminary Report on Patentability, dated Mar. 17, 2011, in connection with Application No. PCT/US2009/056194.

(56) References Cited

OTHER PUBLICATIONS

Extended European Search Report, dated May 16, 2017, in connection with Application No. EP 17 16 0955.
Invitation to Pay Additional Fees, mailed Aug. 30, 2012, in connection with Application No. PCT/US2011/066747.
International Search Report and Written Opinion, dated Oct. 30, 2012, in connection with Application No. PCT/US2011/066747.
International Preliminary Report on Patentability, dated Jul. 4, 2013, in connection with Application No. PCT/US2011/066747.
International Search Report and Written Opinion, dated Sep. 25, 2015, in connection with Application No. PCT/US2015/012022.
International Preliminary Report on Patentability, dated Aug. 4, 2016, in connection with Application No. PCT/US2015/012022.
Invitation to Pay Additional Fees, mailed Jan. 12, 2017, in connection with Application No. PCT/US/2016/043559.
International Search Report and Written Opinion, dated Mar. 10, 2017, in connection with Application No. PCT/US/2016/043559.
International Preliminary Report on Patentability, dated Feb. 1, 2018, in connection with Application No. PCT/US/2016/043559.
International Search Report and Written Opinion, dated Jun. 10, 2016, in connection with Application No. PCT/US2015/057012.
International Preliminary Report on Patentability, dated May 4, 2017, in connection with Application No. PCT/US2015/057012.
International Search Report and Written Opinion, dated Aug. 11, 2016, in connection with Application No. PCT/US2016/027795.
International Preliminary Report on Patentability, dated Oct. 26, 2017, in connection with Application No. PCT/US2016/027795.
Invitation to Pay Additional Fees, mailed Oct. 12, 2016, in connection with Application No. PCT/US2016/044546.
International Search Report and Written Opinion, dated Dec. 28, 2016, in connection with Application No. PCT/US2016/044546.
International Preliminary Report on Patentability, dated Feb. 8, 2018, in connection with Application No. PCT/US/2016/044546.
International Search Report and Written Opinion, dated Nov. 30, 2016, in connection with Application No. PCT/US2016/043513.
International Preliminary Report on Patentability, dated Feb. 1, 2018, in connection with Application No. PCT/US2016/043513.
Invitation to Pay Additional Fees, mailed Apr. 5, 2018, in connection with Application No. PCT/US2018/14867.
International Search Report and Written Opinion, dated May 23, 2018, in connection with Application No. PCT/US2018/14867.
International Preliminary Report on Patentability, dated Aug. 1, 2019, in connection with Application No. PCT/US2018/14867.
Invitation to Pay Additional Fees, mailed Sep. 12, 2018, in connection with Application No. PCT/US2018/040692.
International Search Report and Written Opinion, dated Nov. 15, 2018, in connection with Application No. PCT/US2018/040692.
International Preliminary Report on Patentability, dated Jan. 16, 2020, in connection with Application No. PCT/US2018/040692.
Invitation to Pay Additional Fees, mailed Jan. 4, 2019, in connection with Application No. PCT/US2018/051557.
International Search Report and Written Opinion, dated Feb. 25, 2019, in connection with Application No. PCT/US2018/051557.
International Preliminary Report on Patentability, dated Apr. 2, 2020, in connection with Application No. PCT/US2018/051557.
International Search Report and Written Opinion, dated Nov. 21, 2018, in connection with Application No. PCT/US2018/044242.
International Search Report and Written Opinion, dated Sep. 4, 2019, in connection with Application No. PCT/US2019/037216.
Invitation to Pay Additional Fees, mailed Nov. 19, 2018, in connection with Application No. PCT/US18/48134.
International Search Report and Written Opinion, dated Jan. 22, 2019, in connection with Application No. PCT/US18/48134.
International Preliminary Report on Patentability, dated Mar. 5, 2020, in connection with Application No. PCT/US18/48134.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 22, 2003;100(15):8688-91. Epub Jul. 1, 2003.
Armstrong et al., Chapter 3. Vectors for Phage Display. In: Phage Display of Peptides and Proteins. Kay et al., eds. Academic Press. San Diego, CA. 1996:35-53.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Boch et al., Breaking the code of DNA binding specificity of TAL-type III effectors. Science. Dec. 11, 2009;326(5959):1509-12. doi: 10.1126/science.1178811.
Boeke et al., Effects of bacteriophage f1 gene III protein on the host cell membrane. Mol Gen Genet. 1982;186(2):185-92.
Boersma et al., Selection strategies for improved biocatalysts. FEBS J. May 2007;274(9):2181-95.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Cadwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Cattaneo et al., SEL1L affects human pancreatic cancer cell cycle and invasiveness through modulation of PTEN and genes related to cell-matrix interactions. Neoplasia. 2005;7(11):1030-1038.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.

(56) References Cited

OTHER PUBLICATIONS

Cheetham et al., Structural basis for initiation of transcription from an RNA polymerase-promoter complex. Nature. May 6, 1999;399(6731):80-3.

Chen et al., Information theory based T7-like promoter models: classification of bacteriophages and differential evolution of promoters and their polymerases. Nucleic Acids Res. Oct. 31, 2005;33(19):6172-87. Print 2005.

Chen, Clinical uses of botulinum neurotoxins: current indications, limitations and future developments. Toxins (Basel). 2012;4(10):913-939.

Clackson et al., Making antibody fragments using phage display libraries. Nature. Aug. 15, 1991;352(6336):624-8.

Click et al., Filamentous phage infection: required interactions with the TolA protein. J Bacteriol. Oct. 1997;179(20):6464-71.

Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.

Corey et al., Trypsin display on the surface of bacteriophage. Gene. Jun. 15, 1993;128(1):129-34.

Crameri et al., Display of biologically active proteins on the surface of filamentous phages: a cDNA cloning system for selection of functional gene products linked to the genetic information responsible for their production. Gene. Dec. 27, 1993;137(1):69-75.

Cwirla et al., Peptides on phage: a vast library of peptides for identifying ligands. Proc Natl Acad Sci U S A. Aug. 1990;87(16):6378-82.

Das et al., Viral evolution as a tool to improve the tetracycline-regulated gene expression system. J Biol Chem. Apr. 30, 2004;279(18):18776-82. Epub Feb. 2, 2004.

Datsenko et al., One-step inactivation of chromosomal genes in *Escherichia coli* K-12 using PCR products. Proc Natl Acad Sci U S A. Jun. 6, 2000;97(12):6640-5.

Davis et al., Viral mutagenesis as a means for generating novel proteins. J Virol. Feb. 2010;84(3):1625-30. Epub Nov. 11, 2009.

De Haard et al., A large non-immunized human Fab fragment phage library that permits rapid isolation and kinetic analysis of high affinity antibodies. J Biol Chem. Jun. 25, 1999;274(26):18218-30.

Deribe, Mechanistic insights into the role of truncating PREX2 mutations in melanoma. Mol Cell Oncol. 2016;3(3):e1160174.

Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.

Dickinson et al., A system for the continuous directed evolution of proteases rapidly reveals drug-resistance mutations. Nat Commun. Oct. 30, 2014;5:5352. doi: 10.1038/ncomms6352.

Dickinson et al., Experimental interrogation of the path dependence and stochasticity of protein evolution using phage-assisted continuous evolution. Proc Natl Acad Sci U S A. May 2013;110(22):9007-12.

Dove et al., Conversion of the omega subunit of *Escherichia coli* RNA polymerase into a transcriptional activator or an activation target. Genes Dev. Mar. 1, 1998;12(5):745-54.

Doyon et al., Directed evolution and substrate specificity profile of homing endonuclease I-SceI. J Am Chem Soc. Feb. 22, 2006;128(7):2477-84.

Drake, A constant rate of spontaneous mutation in DNA-based microbes. Proc Natl Acad Sci U S A. Aug. 15, 1991;88(16):7160-4.

Durai et al., A bacterial one-hybrid selection system for interrogating zinc finger-DNA interactions. Comb Chem High Throughput Screen. May 2006;9(4):301-11.

Durniak et al., The structure of a transcribing T7 RNA polymerase in transition from initiation to elongation. Science. Oct. 24, 2008;322(5901):553-7.

Esvelt et al., A system for the continuous directed evolution of biomolecules. Nature. Apr. 28, 2011;472(7344):499-503. Epub Apr. 10, 2011.

Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.

Fowlkes et al., Multipurpose vectors for peptide expression on the M13 viral surface. Biotechniques. Sep. 1992;13(3):422-8.

Friedberg et al., Error-prone DNA polymerases: novel structures and the benefits of infidelity. Cell. Oct. 5, 2001;107(1):9-12.

Fuchs et al., Targeting Recombinant Antibodies to the Surface of *Escherichia coli*: Fusion to a Peptidoglycan Associated Lipoprotein. Bio/Technology. 1991;9:1370-72.

Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.

Garrard et al., Fab assembly and enrichment in a monovalent phage display system. Biotechnology (N Y). Dec. 1991;9(12):1373-7.

Gibson et al., Enzymatic assembly of DNA molecules up to several hundred kilobases. Nat Methods. May 2009;6(5):343-5. Epub Apr. 12, 2009.

Gordley et al., Evolution of programmable zinc finger-recombinases with activity in human cells. J Mol Biol. Mar. 30, 2007;367(3):802-13. Epub Jan. 12, 2007.

Gram et al., In vitro selection and affinity maturation of antibodies from a naive combinatorial immunoglobulin library. Proc Natl Acad Sci U S A. Apr. 15, 1992;89(8):3576-80.

Griffiths et al., Human anti-self antibodies with high specificity from phage display libraries. EMBO J. Feb. 1993;12(2):725-34.

Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.

Harris et al., Measurement of enzyme activity. Methods Enzymol. 2009;463:57-71.

Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.

Hawkins et al., Selection of phage antibodies by binding affinity. Mimicking affinity maturation. J Mol Biol. Aug. 5, 1992;226(3):889-96.

Hay et al., Bacteriophage cloning and *Escherichia coli* expression of a human IgM Fab. Hum Antibodies Hybridomas. Apr. 1992;3(2):81-5.

Hoogenboom et al., Antibody phage display technology and its applications. Immunotechnology. Jun. 1998;4(1):1-20.

Hoogenboom et al., Multi-subunit proteins on the surface of filamentous phage: methodologies for displaying antibody (Fab) heavy and light chains. Nucleic Acids Res. Aug. 11, 1991;19(15):4133-7.

Hoogenboom et al., Natural and designer binding sites made by phage display technology. Immunol Today. Aug. 2000;21(8):371-8.

Houshmand et al., Use of Bateriophage T7 Displayed Peptides for Determination of Monoclonal Anitbody Specificity and Biosensor Analysis of the Binding Reaction. Anal Biochem. 1999;268:363-70.

Hu et al., *Escherichia coli* one- and two-hybrid systems for the analysis and identification of protein-protein interactions. Methods. Jan. 2000;20(1):80-94.

Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.

Huse et al., Generation of a large combinatorial library of the immunoglobulin repertoire in phage lambda. Science. Dec. 8, 1989;246(4935):1275-81.

Husimi et al., Cellstat—a continuous culture system of a bacteriophage for the study of the mutation rate and the selection process of the DNA level. Rev Sci Instrum. Apr. 1982;53(4):517-22.

Husimi, Selection and evolution of bacteriophages in cellstat. Adv Biophys. 1989;25:1-43.

Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.

Ikeda et al., In vivo and in vitro activities of point mutants of the bacteriophage T7 RNA polymerase promoter. Biochemistry. Sep. 22, 1992;31(37):9073-80.

(56) References Cited

OTHER PUBLICATIONS

Ikeda et al., Selection and characterization of a mutant T7 RNA polymerase that recognizes an expanded range of T7 promoter-like sequences. Biochemistry. Sep. 7, 1993;32(35):9115-24.

Imburgio et al., Studies of promoter recognition and start site selection by T7 RNA polymerase using a comprehensive collection of promoter variants. Biochemistry. Aug. 29, 2000;39(34):10419-30.

Irion et al., Identification and targeting of the ROSA26 locus in human embryonic stem cells. Nat Biotechnol. Dec. 2007;25(12):1477-82. Epub Nov. 25, 2007.

Johns et al., The promise and peril of continuous in vitro evolution. J Mol Evol. Aug. 2005;61(2):253-63. Epub Jun. 27, 2005.

Joho et al., Identification of a region of the bacteriophage T3 and T7 RNA polymerases that determines promoter specificity. J Mol Biol. Sep. 5, 1990;215(1):31-9.

Joung et al., A bacterial two-hybrid selection system for studying protein-DNA and protein-protein interactions. Proc Natl Acad Sci U S A. Jun. 20, 2000;97(13):7382-7.

Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.

Kawarasaki et al., Enhanced crossover SCRATCHY: construction and high-throughput screening of a combinatorial library containing multiple non-homologous crossovers. Nucleic Acids Res. Nov. 1, 2003;31(21):e126.

Khlebnikov et al., Modulation of gene expression from the arabinose-inducible araBAD promoter. J Ind Microbiol Biotechnol. Jul. 2002;29(1):34-7.

Kim et al., DJ-1, a novel regulator of the tumor suppressor PTEN. Cancer Cell. 2005;7(3):263-273.

Kim et al., Increasing the genome-targeting scope and precision of base editing with engineered Cas9-cytidine deaminase fusions. Nature Biotechnology; Feb. 13, 2007; 35(4): 371-376.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Komor et al., Programmable editing of a target base in genomic DNA without double-stranded DNA cleavage. Nature. May 19, 2016;533(7603):420-4. doi: 10.1038/nature17946. Epub Apr. 20, 2016.

Kozak et al., Structural features in eukaryotic mRNAs that modulate the initiation of translation. J Biol Chem. Oct. 25, 1991;266(30):19867-70.

Kuzmine et al., Binding of the priming nucleotide in the initiation of transcription by T7 RNA polymerase. J Biol Chem. Jan. 31, 2003;278(5):2819-23. Epub Nov. 9, 2002.

Laskowska et al., IbpA and IbpB, the new heat-shock proteins, bind to endogenous *Escherichia coli* proteins aggregated intracellularly by heat shock. Biochimie. 1996;78(2):117-22.

Latimer et al., Specificity of monoclonal antibodies produced against phosphorothioate and ribo modified DNAs. Mol Immunol. Oct. 1995;32(14-15):1057-64.

Leconte et al., A population-based experimental model for protein evolution: effects of mutation rate and selection stringency on evolutionary outcomes. Biochemistry. Feb. 26, 2013; 52(8): 1490-1499.

Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.

Lincoln et al., Self-sustained replication of an RNA enzyme. Science. Feb. 27, 2009;323(5918):1229-32. Epub Jan. 8, 2009.

Lindemann et al., Evolution of bacteriophage in continuous culture: a model system to test antiviral gene therapies for the emergence of phage escape mutants. J Virol. Jun. 2002;76(11):5784-92.

Lu, The destructive effect of botulinum neurotoxins on the SNARE protein: SNAP-25 and synaptic membrane fusion. PeerJ. 2015;3:e1065. Published Jun. 30, 2015.

Lutz et al., Creating multiple-crossover DNA libraries independent of sequence identity. Proc Natl Acad Sci U S A. Sep. 25, 2001;98(20):11248-53. Epub Sep. 18, 2001.

Maeder et al., Robust, synergistic regulation of human gene expression using TALE activators. Nat Methods. Mar. 2013;10(3):243-5. doi: 10.1038/nmeth.2366. Epub Feb. 10, 2013.

Makeyev et al., Evolutionary potential of an RNA virus. J Virol. Feb. 2004;78(4):2114-20.

Malmborg et al., Selective phage infection mediated by epitope expression on F pilus. J Mol Biol. Oct. 31, 1997;273(3):544-51.

Martin et al., Kinetic analysis of T7 RNA polymerase-promoter interactions with small synthetic promoters. Biochemistry. May 19, 1987;26(10):2690-6.

Masuyer et al., Engineered botulinum neurotoxins as new therapeutics. Annu Rev Pharmacol Toxicol. 2014;54:27-51.

McCafferty et al., Phage antibodies: filamentous phage displaying antibody variable domains. Nature. Dec. 6, 1990;348(6301):552-4.

McConnell et al., Constrained peptide libraries as a tool for finding mimotopes. Gene. Dec. 30, 1994;151(1-2):115-8.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

Mihai et al., PTEN inhibition improves wound healing in lung epithelia through changes in cellular mechanics that enhance migration. Am J Physiol Lung Cell Mol Physiol. 2012;302(3):L287-L299.

Miller et al., A TALE nuclease architecture for efficient genome editing. Nat Biotechnol. Feb. 2011;29(2):143-8. doi:10.1038/nbt.1755. Epub Dec. 22, 2010.

Milligan et al., Oligoribonucleotide synthesis using T7 RNA polymerase and synthetic DNA templates. Nucleic Acids Res. Nov. 11, 1987;15(21):8783-98.

Mills et al., An extracellular Darwinian experiment with a self-duplicating nucleic acid molecule. Proc Natl Acad Sci U S A. Jul. 1967;58(1):217-24.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Nelson et al., Filamentous phage DNA cloning vectors: a noninfective mutant with a nonpolar deletion in gene III. Virology. Jan. 30, 1981;108(2):338-50.

Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.

O'Maille et al., Structure-based combinatorial protein engineering (SCOPE). J Mol Biol. Aug. 23, 2002;321(4):677-91.

Oeemig et al., Solution structure of DnaE intein from Nostoc punctiforme: structural basis for the design of a new split intein suitable for site-specific chemical modification. FEBS Lett. May 6, 2009;583(9):1451-6.

Opperman et al., A model for a umuDC-dependent prokaryotic DNA damage checkpoint. Proc Natl Acad Sci U S A. Aug. 3, 1999;96(16):9218-23.

Ostendorf et al., Characterization of a dam mutant of Serratia marcescens and nucleotide sequence of the dam region. J Bacteriol. Jul. 1999;181(13):3880-5.

Ostermeier et al., A combinatorial approach to hybrid enzymes independent of DNA homology. Nat Biotechnol. Dec. 1999;17(12):1205-9.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Rakonjac et al., Filamentous phage are released from the bacterial membrane by a two-step mechanism involving a short C-terminal fragment of pIII. J Mol Biol. Jun. 25, 1999;289(5):1253-65.

(56) References Cited

OTHER PUBLICATIONS

Rakonjac et al., Filamentous phage infection-mediated gene expression: construction and propagation of the gIII deletion mutant helper phage R408d3. Gene. Oct. 1, 1997;198(1-2):99-103.
Rakonjac et al., Roles of pIII in filamentous phage assembly. J Mol Biol. Sep. 11, 1998;282(1):25-41.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 RNA polymerase mutants with altered promoter specificities. Proc Natl Acad Sci U S A. Apr. 15, 1993;90(8):3147-51.
Rawlings et al., MEROPS: the database of proteolytic enzymes, their substrates and inhibitors. Nucleic Acids Res. Jan. 2014;42(Database issue):D503-9.
Rebar et al., Phage display methods for selecting zinc finger proteins with novel DNA-binding specificities. Methods Enzymol. 1996;267:129-49.
Reidhaar-Olson et al., Random mutagenesis of protein sequences using oligonucleotide cassettes. Methods Enzymol. 1991;208:564-86.
Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.
Riechmann et al., The C-terminal domain of TolA is the coreceptor for filamentous phage infection of *E. coli*. Cell. Jul. 25, 1997;90(2):351-60.
Ringquist et al., Translation initiation in *Escherichia coli*: sequences within the ribosome-binding site. Mol Microbiol. May 1992;6(9):1219-29.
Rosenberg et al., T7 Select® Phage Display System: A Powerful new protein display system based on bacteriophage T7. Innovations. 1996;6:1-6.
Santini et al., Efficient display of an HCV cDNA expression library as C-terminal fusion to the capsid protein D of bacteriophage lambda. J Mol Biol. Sep. 11, 1998;282(1):125-35.
Santoro et al., Directed evolution of the site specificity of Cre recombinase. Proc Natl Acad Sci U S A. Apr. 2, 2002;99(7):4185-90. Epub Mar. 19, 2002.
Schultz et al., Oligo-2'-fluoro-2'-deoxynucleotide N3'→P5' phosphoramidates: synthesis and properties. Nucleic Acids Res. Aug. 1, 1996;24(15):2966-73.
Scott et al., Searching for peptide ligands with an epitope library. Science. Jul. 27, 1990;249(4967):386-90.
Sices et al., A genetic screen for the isolation and characterization of site-specific proteases. Proc Natl Acad Sci U S A. Mar. 17, 1998;95(6):2828-33.
Sices et al., Rapid genetic selection of inhibitor-resistant protease mutants: clinically relevant and novel mutants of the HIV protease. AIDS Res Hum Retroviruses. Sep. 1, 2001;17(13):1249-55.
Sieber et al., Libraries of hybrid proteins from distantly related sequences. Nat Biotechnol. May 2001;19(5):456-60.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Smith, Filamentous fusion phage: novel expression vectors that display cloned antigens on the virion surface. Science. Jun. 14, 1985;228(4705):1315-7.
Stemmer, Rapid evolution of a protein in vitro by DNA shuffling. Nature. Aug. 4, 1994;370(6488):389-91.
Sutter et al., Non-replicating vaccinia vector efficiently expresses bacteriophage T7 RNA polymerase. FEBS Lett. Aug. 28, 1995;371(1):9-12.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tsuji et al., Random multi-recombinant PCR for the construction of combinatorial protein libraries. Nucleic Acids Res. Oct. 15, 2001;29(20):E97.
Tzagoloff et al., The Initial Steps in Infection With Coliphage M13. Virology. Nov. 1964;24:372-80.
Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Continuous directed evolutions of proteins with improved soluble expression. Nature Chemical Biology. Nat Publishing Group. Aug. 20, 2018; 14(10):972-980.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Webb et al., Production of catalytically inactive BoNT/A1 holoprotein and comparison with BoNT/A1 subunit vaccines against toxin subtypes A1, A2, and A3. Vaccine. 2009;27(33):4490-4497.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wright et al., Continuous in vitro evolution of catalytic function. Science. Apr. 25, 1997;276(5312):614-7.
Yamamoto et al., Virological and immunological bases for HIV-1 vaccine design. Uirusu 2007;57(2):133-139. https://doi.org/10.2222/jsv.57.133.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
U.S. Appl. No. 13/062,098, filed Apr. 4, 2011, Liu et al.
U.S. Appl. No. 14/704,226, filed May 5, 2015, Liu et al.
U.S. Appl. No. 15/713,403, filed Sep. 22, 2017, Liu et al.
U.S. Appl. No. 13/996,208, filed Jun. 20, 2013, Liu et al.
U.S. Appl. No. 15/188,627, filed Jun. 21, 2016, Liu et al.
U.S. Appl. No. 16/410,767, filed May 13, 2019, Liu et al.
U.S. Appl. No. 15/112,759, filed Jul. 20, 2016, Liu et al.
U.S. Appl. No. 16/238,386, filed Jan. 2, 2019, Liu et al.
U.S. Appl. No. 15/217,839, filed Jul. 22, 2016, Liu et al.
U.S. Appl. No. 15/518,639, filed Apr. 12, 2017, Liu et al.
U.S. Appl. No. 15/567,312, filed Oct. 17, 2017, Liu et al.
U.S. Appl. No. 15/748,053, filed Jan. 26, 2018, Liu et al.
U.S. Appl. No. 16/804,228, filed Feb. 28, 2020, Liu et al.
U.S. Appl. No. 15/216,844, filed Jul. 22, 2016, Liu et al.
U.S. Appl. No. 16/521,371, filed Jul. 24, 2019, Liu et al.
U.S. Appl. No. 16/628,456, filed Jan. 3, 2020, Liu et al.
U.S. Appl. No. 16/641,630, filed Feb. 24, 2020, Liu et al.
EP 09812363.1, Mar. 30, 2012, Extended European Search Report.
EP 16 20 3684, May 26, 2017, Extended European Search Report.
PCT/US2009/056194, Jun. 21, 2010, International Search Report and Written Opinion.
PCT/US2009/056194, Mar. 17, 2011, International Preliminary Report on Patentability.
EP 17 16 0955, May 16, 2017, Extended European Search Report.
PCT/US2011/066747, Aug. 30, 2012, Invitation to Pay Additional Fees.

(56) References Cited

OTHER PUBLICATIONS

PCT/US2011/066747, Oct. 30, 2012, International Search Report and Written Opinion.
PCT/US2011/066747, Jul. 4, 2013, International Preliminary Report on Patentability.
PCT/US2015/012022, Sep. 25, 2015, International Search Report and Written Opinion.
PCT/US2015/012022, Aug. 4, 2016, International Preliminary Report on Patentability.
PCT/US/2016/043559, Jan. 12, 2017, Invitation to Pay Additional Fees.
PCT/US/2016/043559, Mar. 10, 2017, International Search Report and Written Opinion.
PCT/US/2016/043559, Feb. 1, 2018, International Preliminary Report on Patentability.
PCT/US2015/057012, Jun. 10, 2016, International Search Report and Written Opinion.
PCT/US2015/057012, May 4, 2017, International Preliminary Report on Patentability.
PCT/US2016/027795, Aug. 11, 2016, International Search Report and Written Opinion.
PCT/US2016/027795, Oct. 26, 2017, International Preliminary Report on Patentability.
PCT/US2016/044546, Oct. 12, 2016, Invitation to Pay Additional Fees.
PCT/US2016/044546, Dec. 28, 2016, International Search Report and Written Opinion.
PCT/US2016/044546, Feb. 8, 2018, International Preliminary Report on Patentability.
PCT/US2016/043513, Nov. 30, 2016, International Search Report and Written Opinion.
PCT/US2016/043513, Feb. 1, 2018, International Preliminary Report on Patentability.
PCT/US2018/14867, Apr. 5, 2018, Invitation to Pay Additional Fees.
PCT/US2018/14867, May 23, 2018, International Search Report and Written Opinion.
PCT/US2018/14867, Aug. 1, 2019, International Preliminary Report on Patentability.
PCT/US2018/040692, Sep. 12, 2018, International Search Report and Written Opinion.
PCT/US2018/040692, Nov. 15, 2018, International Search Report and Written Opinion.
PCT/US2018/040692, Jan. 16, 2020, International Preliminary Report on Patentability.
PCT/US2018/051557, Jan. 4, 2019, Invitation to Pay Additional Fees.
PCT/US2018/051557, Feb. 25, 2019, International Search Report and Written Opinion.
PCT/US2018/051557, Apr. 2, 2020, International Preliminary Report on Patentability.
PCT/US2018/044242, Nov. 21, 2018, International Search Report and Written Opinion.
PCT/US2019/037216, Sep. 4, 2019, International Search Report and Written Opinion.
PCT/US18/481134, Nov. 19, 2018, Invitation to Pay Additional Fees.
PCT/US18/481134, Jan. 22, 2019, International Search Report and Written Opinion.
PCT/US18/481134, Mar. 5, 2020, International Preliminary Report on Patentability.
U.S. Appl. No. 17/541,848, filed Dec. 3, 2021, Liu et al.
U.S. Appl. No. 17/123,632, filed Dec. 16, 2020, Liu et al.
U.S. Appl. No. 17/581,235, filed Jan. 21, 2022, Badran et al.
U.S. Appl. No. 17/355,735, filed Jun. 23, 2021, Liu et al.
U.S. Appl. No. 17/398,870, filed Aug. 10, 2021, Liu et al.
U.S. Appl. No. 17/251,276, filed Dec. 11, 2020, Liu et al.
U.S. Appl. No. 17/627,035, filed Jan. 13, 2022, Liu et al.
PCT/US2019/037216, Dec. 24, 2020, International Preliminary Report on Patentability.
EP18847527.1, Apr. 21, 2021, Partial European Search Report.
EP18847527.1, Aug. 2, 2021, Extended European Search Report.
PCT/US2020/042016, Oct. 13, 2020, Invitation to Pay Additional Fees.
PCT/US2020/042016, Dec. 10, 2020, International Search Report and Written Opinion.
PCT/US2020/042016, Jan. 27, 2022, International Preliminary Report on Patentability.
International Preliminary Report on Patentability, dated Dec. 24, 2020, in connection with Application No. PCT/US2019/037216.
Partial European Search Report for Application No. 18847527.1, dated Apr. 21, 2021.
Extended European Search Report for Application No. 18847527.1, dated Aug. 2, 2021.
Invitation to Pay Additional Fees, mailed Oct. 13, 2020, in connection with Application No. PCT/US2020/042016.
International Search Report and Written Opinion, dated Dec. 10, 2020, in connection with Application No. PCT/US2020/042016.
International Preliminary Report on Patentability dated Jan. 27, 2022, in connection with Application No. PCT/US2020/042016.
[No Author Listed] Genbank Submission. NCBI; Accession No. WP_010869888, version WP_010869888.1. tyrosine—tRNA ligase [Methanocaldococcus jannaschii]. Jun. 1, 2019.
Genbank Submission. NCBI; Accession No. WP_011033391, version WP_011033391.1. pyrrolysine—tRNA(Pyl) ligase [Methanosarcina mazei], Polycarpo et al.; Nov. 29, 2019.
Genbank Submission. NCBI; Accession No. WP_011305865, version WP_011305865.1. pyrrolysine—tRNA(Pyl) ligase [Methanosarcina barkeri].Polycarpo et al.; Nov. 29, 2019.
Agarwal et al., Mode of VAMP substrate recognition and inhibition of Clostridium botulinum neurotoxin F. Nat Struct Mol Biol. Jul. 2009;16(7):789-94. doi: 10.1038/nsmb.1626. Epub Jun. 21, 2009.
Amiram et al,. Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015.
Bade et al., Botulinum neurotoxin type D enables cytosolic delivery of enzymatically active cargo proteins to neurones via unfolded translocation intermediates. J Neurochem. Dec. 2004;91(6):1461-72.
Binz et al., Clostridial neurotoxins: mechanism of SNARE cleavage and outlook on potential substrate specificity reengineering. Toxins. Apr. 2010;2(4):665-82. Epub Apr. 13, 2010.
Blum et al., Phage-assisted evolution of botulinum neurotoxin proteases with reprogrammed specificity. Science. Feb. 19, 2021;371(6531):803-810. doi: 10.1126/science.abf5972.
Blum, Continuous evolution of bacterial neurotoxins for intracellular protease therapy. 2019. Poster. 1 page.
Blum, Generation of selective botulinum neurotoxin proteases with reprogrammed substrate specificity through phage-assisted directed evolution. Apr. 7, 2020. Powerpoint. 36 pages.
Blum, Generation of selective botulinum neurotoxin proteases with reprogrammed substrate specificity through phage-assisted directed evolution. Jun. 4, 2019. Powerpoint. 24 pages.
Box et al., A multi-domain protein system based on the HC fragment of tetanus toxin for targeting DNA to neuronal cells. J Drug Target. Jul. 2003;11(6):333-43. doi: 10.1080/10611860310001634667.
Canitrot et al., Overexpression of DNA polymerase beta in cell results in a mutator phenotype and a decreased sensitivity to anticancer drugs. Proc Natl Acad Sci U S A. Oct. 13, 1998;95(21):12586-90. doi: 10.1073/pnas.95.21.12586.
Chaddock et al., Inhibition of vesicular secretion in both neuronal and nonneuronal cells by a retargeted endopeptidase derivative of Clostridium botulinum neurotoxin type A. Infect. Immun. May 2000;68(5):2587-93.
Chaineau et al., Multiple roles of the vesicular-SNARE TI-VAMP in post-Golgi and endosomal trafficking. FEBS Letters. Oct. 2009;583:3817-26.
Chen et al., Engineering botulinum neurotoxin to extend therapeutic intervention. PNAS. Jun. 2009;106(23):9180-4.
Chen et al., SNARE-mediated membrane fusion. Nat Rev Mol Cell Biol. Feb. 2001;2(2):98-106.

(56) References Cited

OTHER PUBLICATIONS

Chen et al., VAMP8 facilitates cellular proliferation and temozolomide resistance in human glioma cells. Neuro-Oncology. 2015;17(3):407-18. Epub Sep. 10, 2014.
Chin, Expanding and reprogramming the genetic code of cells and animals. Annu Rev Biochem. 2014;83:379-408. doi: 10.1146/annurev-biochem-060713-035737. Epub Feb. 10, 2014.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cong et al., Multiplex genome engineering using CRISPR/Cas systems. Science. 2013; 339: 819-23.
Craik et al., Proteases as therapeutics. Biochem J. Apr. 2011;435(1):16 pages.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Duggan et al., Inhibition of Release of Neurotransmitters from Rat Dorsal Root Ganglia by a Novel Conjugate of a Clostridium botulinum Toxin A Endopeptidase Fragment and Erythrina cristagalli Lectin. The Journal of Biological Chemistry. Sep. 2002;277(38):34846-52.
Fan et al., Rationally evolving tRNAPyl for efficient incorporation of noncanonical amino acids. Nucleic Acids Res. Dec. 15, 2015;43(22):e156. doi: 10.1093/nar/gkv800. Epub Aug. 6, 2015.
Feng et al., ExoI: A new chemical inhibitor of the exocytic pathway. PNAS. May 2003;100(11):6469-74.
Ferretti et al., Complete genome sequence of an M1 strain of *Streptococcus pyogenes*. Proc Natl Acad Sci U S A. Apr. 10, 2001;98(8):4658-63. doi: 10.1073/pnas.071559398.
Foster et al., Re-engineering the target specificity of Clostridial neurotoxins—A route to novel therapeutics. Neurotoxicity Research. May 2006;9(2,3):101-7.
Foster et al., Targeted Secretion Inhibitors—Innovative Protein Therapeutics. Toxins. Dec. 2010;2:2795-815.
Fu et al., Promises and Pitfalls of Intracellular Delivery of Proteins. Bioconjugate Chemistry. Aug. 2014;25:1602-8.
Gill, Bacterial Toxins: a Table of Letal Amounts. Microbiological Reviews. Mar. 1982;46(1):86-94.
Goodnough et al., Development of a delivery vehicle for intracellular transport of botulinum neurotoxin antagonists. FEBS Lett. Feb. 27, 2002;513(2-3):163-8.
Guilinger et al., Fusion of catalytically inactive Cas9 to FokI nuclease improves the specificity of genome modification. Nat. Biotechnol. 2014; 32(6): 577-82. doi: 10.1038/nbt.2909. Epub Apr. 25, 2014.
Guo et al., Evolution of amber suppressor tRNAs for efficient bacterial production of proteins containing nonnatural amino acids. Angew Chem Int Ed Engl. 2009;48(48):9148-51. doi: 10.1002/anie.200904035.
Guo et al., Polyspecific pyrrolysyl-tRNA synthetases from directed evolution. Proc Natl Acad Sci U S A. Nov. 25, 2014;III(47):16724-9. doi: 10.1073/pnas.1419737111. Epub Nov. 10, 2014.
Guzman et al., Tight regulation, modulation, and high-level expression by vectors containing the arabinose PBAD promoter. J Bacteriol. 1995;177(14):4121-4130.
Hedstrom et al., Converting trypsin to chymotrypsin: the role of surface loops. Science. Mar. 1992;255(5049):1249-53.
Hendricks et al., The S. cerevisiae Mag1 3-methyladenine DNA glycosylase modulates susceptibility to homologous recombination. DNA Repair (Amst). 2002;1(8):645-659.
Herring et al., The amino-terminal domain of pyrrolysyl-tRNA synthetase is dispensable in vitro but required for in vivo activity. FEBS Lett. Jul. 10, 2007;581(17):3197-203. doi: 10.1016/j.febslet.2007.06.004. Epub Jun. 12, 2007.

Ho et al., Recombinant botulinum neurotoxin A heavy chainbased delivery vehicles for neuronal cell targeting. Protein Engineering, Design & Selection. 2011;24(3):247-53. Epub Nov. 4, 2010.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jankovic et al., Direct selection and phage display of a Gram-positive secretome. Genome Biology. Dec. 13, 2007; 8(266):1-15.
Jiang et al., PylSn and the homologous N-terminal domain of pyrrolysyl-tRNA synthetase bind the tRNA that is essential for the genetic encoding of pyrrolysine. J Biol Chem. Sep. 21, 2012;287(39):32738-46. doi: 10.1074/jbc.M112.396754. Epub Jul. 31, 2012.
Jiang et al., RNA guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Kasai et al., Distinct initial SNARE configurations underlying the diversity of exocytosis. Physiol Rev. Oct. 2012;92(4):1915-64. doi: 10.1152/physrev.00007.2012.
Kavran et al., Structure of pyrrolysyl-tRNA synthetase, an archaeal enzyme for genetic code innovation. Proc Natl Acad Sci U S A. Jul. 3, 2007;104(27):11268-73. doi: 10.1073/pnas.0704769104. Epub Jun. 25, 2007.
Köhler, A yeast-based growth assay for the analysis of site-specific proteases. Nucleic Acids Res. 2003;31(4):e16. 5 pages.
Lebeda et al., The Zinc-Dependent Protease Activity of the Botulinum Neurotoxins. Toxins. May 2010;2:978-97.
Liu et al., Adding new chemistries to the genetic code. Annu Rev Biochem. 2010;79:413-44. doi: 10.1146/annurev.biochem.052308.105824.
Liu et al., PTEN deletion enhances the regenerative ability of adult corticospinal neurons. Nat Neurosci. Sep. 2010;13(9):1075-81. doi: 10.1038/nn.2603. Epub Aug. 8, 2010.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19. doi: 10.1074/jbc.272.34.21408.
Mali et al., RNA-guided human genome engineering via Cas9. Science. 2013; 339:823-26.
Marcet-Palacios et al., Vesicle-associated membrane protein 7 (VAMP-7) is essential for target cell killing in a natural killer cell line. Biochem Biophys Res Commun. Feb. 15, 2008;366(3):617-23. doi: 10.1016/j.bbrc.2007.11.079. Epub Nov. 26, 2007.
Meng et al., Role of SNARE proteins in tumourigenesis and their potential as targets for novel anti-cancer therapeutics. Biochim Biophys Acta. Aug. 2015;1856(1):1-12. doi: 10.1016/j.bbcan.2015.04.002. Epub May 5, 2015.
Ngo et al., Computational Complexity, Protein Structure Prediction, and the Levinthal Paradox in the Protein Folding Problem and Tertiary Structure Prediction. Merz et al., Eds. 1994. pp 433 and 492-495.
Nicholson-Fish et al., VAMP4 is an Essential Cargo Molecule for Activity-Dependent Bulk Endocytosis. Neuron. Dec. 2, 2015;88(5):973-984. doi: 10.1016/j.neuron.2015.10.043. Epub Nov. 19, 2015.
Nozawa et al., Pyrrolysyl-tRNA synthetase-tRNA(Pyl) structure reveals the molecular basis of orthogonality. Nature. Feb. 26, 2009;457(7233):1163-7. doi: 10.1038/nature07611. Epub Dec. 31, 2008.
O'Donoghue et al., Upgrading protein synthesis for synthetic biology. Nat Chem Biol. Oct. 2013;9(10):594-8. doi: 10.1038/nchembio.1339.
Pickett et al., Towards New Uses of Botulinum Toxin as a Novel Therapeutic Tool. Toxins. Jan. 2011;3:63-81.
Pogson et al., Engineering Next Generation Proteases. Curr Opin Biotechnol. Aug. 2009;20(4):390-7.
Putnam et al., Protein mimicry of DNA from crystal structures of the uracil-DNA glycosylase inhibitor protein and its complex with

(56) References Cited

OTHER PUBLICATIONS

*Escherichia coli* uracil-DNA glycosylase. J Mol Biol. Mar. 26, 1999;287(2):331-46. doi: 10.1006/jmbi.1999.2605.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Raingo et al., VAMP4 directs synaptic vesicles to a pool that selectively maintains asynchronous neurotransmission. Nat Neurosci. Mar. 11, 2012;15(5):738-45. doi: 10.1038/nn.3067.

Rossetto et al., Botulinum neurotoxins: genetic, structural and mechanistic insights. Nat Rev Microbiol. Aug. 2014;12(8):535-49. doi: 10.1038/nrmicro3295. Epub Jun. 30, 2014.

Ruiz-Martinez et al., YKT6 expression, exosome release, and survival in non-small cell lung cancer. Oncotarget. Aug. 9, 2016;7(32):51515-51524. doi: 10.18632/oncotarget.9862.

Sikorra et al., Substrate Recognition Mechanism of VAMP/Synaptobrevin-cleaving Clostridial Neurotoxins. Journal of Biological Chemistry. 2008;283:21145-52. Epub May 29, 2008.

Somm et al., A botulinum toxin—drived targeted secretion inihibitor downregulates the GH/IGF1 axis. The Journal of Clinical Investigation. Sep. 2012;122(9):3295-306.

Steffen et al., MT1-MMP-Dependent Invasion is Regulated by TI-VAMP/VAMP7. Current Biology. Jun. 2008;18:926-31.

Tsai et al., Targeting botulinum neurotoxin persistence by the ubiquitin-proteasome system. PNAS. Sep. 2010; 107(38):16554-9.

Turner et al., Structural plasticity of an aminoacyl-tRNA synthetase active site. Proc Natl Acad Sci U S A. Apr. 25, 2006;103(17):6483-8. doi: 10.1073/pnas.0601756103. Epub Apr. 17, 2006.
Umehara et al., N-acetyl lysyl-tRNA synthetases evolved by a CcdB-based selection possess N-acetyl lysine specificity in vitro and in vivo. FEBS Lett. Mar. 23, 2012;586(6):729-33. doi: 10.1016/j.febslet.2012.01.029. Epub Jan. 28, 2012.
Varadarajan et al., Engineering of protease variants exhibiting high catalytic activity and exquisite substrate selectivity. PNAS. May 2005;102(19):6855-60.
Varadarajan et al., Highly active and selective endopeptidases with programmed substrate specificities. Nat Chem Biol. May 2008;4(5):290-4.
Vincenzeti et al, Functional properties of subunit interactions in human cytidine deaminase. Protein Eng. Dec. 2003;16(12):1055-61. doi: 10.1093/protein/gzg117.
Vincenzeti et al., Possible role of two phenylalanine residues in the active site of human cytidine deaminase. Protein Eng. Nov. 2000;13(11):791-9. doi: 10.1093/protein/13.11.791.
Wang et al., Syntaxin Requirement for Ca2+-Triggered Exocytosis in Neurons and Endocrine Cells Demonstrated with an Engineered Neurotoxin. Boiochemistry. Apr. 2011;50(14):2711-3.
Williams et al., SNAP23, Syntaxin4, and vesicle-associated membrane protein 7 (VAMP7) mediate trafficking of membrane type 1-matrix metalloproteinase (MT1-MMP) during invadopodium formation and tumor cell invasion. MBoC. Jul. 2014;25:2061-70.
Yanagisawa et al., Crystallographic studies on multiple conformational states of active-site loops in pyrrolysyl-tRNA synthetase. J Mol Biol. May 2, 2008;378(3):634-52. doi: 10.1016/j.jmb.2008.02.045. Epub Feb. 29, 2008.
Yanagisawa et al., Multistep engineering of pyrrolysyl-tRNA synthetase to genetically encode N(epsilon)-(o-azidobenzyloxycarbonyl) lysine for site-specific protein modification. Chem Biol. Nov. 24, 2008;15(11):1187-97. doi: 10.1016/j.chembiol.2008.10.004.
Yeh et al., Retargeted Clostridial neurotoxins as Novel Agents for Treating Chronic Diseases. Biochemistry. Nov. 2011;50:10419-21.
Yi et al., Engineering of TEV protease variants by yeast ER sequestration screening (YESS) of combinatorial libraries. PNAS. Apr. 2013;110(18):7229-34.
Zhang et al., Identification and characterization of a novel botulinum neurotoxin. Nat Commun. Aug. 3, 2017;8:14130. doi: 10.1038/ncomms14130.
Ziemann et al., Gene name errors are widespread in the scientific literature. Genome Biol. Aug. 23, 2016;17(1):177. doi: 10.1186/s13059-016-1044-7.

* cited by examiner

Figure 39
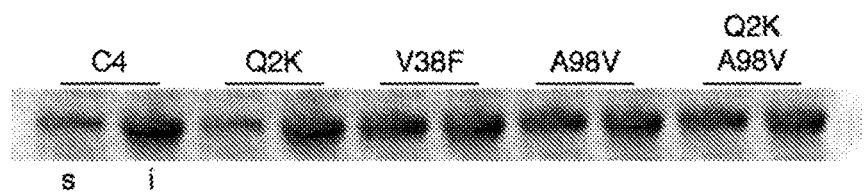
Figure 40
Figure 41
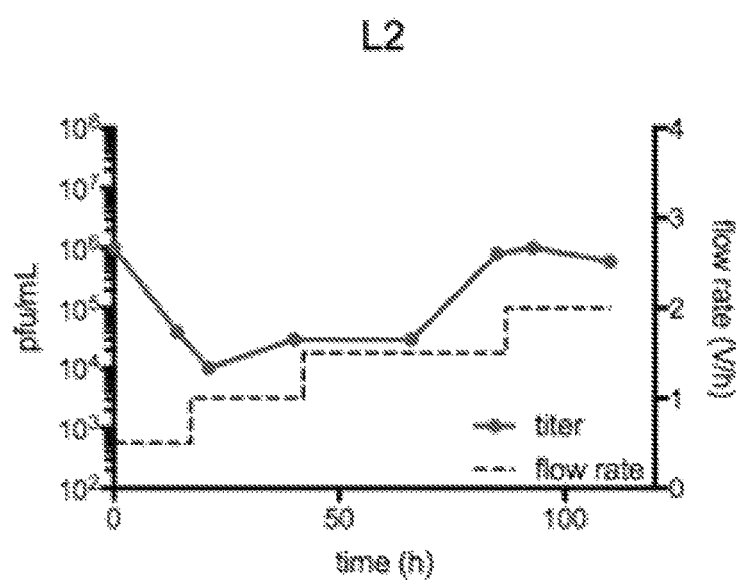

CONTINUOUS EVOLUTION FOR STABILIZED PROTEINS

RELATED APPLICATIONS

This application is a national stage filing under 35 U.S.C. § 371 of international PCT application, PCT/US2018/051557, filed Sep. 18, 2018, which claims the benefit under 35 U.S.C. 119(e) of the filing date of U.S. Provisional Application Ser. No. 62/559,919, filed Sep. 18, 2017, entitled "CONTINUOUS EVOLUTION FOR STABILIZED PROTEINS", the entire contents of each of which are incorporated herein by reference.

BACKGROUND

Proteins and nucleic acids employ only a small fraction of the available functionality. There is considerable current interest in modifying proteins and nucleic acids to diversify their functionality. Molecular evolution efforts include in vitro diversification of a starting molecule into related variants from which desired molecules are chosen. Methods used to generate diversity in nucleic acid and protein libraries include whole genome mutagenesis (Hart et al., Amer. Chem. Soc. (1999), 121:9887-9888), random cassette mutagenesis (Reidhaar-Olson et al., Meth. Enzymol. (1991), 208:564-86), error-prone PCR (Caldwell, et al. (1992), PCR Methods Applic. (1992), 2: 28-33), DNA shuffling using homologous recombination (Stemmer (1994) Nature (1994), 370:389-391), and phage-assisted continuous evolution (PACE). After diversification, molecules with novel or enhanced properties can be selected.

SUMMARY

Some aspects of this disclosure relate to systems, apparatuses, compositions (e.g., isolated nucleic acids and vectors), and methods for improving the stability and/or solubility of proteins evolved using PACE.

Phage-assisted continuous evolution (PACE) can serve as a rapid, high-throughput system for evolving genes of interest. One advantage of the PACE technology is that both the time and human effort required to evolve a gene of interest are dramatically decreased as compared to conventional iterative evolution methods. During PACE, a phage vector carrying a gene encoding a gene of interest replicates in a flow of host cells through a fixed-volume vessel (a "lagoon"). For example, in some embodiments of PACE described herein, a population of bacteriophage vectors replicates in a continuous flow of bacterial host cells through the lagoon, wherein the flow rate of the host cells is adjusted so that the average time a host cell remains in the lagoon is shorter than the average time required for host cell division, but longer than the average life cycle of the vector, e.g., shorter than the average M13 bacteriophage life cycle. As a result, the population of vectors replicating in the lagoon can be varied by inducing mutations, and then enriching the population for desired variants by applying selective pressure, while the host cells do not effectively replicate in the lagoon.

Often, proteins (e.g., engineered proteins, wild-type proteins, etc.) have certain physiochemical properties, such as decreased stability (e.g., thermostability) and/or solubility that render them unsuitable for therapeutic or commercial use. Some aspects of this disclosure provide systems for improving the stability and/or solubility of proteins evolved during PACE. The systems, including recombinant expression constructs, also referred to as vectors if they are in the form of a plasmid, described herein can enhance selection of evolved proteins that are properly folded, have increased stability (e.g., thermodynamic stability), and/or solubility (e.g., enhanced soluble expression in bacteria, such as *E. coli*) while maintaining desired protein function.

In some embodiments, the disclosure relates to isolated nucleic acids encoding expression constructs that enable stability-based and/or solubility-based selection of evolved proteins during PACE. In some embodiments, the disclosure relates to vectors, for example plasmids, comprising isolated nucleic acids described herein. The skilled artisan will appreciate that a vector as described herein can comprise one, or more than one (e.g., 2, 3, 4, 5, etc.), isolated nucleic acids (e.g., expression constructs) described by the disclosure. Typically, isolated nucleic acids and vectors described herein are contained within a host cell (e.g., a bacterial cell, such as an *E. coli* cell). A host cell may comprise one or more (e.g., 1, 2, 3, 4, 5, etc.) isolated nucleic acids as described herein and/or one or more vectors as described herein.

In some aspects, the disclosure relates to the use of the endogenous bacterial heat shock response for selection against unstable proteins during PACE. As described further in the Examples, accumulation of misfolded proteins in *E. coli* results in release of σ32 transcription factor and expression of heat shock proteins. However, by using promoters of certain *E. coli* sigma factors (e.g., σ32) to drive expression of a dominant-negative pIII protein (e.g., pIII-neg), expression constructs described herein allow for negative selection of misfolded proteins during PACE.

Accordingly, in some embodiments, the disclosure provides an isolated nucleic acid comprising an *E. coli* sigma 32 (σ32) promoter operably linked to a nucleic acid sequence that encodes a dominant negative gene III (pIII-neg). In some aspects, the σ32 promoter comprises a sequence encoding a protein as set forth in SEQ ID NO: 1.

Some aspects of this disclosure provide methods for directed evolution using an expression construct comprising an *E. coli* σ32 promoter. In some embodiments, the method comprises: contacting a population of bacterial host cells in a culture medium with a population of M13 phages comprising a gene of interest to be evolved and lacking a functional pIII gene required for the generation of infectious phage particles, wherein the M13 phages allow for expression of the gene of interest in the host cells, the host cells are suitable host cells for M13 phage infection, replication, and packaging, wherein the M13 phage comprises all phage genes required for the generation of phage particles, except a full-length pIII gene (e.g., a functional pIII protein); and the host cells comprise an expression construct encoding the pIII protein, wherein expression of the pIII gene is dependent on a function of a gene product of the gene of interest; incubating the population of host cells under conditions allowing for the mutation of the gene of interest, the production of infectious M13 phage, and the infection of host cells with M13 phage, wherein infected cells are removed from the population of host cells, and wherein the population of host cells is replenished with fresh host cells that are not infected by M13 phage, wherein the function of the gene of interest is a desired function, wherein desired functional library members induce production of pIII and release M13 progeny into the culture medium capable of infecting new host cells, wherein undesired non-functional library members do not produce pIII and release only non-infectious M13 progeny into the culture medium; and isolating a mutated M13 phage replication product encoding an evolved protein from the population of host cells, wherein the host cells comprise an expression construct encoding a dominant-negative pIII protein (pIII-neg) operably linked to an *E. coli* sigma 32 (σ32) promoter.

In some aspects, the disclosure relates to expression constructs engineered to couple expression of gIII protein to reconstitution of a split T7 RNA polymerase during PACE for selection of evolved proteins having increased stability and/or solubility (e.g., having increased stability and/or solubility relative to an unevolved protein). Without wishing to be bound by any particular theory, expression of a fusion protein comprising the T7 RNAP N-terminal domain in a cell expressing a T7 RNAP C-terminal domain and comprising a gene encoding a gIII protein operably linked to a T7 promoter results in reconstitution of a functional T7 RNAP and expression of the gIII protein. Accordingly, in some aspects, the disclosure provides an isolated nucleic acid comprising a sequence encoding a gene of interest to be evolved fused to a sequence encoding a T7 RNA polymerase (RNAP) N-terminal domain.

In some embodiments, sequence encoding a T7 RNAP N-terminal domain is contiguous with the 5'-end or the 3'-end of a sequence encoding a gene of interest to be evolved. In some embodiments, T7 RNAP N-terminal domain is represented by (or encodes a protein having) the sequence set forth in SEQ ID NO: 2 or 10. In some embodiments, a T7 RNAP C-terminal domain comprises (or encodes a protein having) the sequence set forth in SEQ ID NO: 3.

Some aspects of this disclosure provide methods for directed evolution using an expression construct comprising a gene of interest to be evolved fused to a sequence encoding a T7 RNA polymerase (RNAP) N-terminal domain. In some embodiments, the method comprises contacting a population of bacterial host cells expressing a T7 RNAP C-terminal domain with a population of M13 phages comprising a gene of interest to be evolved fused to a T7 RNAP N-terminal domain, wherein the M13 phages are deficient in a full-length pIII gene (e.g., a functional pIII protein), wherein the phage allows for expression of the gene of interest in the host cells, the host cells are suitable host cells for M13 phage infection, replication, and packaging; and the host cells comprise an expression construct encoding the pIII protein operably linked to a T7 promoter, wherein expression of the pIII gene is dependent on reconstitution of the T7 RNAP N-terminus and T7 RNAP C-terminus; incubating the population of host cells under conditions allowing for the mutation of the gene of interest, the production of infectious M13 phage, and the infection of host cells with M13 phage, wherein infected cells are removed from the population of host cells, and wherein the population of host cells is replenished with fresh host cells that are not infected by M13 phage; and isolating a mutated M13 phage replication product encoding an evolved protein from the population of host cells.

In some aspects, the disclosure relates to engineering of expression constructs comprising Nostoc punctiforme (Npu) split intein for simultaneous selection of protein function and solubility during PACE. As described further in the Examples, a PACE selection system comprising 1) an expression construct comprising a portion of gIII protein signal peptide fused to a Npu split intein fragment; and 2) an expression construct comprising a portion of gIII protein signal peptide (e.g., the remainder of the gIII signal peptide missing from the expression construct described in (1)) fused to a Npu split intein fragment complementary to the Npu split intein fragment described in (1), allows for selection of evolved proteins based upon the activity, stability (e.g., thermostability) and/or solubility of the protein of interest.

Accordingly, in some embodiments the disclosure provides an isolated nucleic acid comprising a sequence encoding a T7 promoter operably linked to an expression cassette comprising, in the following order: a sequence encoding a Npu split intein C-terminal portion, and a sequence encoding a M13 phage gIII protein, wherein the sequence encoding the gIII protein lacks one or more nucleic acid bases in the signal peptide domain.

In some embodiments, a sequence encoding a gIII protein lacks nucleic acid bases 1-10 of a signal peptide domain. In some embodiments, an isolated nucleic acid comprises a sequence encoding a protein comprising a sequence as set forth in SEQ ID NO: 4.

In some aspects, the disclosure provides isolated nucleic acid comprising a sequence encoding a RNA polymerase I promoter operably linked to an expression cassette comprising, in the following order, a sequence encoding a M13 phage gIII protein signal peptide; and a sequence encoding a Npu split intein N-terminal portion, wherein the sequence encoding the gIII protein signal peptide lacks one or more nucleic acid bases of the signal peptide domain (e.g., nucleic acid bases 1-10 of a gIII protein signal peptide, such as the sequence as set forth in SEQ ID NO: 5).

In some embodiments, an isolated nucleic acid further comprises a sequence encoding a repressor protein binding site. In some embodiments, a repressor protein is a lambda phage repressor protein, such as 434cI.

In some aspects, the disclosure provides a method of phage-assisted continuous evolution (PACE) comprising contacting a population of bacterial host cells with a population of M13 phages comprising a gene of interest to be evolved fused to a T7 RNAP, a RNAP omega subunit (rpoZ), and a HA4 monobody, wherein the M13 phages are deficient in a full-length pIII gene, wherein the phage allows for expression of the gene of interest in the host cells, the host cells are suitable host cells for M13 phage infection, replication, and packaging; and the host cells comprise an expression construct encoding one or more isolated nucleic acids comprising a Npu split intein, wherein expression of the pIII gene is dependent on reconstitution of Npu split intein N- and C-terminal portions; incubating the population of host cells under conditions allowing for the mutation of the gene of interest, the production of infectious M13 phage, and the infection of host cells with M13 phage, wherein infected cells are removed from the population of host cells, and wherein the population of host cells is replenished with fresh host cells that are not infected by M13 phage; and isolating a mutated M13 phage replication product encoding an evolved protein from the population of host cells.

In some aspects, the disclosure relates to compositions and methods for non-fusion-based solubility selection during PACE. Without wishing to be bound by any particular theory, fusion of small inclusion body chaperone proteins (e.g., ibpA, ibpB) to expression constructs comprising a split T7 RNAP fragment allows for sequestration of misfolded or insoluble proteins within host cells (e.g., *E. coli* cells). Thus, in some embodiments, the disclosure provides an isolated nucleic acid comprising a heat shock chaperone protein fused to a T7 RNAP N-terminal domain. In some embodiments, a heat shock chaperone protein is ibpA or ibpB. In some embodiments, a nucleic acid comprising a hear shock chaperone protein comprises (or encodes a protein having) the sequence set forth in SEQ ID NO: 6 or 7.

In some aspects, the disclosure relates to expression constructs comprising a GNC4 tag for solubility-based selection during PACE. As described further in the Examples, a GCN4 tag is used to allow solubility-based selection of proteins in PACE independent of protein activity. This involves fusion of the leucine zipper domain of the yeast GCN4 transcription factor ("GCN4 tag") upstream of the protein of interest and running dual PACE selections with an protein binding accessory plasmid (AP) encoding the anti-GCN4 scFv m3, which recognizes the GCN4 tag. In some embodiments, the disclosure provides an isolated nucleic acid comprising a sequence encoding a GCN4 tag, a gene encoding a protein of interest to be evolved, a T7 RNAP, and a RNAP omega subunit (rpoZ).

The skilled artisan will recognize that an isolated nucleic acid as described herein can be situated on a vector. In some embodiments, a vector is a plasmid. In some embodiments, more than one isolated nucleic acid as described herein is situated on a plasmid. For example, in some embodiments, a plasmid comprises 1, 2, 3, 4, 5 or more nucleic acids as described by the disclosure.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF DRAWINGS

FIG. 6A shows luminescence assay data indicating that Voigt T7 RNAP fused to MBP drives increased transcriptional activity relative to Voigt T7 RNAP fused to MalE31. FIG. 6B shows luminescence assay data indicating that Split T7 RNAP fused to MBP drives increased transcriptional activity relative to Split T7 RNAP fused to MalE31. aTc=anhydrotetracycline.

FIG. 7A shows ΔΔG (kcal/mol) of proteins in a Voigt T7 RNAP selection system. FIG. 7B shows ΔΔG (kcal/mol) of proteins in a Split T7 RNAP selection system.

FIG. 8A shows luminescence assay data indicating that the Voigt T7 RNAP selection system enriches stabilized Colicin immunity protein (Im7). FIG. 8B shows luminescence assay data indicating that the Split T7 RNAP selection system enriches stabilized Im7.

FIG. 10A shows a PACE lagoon with SP encoding MalE31 began recovering after ~60 hours. FIG. 10B shows a PACE lagoon with SP encoding MalE31 that washed out.

FIG. 16A shows an analytical gel indicating MBP variant expression in the soluble fraction of cell lysates. FIG. 16B shows data showing ΔΔG (kcal/mol) of MBP variants.

FIG. 17A shows luminescence data for PACE of MBP and MalE31 using T7 RNAP variants that have reduced transcriptional activity. FIG. 17B shows the ratio of MBP to MalE31 resulting from PACE using T7 RNAP variants that have reduced transcriptional activity.

FIG. 24A is a schematic overview of a split Npu intein selection system for PACE of HA4 monobody. FIG. 24B shows the number of plaque-forming units (pfu) in a PACE lagoon (L1) using a 20 ng/mL aTc drift. FIG. 24C shows the number of plaque-forming units (pfu) in a PACE lagoon (L2) using a 100 ng/mL aTc drift.

FIG. 25A shows fold propagation of scFv variants L34Ser, Ωgraft, and m3 during PACE with a 2-hybrid (e.g., split Npu intein) AP. FIG. 25B shows fold propagation of scFv variants L34Ser, Ωgraft, and m3 during PACE with a T7 mutant AP. FIG. 25C shows fold propagation of scFv variants L34Ser, Ωgraft, and m3 during PACE with both a 2-hybrid (e.g., split Npu intein)/mutant T7 combination AP.

FIG. 26A shows luminescence assay data for PACE of MBP and MalE31 using an AP encoding T7 C-terminus driven by $P_{BAD}$, a plasmid encoding ibpA fused to T7 RNAP N-terminus driven by $P_{TET}$, and a plasmid encoding MBP or MalE31 driven by $P_{BAD}$. FIG. 26B shows luminescence assay data for PACE of MBP and MalE31 using an AP encoding T7 C-terminus driven by $P_{BAD}$, a plasmid encoding ibpB fused to T7 RNAP N-terminus driven by $P_{TET}$, and a plasmid encoding MBP or MalE31 driven by $P_{BAD}$.

FIG. 27A shows fold propagation of scFv variants L34Ser, Ωgraft, and m3 during PACE with a 2-hybrid (e.g., split Npu intein) AP. FIG. 27B shows fold propagation of scFv variants L34Ser, Ωgraft, and m3 during PACE with a T7 mutant AP. FIG. 27C shows fold propagation of scFv variants L34Ser, Ωgraft, and m3 during PACE with both a 2-hybrid (e.g., split Npu intein)/mutant T7 combination AP.

FIG. 30 shows a Western blot indicating Ωgraft scFv variants evolved by split Npu intein PACE have increased solubility compared to wt Ωgraft scFv.

FIG. 31A shows PACE of MalE31 starting clone P33T/T275I. FIG. 31B shows PACE of MalE321 starting clone P33S/A386E. Both starting clones also have a G32D double mutation.

FIG. 38A shows representative data for plaque-forming units (pfus) in Lagoon 1 (L1). FIG. 38B shows representative data for plaque-forming units (pfus) in Lagoon 2 (L2). FIG. 38C shows representative data for plaque-forming units (pfus) in Lagoon 3 (L3).

FIG. 39 shows a Western blot indicating evolved Htt scFv clones have improved solubility relative to starting clone C4.

FIG. 40 shows a schematic overview of a selection plasmid comprising a "GCN4 tag" (e.g., the yeast transcription factor GCN4 leucine zipper sequence), a protein of interest (POI), T7n (T7 RNAP N-terminal domain), and RNA polymerase Z (rpoZ).

FIG. 41 shows representative data for plaque-forming units (pfus) of MalE31 variants using a SP comprising a "GCN4 tag" from a PACE lagoon, L2.

DEFINITIONS

Figure 1A:
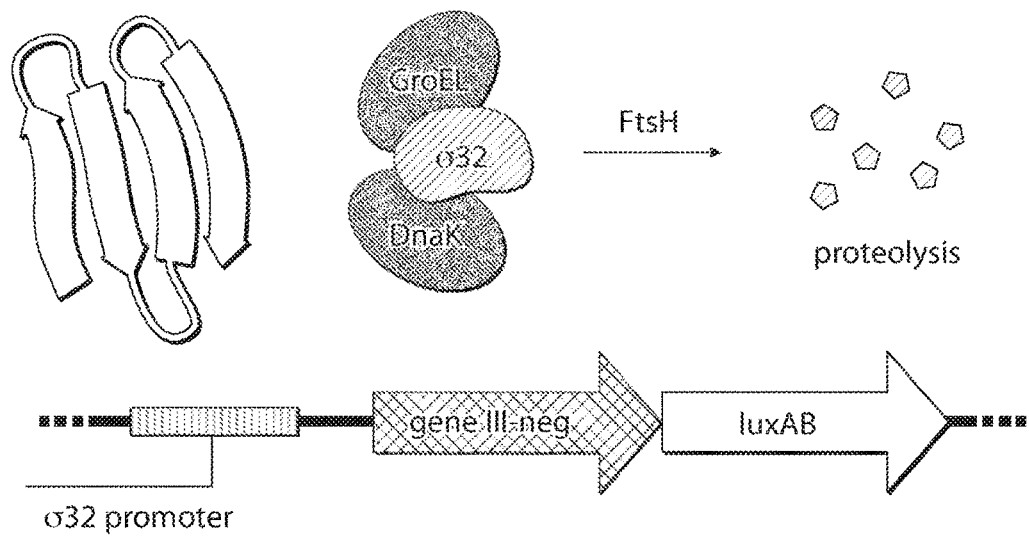
FIGS. 1A-1B are schematic overviews of a PACE negative selection strategy against unstable proteins using an *E. coli* σ32 reporter system.

The term "phage-assisted continuous evolution (PACE)," as used herein, refers to continuous evolution that employs phage as viral vectors. The general concept of PACE technology has been described, for example, in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; U.S. application, U.S. Ser. No. 13/922,812, filed Jun. 20, 2013; U.S. application, U.S. Ser. No. 62/067,194, filed Oct. 22, 2014, and U.S. Pat. No. 9,023,594, issued May 5, 2015, the entire contents of each of which are incorporated herein by reference.

The term "continuous evolution," as used herein, refers to an evolution process, in which a population of nucleic acids encoding a gene to be evolved is subjected to multiple rounds of (a) replication, (b) mutation, and (c) selection to produce a desired evolved version of the gene to be evolved that is different from the original version of the gene, for example, in that a gene product, such as, e.g., an RNA or protein encoded by the gene, exhibits a new activity not present in the original version of the gene product, or in that an activity of a gene product encoded by the original gene to be evolved is modulated (increased or decreased). The multiple rounds can be performed without investigator intervention, and the steps (a)-(c) can be carried out simultaneously. Typically, the evolution procedure is carried out in vitro, for example, using cells in culture as host cells. In general, a continuous evolution process provided herein relies on a system in which a gene encoding a gene product of interest is provided in a nucleic acid vector that undergoes a life-cycle including replication in a host cell and transfer to another host cell, wherein a critical component of the life-cycle is deactivated and reactivation of the component is dependent upon an activity of the gene to be evolved that is a result of a mutation in the nucleic acid vector.

The term "vector," as used herein, refers to a nucleic acid that can be modified to encode a gene of interest and that is able to enter into a host cell, mutate and replicate within the host cell, and then transfer a replicated form of the vector into another host cell. Exemplary suitable vectors include viral vectors, such as retroviral vectors or bacteriophages, and conjugative plasmids. Additional suitable vectors will be apparent to those of skill in the art based on the instant disclosure.

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene of interest to be evolved.

The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ (Lysogen), T2, T4, T7, T12, R17, M13, MS2, G4, Pl, P2, P4, Phi X174, N4, Φ6, and Φ29. In certain embodiments, the phage utilized in the present invention is M13. Additional suitable phages and host cells will be apparent to those of skill in the art and the invention is not limited in this aspect. For an exemplary description of additional suitable phages and host cells, see Elizabeth Kutter and Alexander Sulakvelidze: *Bacteriophages: Biology and Applications.* CRC Press; 1$^{st}$ edition (December 2004), ISBN: 0849313368; Martha R. J. Clokie and Andrew M. Kropinski: *Bacteriophages: Methods and Protocols, Volume 1: Isolation, Characterization, and Interactions (Methods in Molecular Biology)* Humana Press; 1$^{st}$ edition (December, 2008), ISBN: 1588296822; Martha R. J. Clokie and Andrew M. Kropinski: *Bacteriophages: Methods and Protocols, Volume 2: Molecular and Applied Aspects (Methods in Molecular Biology)* Humana Press; 1$^{st}$ edition (December 2008), ISBN: 1603275649; all of which are incorporated herein in their entirety by reference for disclosure of suitable phages and host cells as well as methods and protocols for isolation, culture, and manipulation of such phages).

The term "accessory plasmid," as used herein, refers to a plasmid comprising a gene required for the generation of infectious viral particles under the control of a conditional promoter. In the context of continuous evolution of genes, transcription from the conditional promoter of the accessory plasmid is typically activated, directly or indirectly, by a function of the gene to be evolved. Accordingly, the accessory plasmid serves the function of conveying a competitive advantage to those viral vectors in a given population of viral vectors that carry a version of the gene to be evolved able to activate the conditional promoter or able to activate the conditional promoter more strongly than other versions of the gene to be evolved. In some embodiments, only viral vectors carrying an "activating" version of the gene to be evolved will be able to induce expression of the gene required to generate infectious viral particles in the host cell, and, thus, allow for packaging and propagation of the viral genome in the flow of host cells. Vectors carrying non-activating versions of the gene to be evolved, on the other hand, will not induce expression of the gene required to generate infectious viral vectors, and, thus, will not be packaged into viral particles that can infect fresh host cells.

The term "helper phage," as used herein interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes for the generation of infectious phage particles. Helper phages are useful to allow modified phages that lack a gene for the generation of infectious phage particles to complete the phage life cycle in a host cell. Typically, a helper phage will comprise the genes for the generation of infectious phage particles that are lacking in the phage genome, thus complementing the phage genome. In the continuous evolution context, the helper phage typically complements the selection phage, but both lack a phage gene required for the production of infectious phage particles.

The term "selection phage," as used herein interchangeably with the term "selection plasmid," refers to a modified phage that comprises a gene of interest to be evolved and lacks a full-length gene encoding a protein required for the generation of infectious phage particles. For example, some M13 selection phages provided herein comprise a nucleic acid sequence encoding a gene to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a gene to be evolved, e.g., under the control of an M13 promoter, and lack all or part of a gene encoding a protein required for the generation of infective phage particles, e.g., the gIII gene encoding the pIII protein.

The term "mutagenesis plasmid," as used herein, refers to a plasmid comprising a gene encoding a gene product that acts as a mutagen. In some embodiments, the gene encodes a DNA polymerase lacking a proofreading capability. In some embodiments, the gene is a gene involved in the bacterial SOS stress response, for example, a UmuC, UmuD', or RecA gene. In some embodiments, the gene is a GATC methylase gene, for example, a deoxyadenosine methylase (dam methylase) gene. In some embodiments, the gene is involved in binding of hemimethylated GATC sequences, for example, a seqA gene. In some embodiments, the gene is involved with repression of mutagenic nucleobase export, for example emrR. In some embodiments, the gene is involved with inhibition of uracil DNA-glycosylase, for example a Uracil Glycosylase Inhibitor (ugi) gene. In some embodiments, the gene is involved with deamination of cytidine (e.g., a cytidine deaminase from *Petromyzon*

*marinus*), for example, cytidine deaminase 1 (CDA1). Mutagenesis plasmids (also referred to as mutagenesis constructs) are described, for example by International Patent Application, PCT/US2016/027795, filed Apr. 16, 2016, published as WO2016/168631 on Oct. 20, 2016, the entire contents of which are incorporated herein by reference.

The term "nucleic acid," as used herein, refers to a polymer of nucleotides. The polymer may include natural nucleosides (i.e., adenosine, thymidine, guano sine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term "protein," as used herein refers to a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain; see, for example, cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "gene of interest" or "gene to be evolved," as used herein, refers to a nucleic acid construct comprising a nucleotide sequence encoding a gene product, e.g., an RNA or a protein, to be evolved in a continuous evolution process as provided herein. The term includes any variations of a gene of interest that are the result of a continuous evolution process according to methods provided herein. For example, in some embodiments, a gene of interest is a nucleic acid construct comprising a nucleotide sequence encoding an RNA or protein to be evolved, cloned into a viral vector, for example, a phage genome, so that the expression of the encoding sequence is under the control of one or more promoters in the viral genome. In other embodiments, a gene of interest is a nucleic acid construct comprising a nucleotide sequence encoding an RNA or protein to be evolved and a promoter operably linked to the encoding sequence. When cloned into a viral vector, for example, a phage genome, the expression of the encoding sequence of such genes of interest is under the control of the heterologous promoter and, in some embodiments, may also be influenced by one or more promoters comprised in the viral genome. In some embodiments, the term "gene of interest" or "gene to be evolved refers to a nucleic acid sequence encoding a gene product to be evolved, without any additional sequences. In some embodiments, the term also embraces additional sequences associated with the encoding sequence, such as, for example, intron, promoter, enhancer, or polyadenylation signal sequences.

The term "evolved protein," as used herein, refers to a protein variant that is expressed by a gene of interest that has been subjected to continuous evolution, such as PACE.

The term "host cell," as used herein, refers to a cell that can host, replicate, and transfer a phage vector useful for a continuous evolution process as provided herein. In embodiments where the vector is a viral vector, a suitable host cell is a cell that can be infected by the viral vector, can replicate it, and can package it into viral particles that can infect fresh host cells. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the disclosure is not limited in this respect.

DETAILED DESCRIPTION

Aspects of the disclosure relate to compositions (e.g., isolated nucleic acids and vectors) and methods for improving the stability and/or solubility of proteins evolved using PACE. The disclosure is based, in part, on positive and negative selection systems that bias continuous evolution of a gene of interest towards production of evolved protein variants having desirable physiochemical characteristics, for example, increased solubility and/or stability (e.g., thermostability) relative to a gene product of the gene of interest, such as a gene product that has not been evolved (e.g., subjected to PACE). Without wishing to be bound by any particular theory, selection constructs and systems described herein generally function by linking a desired physiochemical characteristic or function of an evolved protein to expression of a gene required for the generation of infectious viral particles.

Selection System Constructs

Some aspects of this disclosure provide expression constructs encoding gene products that select for a desired physiochemical characteristic or desired function of an evolved protein in a host cell, e.g., in a bacterial host cell. In some embodiments, a selection system comprises one or more gene products encoded by a nucleic acid (e.g., an isolated nucleic acid). In some embodiments, one or more nucleic acids that are operably linked comprise an expression construct. Expression constructs are sometimes also referred to as vectors. In some embodiments, the expression constructs are plasmids.

In some embodiments, the plasmid comprises a bacterial origin of replication. In some embodiments, the origin of replication is a cloDF13 origin of replication. In some embodiments, the plasmid comprises a nucleic acid sequence encoding a gene product conferring resistance to an antibiotic to a bacterial host cell. In some embodiments, the antibiotic is chloramphenicol, kanamycin, tetracycline, or ampicillin.

A selection system can be a positive selection system, a negative selection system or a combination of one or more positive selection systems (e.g., 1, 2, 3, 4, 5, or more positive selection systems) and one or more negative selection systems (e.g., 1, 2, 3, 4, 5, or more negative selection systems). In some embodiments, a positive selection system links production (e.g., translation and/or function) of an evolved protein having a desired physiochemical characteristic (e.g., solubility, stability, etc.) and/or a desired function to expression of a gene required for production of infectious phage particles. In some embodiments, a negative selection system links production (e.g., translation and/or function) of an evolved protein having an undesired physiochemical characteristic (e.g., reduced solubility, reduced stability, etc.) and/or an undesired function to expression of a gene that prevents production of infectious phage particles (e.g., dominant negative pIII protein, such as pIII-neg). In the context of PACE, suitable negative selection strategies and reagents are described herein and in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; U.S. application, U.S. Ser. No. 13/922,812, filed Jun. 20, 2013; and U.S. application, U.S. Ser. No. 62/067,194, filed Oct. 22, 2014, the entire contents of each of which are incorporated herein by reference.

In some aspects, the disclosure relates to expression vectors (e.g., plasmids) comprising bacterial heat shock response regulatory element operably linked to a PACE negative selection system. In some embodiments, the expression vector is an accessory plasmid. Without wishing to be bound by any particular theory, expression of misfolded proteins in a PACE system comprising such a construct results in induction of the bacterial heat shock response, which in turn activates expression of the negative selection system. Examples of proteins involved in the bacterial heat shock response include but are not limited to sigma 32 (σ32), Heat Shock Protein 90 (HSP90), Heat Shock Protein 70 (HSP 70), DnaK, GroEL, etc. Examples of bacterial heat shock response regulatory elements include but are not limited to promoters, transcription factors, miRNA binding sites, etc. In some embodiments, the bacterial heat shock response regulatory element is a bacterial heat shock protein promoter. In some embodiments, the bacterial heat shock protein promoter is an *E. coli* sigma 32 (σ32) promoter. In some aspects, the σ32 promoter comprises a sequence set forth in SEQ ID NO: 1. However, the skilled artisan will appreciate that bacterial species from which the heat shock response regulatory elements are derived will depend upon the bacterial species into which PACE will be carried out.

In some embodiments, the bacterial heat shock protein regulatory element (e.g., promoter) is operably linked to a nucleic acid sequence that encodes a negative selection system. In some embodiments, the negative selection system is a nucleic acid (e.g. expression construct) that encodes a dominant negative gene III (pIII-neg), for example a pIII variant that comprises the two N-terminal domains of pIII and a truncated, termination-incompetent C-terminal domain is not only inactive but is a dominant-negative variant of pIII. A pIII variant comprising the two N-terminal domains of pIII and a truncated, termination-incompetent C-terminal domain was described in Bennett, N. J.; Rakonjac, J., Unlocking of the filamentous bacteriophage virion during infection is mediated by the C domain of pIII. *Journal of Molecular Biology* 2006, 356 (2), 266-73; the entire contents of which are incorporated herein by reference. In some embodiments, a pIII-neg variant as provided herein is efficiently incorporated into phage particles, but it does not catalyze the unlocking of the particle for entry during infection, rendering the respective phage noninfectious even if wild type pIII is present in the same phage particle. Accordingly, such pIII-neg variants are useful for devising a negative selection strategy in the context of PACE, for example, by providing an expression construct comprising a nucleic acid sequence encoding a pIII-neg variant under the control of a promoter comprising a recognition motif, the recognition of which is undesired (e.g., an *E. coli* σ32 promoter).

In some aspects, the disclosure relates to expression vectors (e.g., plasmids) comprising a gene of interest to be evolved fused to a sequence encoding a T7 RNA polymerase (RNAP) N-terminal domain. In some embodiments, the plasmid is a selection plasmid (e.g., selection phagemid). In some embodiments, the expression construct comprises a nucleic acid encoding the gene of interest is contiguous (e.g., operably linked) to the nucleic acid sequence encoding the T7 RNAP N-terminal domain. In some embodiments, the 3'-end of the nucleic acid encoding the gene of interest is contiguous (e.g., operably linked) to the 5'-end of the nucleic acid encoding the T7 RNAP N-terminal domain. In some embodiments, the expression construct further comprises a promoter, such as a $P_{BAD}$ promoter.

An N-terminal domain of a T7 RNAP may comprise between about 1% and about 99% (e.g., any percentage between 1% and 99%), about 10% and about 80%, or about 30% and about 60% of the amino acid residues of a full-length T7 RNAP (e.g., about 1% to about 99% of the amino acid residues of NCBI Accession No. NC_041960.1). In some embodiments, a T7 RNAP N-terminal domain comprises between 1 and 800 amino acid (e.g., any integer between 1 and 800, inclusive) truncations relative to the C-terminus of wild-type T7 RNAP (e.g., NCBI Accession No. NC_041960.1). For example, in some embodiments, an N-terminal domain of T7 RNAP comprises amino acid residues 1-50, 1-100, 1-150, 1-300, 1-400, 1-500, or 1-800 of NCBI Accession No. NC_041960.1.

In some aspects, the disclosure relates to expression vectors (e.g., plasmids) comprising an isolated nucleic acid having a sequence encoding a T7 RNA polymerase (RNAP) C-terminal domain. In some embodiments, the expression vector (e.g., plasmid) is an accessory plasmid. Without wishing to be bound by any particular theory, expression of a C-terminal domain of T7 RNAP in a cell (e.g., a host cell) in which a properly-folded fusion protein (e.g., comprising a gene of interest fused to a T7 RNAP N-terminal domain) is expressed, results in reconstitution of a functional T7 RNAP. A C-terminal domain of a T7 RNAP may comprise between about 1% and about 99% (e.g., any percentage between 1% and 99%), about 10% and about 80%, or about 30% and about 60% of the amino acid residues of a full-length T7 RNAP (e.g., about 1% to about 99% of the amino acid residues of NCBI Accession No. NC_041960.1). In some embodiments, a T7 RNAP C-terminal domain comprises between 1 and 800 amino acid (e.g., any integer between 1 and 800, inclusive) truncations relative to the N-terminus of wild-type T7 RNAP (e.g., NCBI Accession No. NC_041960.1). For example, in some embodiments, an N-terminal domain of T7 RNAP comprises amino acid residues 50-883, 100-883, 200-883, 400-884, or 500-883 of NCBI Accession No. NC_041960.1.

In some aspects, the disclosure relates to expression vectors (e.g., plasmids) comprising a gene of interest to be evolved fused to a sequence encoding a T7 RNA polymerase (RNAP) N-terminal domain further comprises a nucleic acid encoding a split intein portion (e.g., fragment). An "intein" refers to a protein that is able to self-catalytically excise itself and join the remaining protein fragments (e.g., exteins) by the process of protein splicing. Generally, the self-splicing function of inteins makes them useful tools for engineering trans-spliced recombinant proteins, as described in U.S. Publication No. 2003-0167533, the entire contents of which are incorporated herein by reference. For example, expressing (i) a nucleic acid sequence encoding a N-terminal intein fragment (or portion) operably linked to a nucleic acid encoding a first protein fragment (A) and (ii) a nucleic acid encoding a C-terminal intein fragment (or portion) operably linked to a nucleic acid encoding a second protein fragment (B), in a cell would result, in some embodiments, in trans-splicing of the inteins within the cell to produce a fusion molecule comprising (in the following order) "A-B".

Inteins are present in both prokaryotic and eukaryotic organisms. In some embodiments, an intein is a bacterial intein, such as a cyanobacterial intein (e.g., intein from Synechocystis or Nostoc). In some embodiments, the intein is a Nostoc punctiforme (Npu) intein, for example as described in Oeemig et al. (2009) *FEBS Lett.* 583(9):1451-6.

In some embodiments, an expression construct described herein comprises a nucleic acid encoding a split intein portion (e.g., a split intein N-terminal portion or split intein C-terminal portion) operably linked to a nucleic acid encoding a gene required for the production of infectious phage particles, such as gIII protein (pIII protein), or a portion (e.g., fragment) thereof. In some embodiments, the split intein portion is a split intein C-terminal portion (e.g., a Npu split intein C-terminal portion). In some embodiments, the split intein C-terminal portion is positioned upstream of (e.g., 5' relative to) the nucleic acid encoding the gene required for the production of infectious phage particles, or portion thereof. In some embodiments, the split intein portion is a split intein N-terminal portion (e.g., a Npu split intein N-terminal portion). In some embodiments, the split intein N-terminal portion is positioned downstream of (e.g., 3' relative to) the nucleic acid encoding the gene required for the production of infectious phage particles, or portion thereof.

In some embodiments, the nucleic acid encoding a gene required for the production of infectious phage particles, such as gIII protein (pIII protein), is truncated (e.g., missing one or more nucleic acid bases relative to a full-length gene encoding pIII protein). In some embodiments, the nucleic acid is 1, 2, 3, 4, 5, 6, 7, 8, 9, 10, or more nucleic acid bases shorter than a full-length gene encoding pIII protein. It should be appreciated that the nucleic acid encoding truncated pIII protein may be truncated at either the 5'-end or the 3'-end. However, in preferred embodiments, the nucleic acid is truncated at the 5'-end. In some embodiments, the gene product encoded by the truncated nucleic acid lacks a full-length N-terminal signal peptide. In some embodiments, the gene product lacks amino acid residues 1-10 of a gIII protein signal peptide. In some embodiments, the gene product lacks amino acid residues 1-11, 1-12, 1-13, 1-14, 1-15, 1-16, 1-17, or 1-18 (e.g., the entire signal peptide) of pIII. In some embodiments, a portion of a pIII protein comprises the sequence set forth in SEQ ID NO: 8 (MKKLLPAIP). In some embodiments, a portion of a pIII protein comprises the sequence set forth in SEQ ID NO: 9.

In some embodiments, expression constructs (e.g., plasmids), or combinations of expression constructs (e.g. combinations of plasmids) described herein may be used as a bacterial 2-hybrid system to positively select for evolved proteins having desirable physiochemical characteristics (e.g., solubility, stability, etc.) or desirable function. In the context of PACE, bacterial 2-hybrid selections have been described, for example in International PCT Application, PCT/US2016/043559, filed Jul. 22, 2016, published as WO 2017/015559 on Jan. 26, 2017, and Badran et al. (2016) *Nature* 533:58-63, the entire contents of each of which are incorporated herein by reference.

In some embodiments, a bacterial 2-hybrid system comprises a first expression construct comprising a nucleic acid encoding a split intein C-terminal portion fused (e.g., operably linked) to a gene encoding a truncated gIII as described herein, and a second expression construct comprising a nucleic acid encoding a split intein N-terminal portion fused (e.g., operably linked) to a gene encoding a truncated gIII, where expression of the first expression construct and the second expression construct in a cell results in reconstitution (e.g., protein splicing) of a full-length functional pIII protein. In some embodiments, the first expression construct is operably linked to a promoter, such as a T7 RNAP promoter. In some embodiments, the first expression construct or the second expression construct further comprises a nucleic acid encoding a phage repressor protein, for example 434 cI repressor protein. In some embodiments, the first expression construct or the second expression construct is encodes a fusion protein comprising 434 cI repressor protein and the SH2 domain of an ABL1 kinase.

The first expression construct and the second expression construct can be located on the same vector (e.g., plasmid) or on separate vectors (e.g., different plasmids). In some embodiments, the vector is an accessory plasmid (AP). In some embodiments, a bacterial 2-hybrid system comprises a third expression construct comprising a nucleic acid encoding a gene of interest to be evolved (e.g., a HA4 monobody), T7 RNAP N-terminal domain, and an RNA polymerase subunit. In some embodiments, the RNA polymerase is RNA polymerase subunit omega (RpoZ). In some embodiments, the first expression construct, second expression construct, or third expression construct comprises a nucleic acid encoding a T7 RNAP C-terminal domain.

In some aspects, the disclosure relates to selection systems (e.g. comprising one or more vectors, such as plasmids) comprising an isolated nucleic acid encoding a heat shock chaperone protein (e.g., a bacterial heat shock protein), or a portion thereof, fused to a T7 RNAP N-terminal domain. In some embodiments, a heat shock chaperone protein is ibpA or ibpB, which are known in the art to associate with inclusion bodies, for example as described by Laskowska et al. (1996) *Biochimie* 78(2):117-22. Without wishing to be bound by any particular theory, expression of misfolded proteins in during PACE will result in the induction of heat shock response in the host cell, thereby sequestering ibpA or ibpB proteins fused to T7 N-terminal domain and preventing expression in pIII. The net result of such sequestration will be selection for properly folded evolved proteins. In some embodiments, a vector (e.g., plasmid) comprising a bacterial heat shock protein (e.g., ibpA, ibpB, etc.) is an accessory plasmid.

In some aspects, the disclosure provides expression constructs (e.g., plasmids) comprising an isolated nucleic acid encoding a leucine zipper domain of the yeast GCN4 transcription factor ("GCN4 tag") fused upstream of the protein of interest to be evolved. In some embodiments the expression construct is a selection plasmid (SP). For example, using a split intein system described elsewhere in the disclosure, two simultaneous PACE selections are run: the first is a split T7 RNAP-based solubility selection, and the second is a protein binding selection with an accessory plasmid (AP) encoding the anti-GCN4 scFv m3, which recognizes the GCN4 tag. The T7 RNAP based solubility selection evolves for increased protein solubility, while the GCN4 tag protein binding selection prevents potential cheating in the same way as an activity-dependent selection. This greatly expands the scope of proteins compatible with the selection.

Some aspects of this invention provide a system for continuous evolution procedures, comprising of a viral vector, for example, a selection phage, comprising a multiple cloning site for insertion of a gene to be evolved, one or more additional accessory plasmids (e.g., comprising a selection system) as described herein, and, optionally, a mutagenesis expression construct. In some embodiments, a vector system for phage-based continuous directed evolution is provided that comprises (a) a selection phage comprising a multiple cloning site for insertion of a gene of interest to be evolved, wherein the phage genome is deficient in at least one gene required to generate infectious phage; (b) and at least one accessory plasmid comprising the at least one gene required to generate infectious phage particle under the control of a conditional promoter that is activated in response to a desired physiochemical characteristic (e.g., solubility, stability, etc.) and/or a desired activity of the gene to be evolved; and, optionally, (c) a mutagenesis expression construct as provided herein.

Some aspects of this disclosure provide a cell comprising an expression construct or a plasmid as provided herein. In some embodiments, the cell is a bacterial cell. In some embodiments, the cell further comprises a selection plasmid or an accessory plasmid. In some embodiments, the cell is a host cell for a bacteriophage. In some embodiments, the cell is an *E. coli* cell. In some embodiments, the cell is comprised in a lagoon.

Methods

In some aspects, the disclosure provides methods for directed evolution using one or more of the expression constructs described herein. In some embodiments, the method comprises (a) contacting a population of host cells comprising an expression construct or plasmid as provided herein with a population of phage vectors comprising a gene to be evolved and deficient in at least one gene for the generation of infectious phage particles, wherein (1) the host cells are amenable to transfer of the vector; (2) the vector allows for expression of the gene to be evolved in the host cell, can be replicated by the host cell, and the replicated vector can transfer into a second host cell; (3) the host cell expresses a gene product encoded by the at least one gene for the generation of infectious phage particles of (a) in response to a particular physiochemical characteristic (e.g., solubility, stability, etc.) and/or activity of the gene to be evolved, and the level of gene product expression depends on the physiochemical characteristic and/or activity of the gene to be evolved; (b) incubating the population of host cells under conditions allowing for selection of the gene to be evolved based upon the physiochemical characteristic and/or activity of the gene to be evolved and the transfer of the vector comprising the gene to be evolved from host cell to host cell, wherein host cells are removed from the host cell population, and the population of host cells is replenished with fresh host cells that comprise the expression construct but do not harbor the vector; and (c) isolating a replicated vector from the host cell population in (b), wherein the replicated vector comprises a mutated version of the gene to be evolved (e.g., an evolved protein).

In some embodiments, the expression construct comprises an inducible promoter, wherein the incubating of (b) comprises culturing the population of host cells under conditions suitable to induce expression from the inducible promoter. In some embodiments, the inducible promoter is an arabinose-inducible promoter, wherein the incubating of (b) comprises contacting the host cell with an amount of arabinose sufficient to increase expression of the arabinose-inducible promoter by at least 10-fold, at least 50-fold, at least 100-fold, at least 500-fold, at least 1000-fold, at least 5000-fold, at least 10000-fold, at least 50000-fold, at least 100000-fold, at least 500000-fold, or at least 1000000-fold as compared to basal expression in the absence of arabinose.

In some embodiments, the vector is a viral vector. In some embodiments, the viral vector is a phage. In some embodiments, the phage is a filamentous phage. In some embodiments, the phage is an M13 phage.

In some embodiments, the host cells comprise an accessory plasmid. In some embodiments, the accessory plasmid comprises an expression construct encoding the pIII protein under the control of a promoter that is activated by a gene product encoded by the gene to be evolved. In some embodiments, the host cells comprise the accessory plasmid and together, the helper phage and the accessory plasmid comprise all genes required for the generation of an infectious phage. In some embodiments, the method further comprises a negative selection for undesired activity of the gene to be evolved. In some embodiments, the host cells comprise an expression construct encoding a dominant-negative pIII protein (pIII-neg). In some embodiments, expression of the pIII-neg protein is driven by a promoter the activity of which depends on an undesired function of the gene to be evolved.

In some embodiments, step (b) comprises incubating the population of host cells for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive life cycles of the viral vector or phage. In some embodiments, the host cells are *E. coli* cells.

In some embodiments, the host cells are incubated in suspension culture. In some embodiments, the population of host cells is continuously replenished with fresh host cells that do not comprise the vector. In some embodiments, fresh cells are being replenished and cells are being removed from the cell population at a rate resulting in a substantially constant number of cells in the cell population. In some embodiments, fresh cells are being replenished and cells are being removed from the cell population at a rate resulting in a substantially constant vector population. In some embodiments, fresh cells are being replenished and cells are being removed from the cell population at a rate resulting in a substantially constant vector, viral, or phage load. In some embodiments, the rate of fresh cell replenishment and/or the rate of cell removal is adjusted based on quantifying the cells in the cell population. In some embodiments, the rate of fresh cell replenishment and/or the rate of cell removal is adjusted based on quantifying the frequency of host cells harboring the vector and/or of host cells not harboring the vector in the cell population. In some embodiments, the quantifying is by measuring the turbidity of the host cell culture, measuring the host cell density, measuring the wet weight of host cells per culture volume, or by measuring light extinction of the host cell culture.

In some embodiments, the host cells are exposed to a mutagen. In some embodiments, the mutagen is ionizing radiation, ultraviolet radiation, base analogs, deaminating agents (e.g., nitrous acid), intercalating agents (e.g., ethidium bromide), alkylating agents (e.g., ethylnitrosourea), transposons, bromine, azide salts, psoralen, benzene,3-Chloro-4-(dichloromethyl)-5-hydroxy-2(5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N -nitro-N-nitrosoguanidine (ENNG) (CAS no. 4245-77-6), N-methyl-N -nitro-N-nitrosoguanidine (MNNG) (CAS no. 70-25-7), 5-diazouracil (CAS no. 2435-76-9), or t-butyl hydroperoxide (BHP) (CAS no. 75-91-2).

In some embodiments, the vector or phage encoding the gene to be evolved is a filamentous phage, for example, an M13 phage, such as an M13 selection phage as described in more detail elsewhere herein. In some embodiments, the host cells are cells amenable to infection by the filamentous phage, e.g., by M13 phage, such as, for example, E. coli cells. In some such embodiments, the gene required for the production of infectious viral particles is the M13 gene III (gIII) encoding the M13 protein III (pIII).

Typically, the vector/host cell combination is chosen in which the life cycle of the vector is significantly shorter than the average time between cell divisions of the host cell. Average cell division times and vector life cycle times are well known in the art for many cell types and vectors, allowing those of skill in the art to ascertain such host cell/vector combinations. In certain embodiments, host cells are being removed from the population of host cells in which the vector replicates at a rate that results in the average time of a host cell remaining in the host cell population before being removed to be shorter than the average time between cell divisions of the host cells, but to be longer than the average life cycle of the viral vector employed. The result of this is that the host cells, on average, do not have sufficient time to proliferate during their time in the host cell population while the viral vectors do have sufficient time to infect a host cell, replicate in the host cell, and generate new viral particles during the time a host cell remains in the cell population. This assures that the only replicating nucleic acid in the host cell population is the vector encoding the gene to be evolved, and that the host cell genome, the accessory plasmid, or any other nucleic acid constructs cannot acquire mutations allowing for escape from the selective pressure imposed.

For example, in some embodiments, the average time a host cell remains in the host cell population is about 10, about 11, about 12, about 13, about 14, about 15, about 16, about 17, about 18, about 19, about 20, about 21, about 22, about 23, about 24, about 25, about 30, about 35, about 40, about 45, about 50, about 55, about 60, about 70, about 80, about 90, about 100, about 120, about 150, or about 180 minutes.

In some embodiments, the average time a host cell remains in the host cell population depends on how fast the host cells divide and how long infection (or conjugation) requires. In general, the flow rate should be faster than the average time required for cell division, but slow enough to allow viral (or conjugative) propagation. The former will vary, for example, with the media type, and can be delayed by adding cell division inhibitor antibiotics (FtsZ inhibitors in E. coli, etc.). Since the limiting step in continuous evolution is production of the protein required for gene transfer from cell to cell, the flow rate at which the vector washes out will depend on the current activity of the gene(s) of interest. In some embodiments, titrable production of the protein required for the generation of infectious particles, as described herein, can mitigate this problem. In some embodiments, an indicator of phage infection allows computer-controlled optimization of the flow rate for the current activity level in real-time.

In some embodiments, a PACE experiment according to methods provided herein is run for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive viral life cycles. In certain embodiments, the viral vector is an M13 phage, and the length of a single viral life cycle is about 10-20 minutes.

In some embodiments, the host cells are contacted with the vector and/or incubated in suspension culture. For example, in some embodiments, bacterial cells are incubated in suspension culture in liquid culture media. Suitable culture media for bacterial suspension culture will be apparent to those of skill in the art, and the invention is not limited in this regard. See, for example, *Molecular Cloning: A Laboratory Manual*, 2nd Ed., ed. by Sambrook, Fritsch, and Maniatis (Cold Spring Harbor Laboratory Press: 1989); Elizabeth Kutter and Alexander Sulakvelidze: *Bacteriophages: Biology and Applications*. CRC Press; 1$^{st}$ edition (December 2004), ISBN: 0849313368; Martha R. J. Clokie and Andrew M. Kropinski: *Bacteriophages: Methods and Protocols, Volume* 1: *Isolation, Characterization, and Interactions* (*Methods in Molecular Biology*) Humana Press; 1$^{st}$ edition (December, 2008), ISBN: 1588296822; Martha R. J. Clokie and Andrew M. Kropinski: *Bacteriophages: Methods and Protocols, Volume* 2: *Molecular and Applied Aspects* (*Methods in Molecular Biology*) Humana Press; 1$^{st}$ edition (December 2008), ISBN: 1603275649; all of which are incorporated herein in their entirety by reference for disclosure of suitable culture media for bacterial host cell culture).

Suspension culture typically requires the culture media to be agitated, either continuously or intermittently. This is achieved, in some embodiments, by agitating or stirring the vessel comprising the host cell population. In some embodiments, the outflow of host cells and the inflow of fresh host cells is sufficient to maintain the host cells in suspension. This in particular, if the flow rate of cells into and/or out of the lagoon is high.

In some embodiments, the flow of cells through the lagoon is regulated to result in an essentially constant number of host cells within the lagoon. In some embodiments, the flow of cells through the lagoon is regulated to result in an essentially constant number of fresh host cells within the lagoon. Typically, the lagoon will hold host cells in liquid media, for example, cells in suspension in a culture media. However, lagoons in which adherent host cells are cultured on a solid support, such as on beads, membranes, or appropriate cell culture surfaces are also envisioned. The lagoon may comprise additional features, such as a stirrer or agitator for stirring or agitating the culture media, a cell densitometer for measuring cell density in the lagoon, one or more pumps for pumping fresh host cells into the culture vessel and/or for removing host cells from the culture vessel, a thermometer and/or thermocontroller for adjusting the culture temperature, as well as sensors for measuring pH, osmolarity, oxygenation, and other parameters of the culture media. The lagoon may also comprise an inflow connected to a holding vessel comprising a mutagen or a transcriptional inducer of a conditional gene expression system, such as the arabinose-inducible expression system of the mutagenesis plasmid described in more detail elsewhere herein.

In some embodiments, the host cell population is continuously replenished with fresh, uninfected host cells. In some embodiments, this is accomplished by a steady stream of fresh host cells into the population of host cells. In other embodiments, however, the inflow of fresh host cells into the lagoon is semi-continuous or intermittent (e.g., batch-fed). In some embodiments, the rate of fresh host cell inflow into the cell population is such that the rate of removal of cells from the host cell population is compensated. In some embodiments, the result of this cell flow compensation is that the number of cells in the cell population is substantially constant over the time of the continuous evolution procedure. In some embodiments, the portion of fresh, uninfected cells in the cell population is substantially constant over the time of the continuous evolution procedure. For example, in some embodiments, about 10%, about 15%, about 20%, about 25%, about 30%, about 40%, about 50%, about 60%, about 70%, about 75%, about 80%, or about 90% of the cells in the host cell population are not infected by virus. In general, the faster the flow rate of host cells is, the smaller the portion of cells in the host cell population that are infected will be. However, faster flow rates allow for more transfer cycles, e.g., viral life cycles, and, thus, for more generations of evolved vectors in a given period of time, while slower flow rates result in a larger portion of infected host cells in the host cell population and therefore a larger library size at the cost of slower evolution. In some embodiments, the range of effective flow rates is invariably bounded by the cell division time on the slow end and vector washout on the high end In some embodiments, the viral load, for example, as measured in infectious viral particles per volume of cell culture media is substantially constant over the time of the continuous evolution procedure.

The PACE methods provided herein are typically carried out in a lagoon. Suitable lagoons and other laboratory equipment for carrying out PACE methods as provided herein have been described in detail elsewhere. See, for example, International PCT Application, PCT/US2011/066747, published as WO2012/088381 on Jun. 28, 2012, the entire contents of which are incorporated herein by reference. In some embodiments, the lagoon comprises a cell culture vessel comprising an actively replicating population of vectors, for example, phage vectors comprising a gene of interest, and a population of host cells, for example, bacterial host cells. In some embodiments, the lagoon comprises an inflow for the introduction of fresh host cells into the lagoon and an outflow for the removal of host cells from the lagoon. In some embodiments, the inflow is connected to a turbidostat comprising a culture of fresh host cells. In some embodiments, the outflow is connected to a waste vessel, or a sink. In some embodiments, the lagoon further comprises an inflow for the introduction of a mutagen into the lagoon. In some embodiments that inflow is connected to a vessel holding a solution of the mutagen. In some embodiments, the lagoon comprises an inflow for the introduction of an inducer of gene expression into the lagoon, for example, of an inducer activating an inducible promoter within the host cells that drives expression of a gene promoting mutagenesis (e.g., as part of a mutagenesis plasmid), as described in more detail elsewhere herein. In some embodiments, that inflow is connected to a vessel comprising a solution of the inducer, for example, a solution of arabinose.

In some embodiments, the lagoon comprises a controller for regulation of the inflow and outflow rates of the host cells, the inflow of the mutagen, and/or the inflow of the inducer. In some embodiments, a visual indicator of phage presence, for example, a fluorescent marker, is tracked and used to govern the flow rate, keeping the total infected population constant. In some embodiments, the visual marker is a fluorescent protein encoded by the phage genome, or an enzyme encoded by the phage genome that, once expressed in the host cells, results in a visually detectable change in the host cells. In some embodiments, the visual tracking of infected cells is used to adjust a flow rate to keep the system flowing as fast as possible without risk of vector washout.

In some embodiments, the controller regulates the rate of inflow of fresh host cells into the lagoon to be substantially the same (volume/volume) as the rate of outflow from the lagoon. In some embodiments, the rate of inflow of fresh host cells into and/or the rate of outflow of host cells from the lagoon is regulated to be substantially constant over the time of a continuous evolution experiment. In some embodiments, the rate of inflow and/or the rate of outflow is from about 0.1 lagoon volumes per hour to about 25 lagoon volumes per hour. In some embodiments, the rate of inflow and/or the rate of outflow is approximately 0.1 lagoon volumes per hour (lv/h), approximately 0.2 lv/h, approximately 0.25 lv/h, approximately 0.3 lv/h, approximately 0.4 lv/h, approximately 0.5 lv/h, approximately 0.6 lv/h, approximately 0.7 lv/h, approximately 0.75 lv/h, approximately 0.8 lv/h, approximately 0.9 lv/h, approximately 1 lv/h, approximately 2 lv/h, approximately 2.5 lv/h, approximately 3 lv/h, approximately 4 lv/h, approximately 5 lv/h, approximately 7.5 lv/h, approximately 10 lv/h, or more than 10 lv/h.

In some embodiments, the inflow and outflow rates are controlled based on a quantitative assessment of the population of host cells in the lagoon, for example, by measuring the cell number, cell density, wet biomass weight per volume, turbidity, or cell growth rate. In some embodiments, the lagoon inflow and/or outflow rate is controlled to maintain a host cell density of from about $10^2$ cells/ml to about $10^{12}$ cells/ml in the lagoon. In some embodiments, the inflow and/or outflow rate is controlled to maintain a host cell density of about $10^2$ cells/ml, about $10^3$ cells/ml, about $10^4$ cells/ml, about $10^5$ cells/ml, about $5 \times 10^5$ cells/ml, about $10^6$ cells/ml, about $5 \times 10^6$ cells/ml, about $10^7$ cells/ml, about $5 \times 10^7$ cells/ml, about $10^8$ cells/ml, about $5 \times 10^8$ cells/ml, about $10^9$ cells/ml, about $5 \times 10^9$ cells/ml, about $10^{10}$ cells/ml, about $5 \times 10^{10}$ cells/ml, or more than $5 \times 10^{10}$ cells/ml, in the lagoon. In some embodiments, the density of fresh host cells in the turbidostat and the density of host cells in the lagoon are substantially identical.

In some embodiments, the lagoon inflow and outflow rates are controlled to maintain a substantially constant number of host cells in the lagoon. In some embodiments, the inflow and outflow rates are controlled to maintain a substantially constant frequency of fresh host cells in the lagoon. In some embodiments, the population of host cells is continuously replenished with fresh host cells that are not infected by the phage. In some embodiments, the replenishment is semi-continuous or by batch-feeding fresh cells into the cell population.

In some embodiments, the lagoon volume is from approximately 1 ml to approximately 100 l, for example, the lagoon volume is approximately 1 ml, approximately 10 ml, approximately 50 ml, approximately 100 ml, approximately 200 ml, approximately 250 ml, approximately 500 ml, approximately 750 ml, approximately 1 l, approximately 2 l, approximately 2.5 l, approximately 3 l, approximately 4 l, approximately 5 l, approximately 10 l, approximately 20 l, approximately 50 l, approximately 75 l, approximately 100 l, approximately 1 ml-10 ml, approximately 10 ml-50 ml, approximately 50 ml-100 ml, approximately 100 ml-250 ml, approximately 250 ml-500 ml, approximately 500 ml-1 l, approximately 1 l-2 l, approximately 2l-5 l, approximately 5l-10 l, approximately 10l-50 l, approximately 50 l-100 l, or more than 100 l.

In some embodiments, the lagoon and/or the turbidostat further comprises a heater and a thermostat controlling the temperature. In some embodiments, the temperature in the lagoon and/or the turbidostat is controlled to be from about 4° C. to about 55° C., preferably from about 25° C. to about 39° C., for example, about 37° C.

In some embodiments, the inflow rate and/or the outflow rate is controlled to allow for the incubation and replenishment of the population of host cells for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive vector or phage life cycles. In some embodiments, the time sufficient for one phage life cycle is about 10, 15, 20, 25, or 30 minutes.

Therefore, in some embodiments, the time of the entire evolution procedure is about 12 hours, about 18 hours, about 24 hours, about 36 hours, about 48 hours, about 50 hours, about 3 days, about 4 days, about 5 days, about 6 days, about 7 days, about 10 days, about two weeks, about 3 weeks, about 4 weeks, or about 5 weeks.

In some embodiments, a PACE method as provided herein is performed in a suitable apparatus as described herein. For example, in some embodiments, the apparatus comprises a lagoon that is connected to a turbidostat comprising a host cell as described herein. In some embodiments, the host cell is an *E. coli* host cell. In some embodiments, the host cell comprises a mutagenesis expression construct as provided herein, an accessory plasmid as described herein, and, optionally, a helper plasmid as described herein, or any combination thereof. In some embodiments, the lagoon further comprises a selection phage as described herein, for example, a selection phage encoding a gene of interest. In some embodiments, the lagoon is connected to a vessel comprising an inducer for a mutagenesis plasmid, for example, arabinose. In some embodiments, the host cells are *E. coli* cells comprising the F' plasmid, for example, cells of the genotype F'proA$^+$B$^+$ Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ$^-$.

For example, in some embodiments, a PACE method as provided herein is carried out in an apparatus comprising a lagoon of about 100 ml, or about 1 l volume, wherein the lagoon is connected to a turbidostat of about 0.5 l, 1 l, or 3 l volume, and to a vessel comprising an inducer for a mutagenesis plasmid, for example, arabinose, wherein the lagoon and the turbidostat comprise a suspension culture of *E. coli* cells at a concentration of about 5×10$^8$ cells/ml. In some embodiments, the flow of cells through the lagoon is regulated to about 3 lagoon volumes per hour. In some embodiments, cells are removed from the lagoon by continuous pumping, for example, by using a waste needle set at a height of the lagoon vessel that corresponds to a desired volume of fluid (e.g., about 100 ml, in the lagoon. In some embodiments, the host cells are *E. coli* cells comprising the F' plasmid, for example, cells of the genotype F'proA$^+$B$^+$Δ (lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116 λ$^-$.

Host Cells

Some aspects of this invention relate to host cells for continuous evolution processes as described herein. In some embodiments, a host cell is provided that comprises a mutagenesis expression construct as provided herein. In some embodiments, the host cell further comprises additional plasmids or constructs for carrying out a PACE process, e.g., a selection system comprising at least one viral gene encoding a protein required for the generation of infectious viral particles under the control of a conditional promoter the activity of which depends on a desired function of a gene to be evolved. For example, some embodiments provide host cells for phage-assisted continuous evolution processes, wherein the host cell comprises an accessory plasmid comprising a gene required for the generation of infectious phage particles, for example, M13 gIII, under the control of a conditional promoter, as described herein. In some embodiments, the host cell further provides any phage functions that are not contained in the selection phage, e.g., in the form of a helper phage. In some embodiments, the host cell provided further comprises one or more expression constructs (e.g., 1, 2, 3, 4, 5, or more accessory plasmids) comprising a selection system as described herein.

In some embodiments, the host cell is a prokaryotic cell, for example, a bacterial cell. In some embodiments, the host cell is an *E. coli* cell. In some embodiments, the host cell is a eukaryotic cell, for example, a yeast cell, an insect cell, or a mammalian cell. The type of host cell, will, of course, depend on the viral vector employed, and suitable host cell/viral vector combinations will be readily apparent to those of skill in the art.

In some embodiments, the viral vector is a phage and the host cell is a bacterial cell. In some embodiments, the host cell is an *E. coli* cell. Suitable *E. coli* host strains will be apparent to those of skill in the art, and include, but are not limited to, New England Biolabs (NEB) Turbo, Top10F', DH12S, ER2738, ER2267, and XL1-Blue MRF'. These strain names are art recognized and the genotype of these strains has been well characterized. It should be understood that the above strains are exemplary only and that the invention is not limited in this respect.

In some PACE embodiments, for example, in embodiments employing an M13 selection phage, the host cells are *E. coli* cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of *E. coli* cells with certain phage, for example, with M13 phage. For example, in some embodiments, the host cells for M13-PACE are of the genotype F'proA⁺B⁺Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116 λ.

In some embodiments, a PACE apparatus is provided, comprising a lagoon that is connected to a turbidostat comprising a host cell as described herein. In some embodiments, the host cell is an *E. coli* host cell. In some embodiments, the host cell comprises one or more accessory plasmids as described herein (e.g., 1, 2, 3, 4, 5, or more accessory plasmids), and optionally, a helper plasmid as described herein or a mutagenesis plasmid as described herein, or any combination thereof. In some embodiments, the lagoon further comprises a selection phage as described herein, for example, a selection phage encoding a gene of interest. In some embodiments, the lagoon is connected to a vessel comprising an inducer for a mutagenesis plasmid, for example, arabinose. In some embodiments, the host cells are *E. coli* cells comprising the F' plasmid, for example, cells of the genotype F'proA⁺B⁺Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116 λ⁻.

EXAMPLES

Example 1

Strategies for Evolving Protein Stability

σ32 Reporter Strategy

σ32 is a *E. coli* alternate sigma factor that controls the heat shock response. Under normal growth conditions, σ32 is inactivated by binding to cellular chaperones such as DnaK and GroEL. Upon accumulation of misfolded proteins, however, the chaperones are titrated away and σ32 is released to transcribe heat shock genes. This example describes a constructs (e.g., accessory plasmids, "APs") linking a σ32-specific promoter to gene III-neg in PACE to allow for selection against unstable proteins, as shown in FIG. 1A.

Figure 1B:
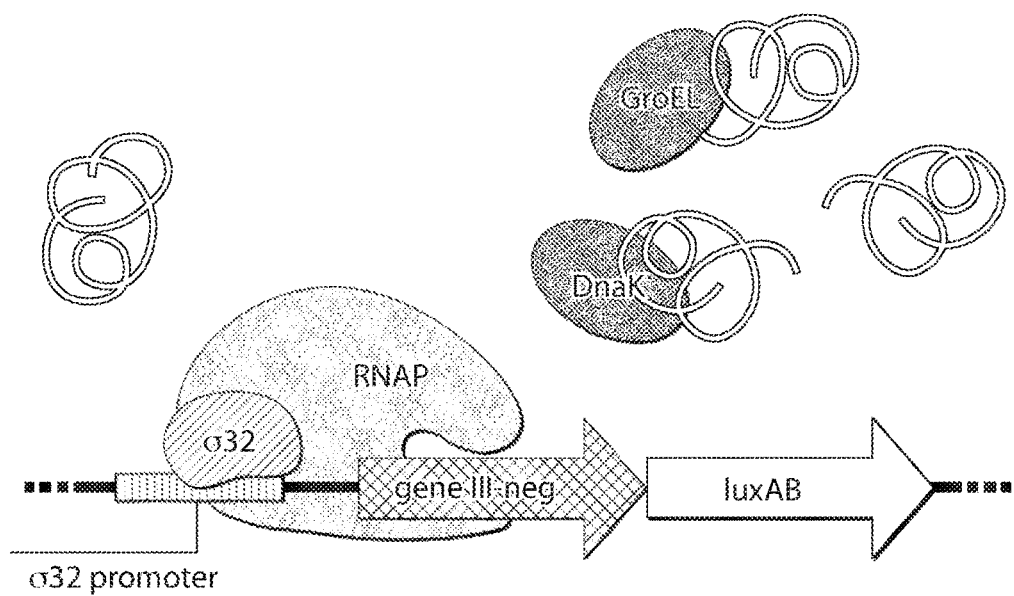
Figure 3A:
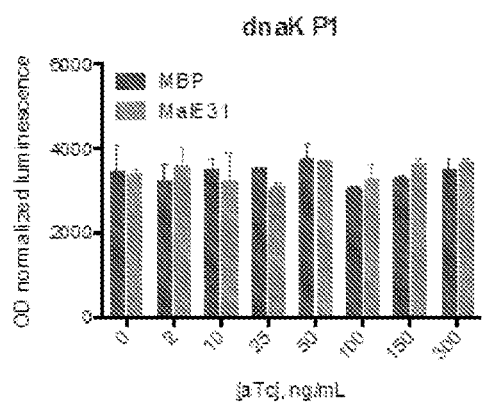
FIGS. 3A-3C show luminescence assay data indicating that σ32 promoter-based reporters do not differentiate between expression of MBP vs. MalE31.
Figure 3B:
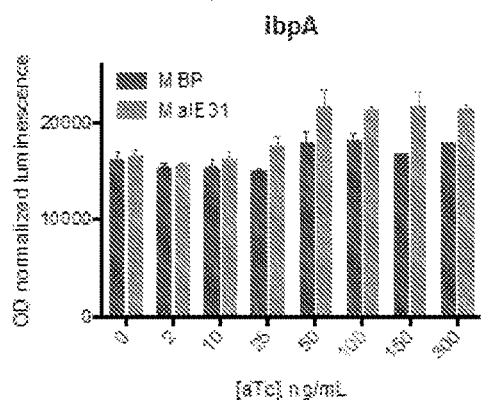
Figure 3C:
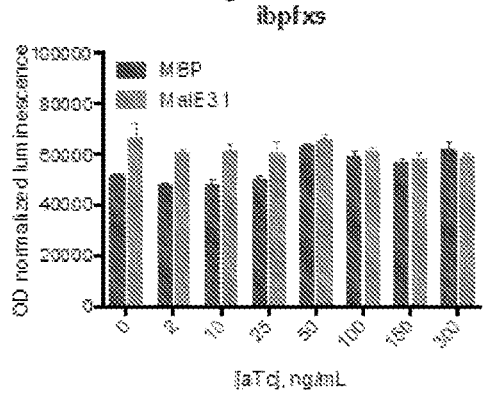

Initial tests used either wt maltose-binding protein (MBP) or a mutant with impaired folding, MalE31, which are mainly expressed in the soluble or insoluble fraction of cell lysates, respectively, as shown in FIG. 1B. Unfortunately, σ32 promoter-based reporters did not differentiate between expression of MBP vs. MalE31 (FIGS. 3A-3C).

Figure 2:
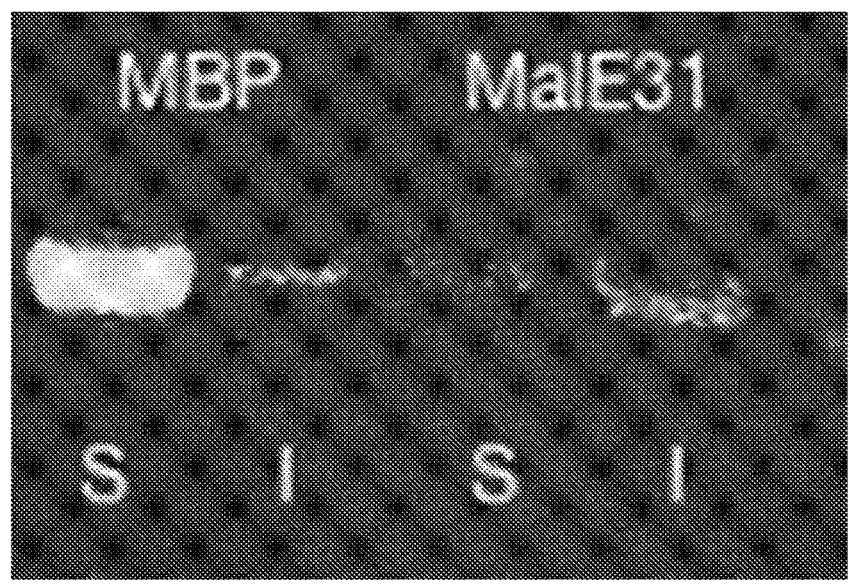
FIG. 2 shows a Western blot of wild-type (wt) maltose-binding protein (MBP) and a mutant MBP with impaired folding, MalE31, in the soluble and insoluble fractions, respectively, of cell lysate.
Figure 4:
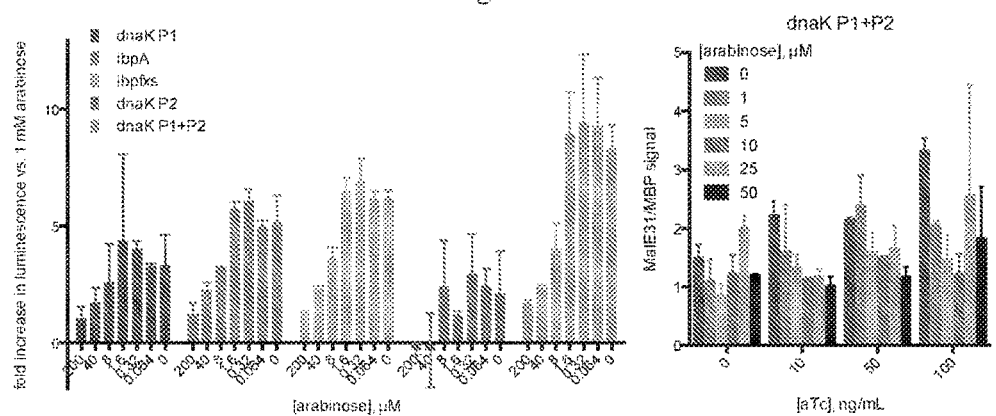
FIG. 4 shows luminescence assay data indicating σ32 reporters respond to dnaKJ induction; minimal differentiation was observed after induction of MBP/MalE31 synthesis.

Using a dnaK KO strain w/dnaKJ under pBAD, a response of σ32 promoters to dnaKJ induction was observed (FIGS. 2A-2C); minimal differentiation was still observed after induction of MBP/MalE31 synthesis (FIG. 4).

Split T7 RNAP Complementation

Figure 5:
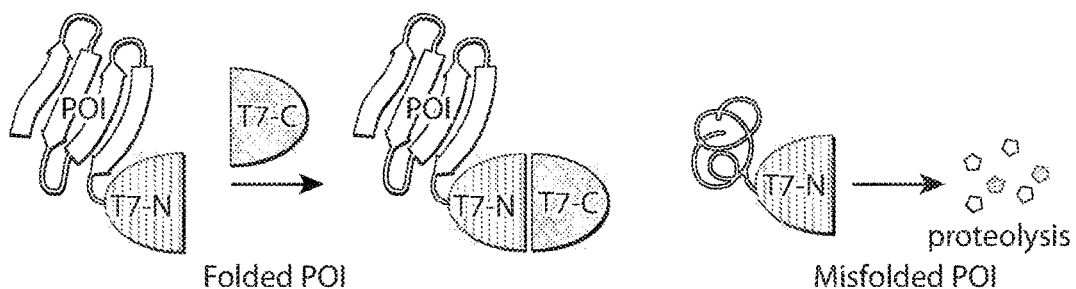
FIG. 5 is a schematic overview of a split T7 RNA polymerase (RNAP) complementation system for PACE selection of properly folded proteins.

The overall folding of a fusion protein can be strongly affected by the stability of the N-terminal component. This example describes fusing a protein to be evolved to the N-terminal fragment of a split T7 RNA polymerase, which results in poorly stable proteins inducing misfolding of the fusion construct, thus preventing the T7 RNAP N-terminal fragment to recombine with the C-terminal fragment of T7 and providing a way to select for protein stability (FIG. 5).

Figure 6A:
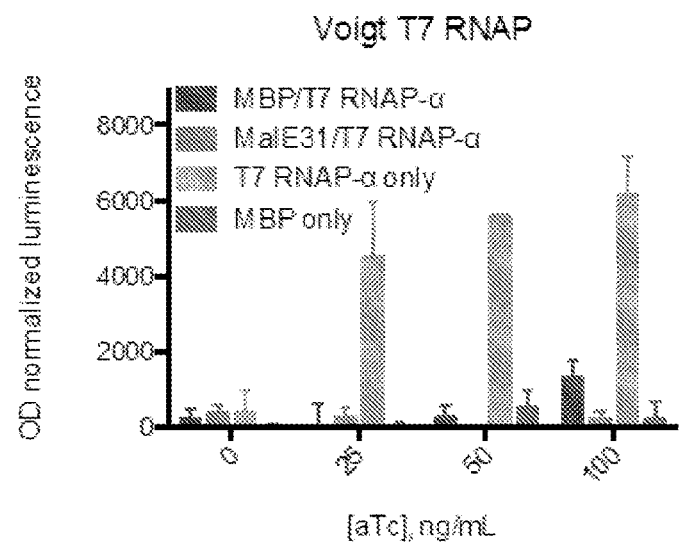
FIGS. 6A-6B show representative data for T7 complementation-based selection strategies.
Figure 6B:
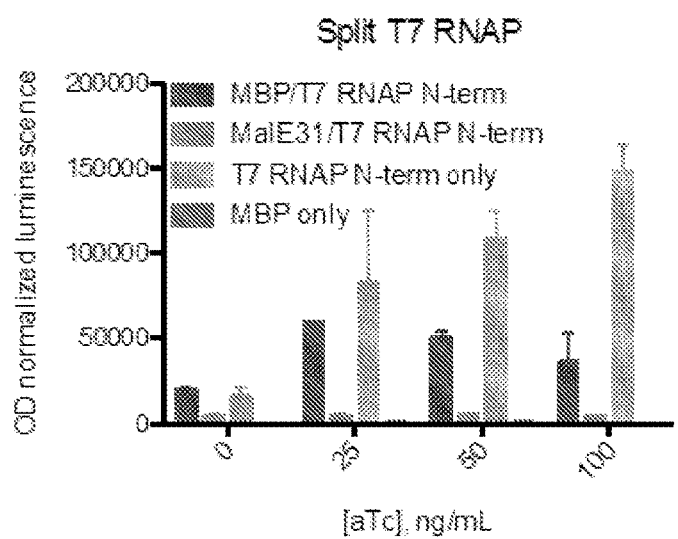
Figure 7A:
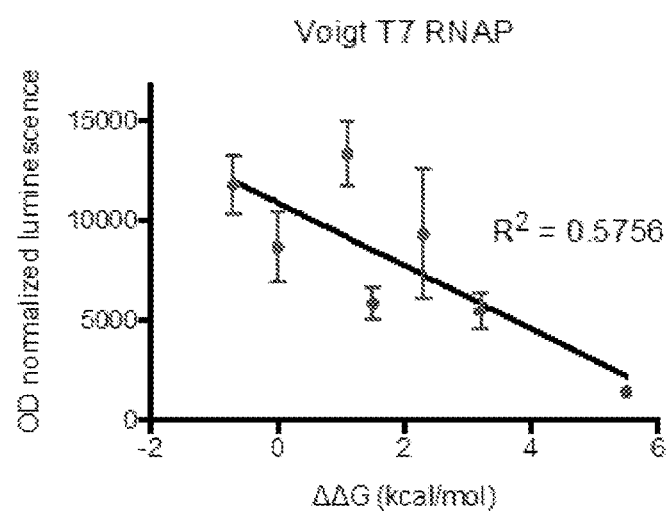
FIGS. 7A-7B show the relationship between T7 RNAP selection and protein stability.
Figure 7B:
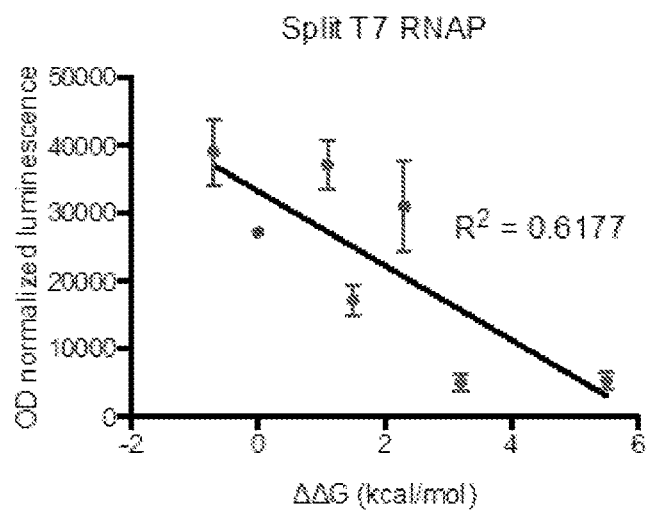

A split T7 RNAP fragment (e.g., Voigt T7 RNA polymerase (RNAP) or Split T7 RNAP) was fused to either MBP (wt) or folding impaired mutant MalE31. The fusions were then evaluated for transcriptional activity through assembling with the other T7 RNAP fragment (FIG. 6A and FIG. 6B). MBP point mutants show the relationship between T7 RNAP complementation and protein stability (ΔΔG), as shown in FIGS. 7A and 7B.

In summary, two strategies for evolving protein stability through PACE are described in this example. The first, is based on the E coli heat shock sigma factor. The second strategy, based on complementation of a split T7 RNA polymerase, has yielded some promising early results, and has displayed the ability to discriminate between proteins of differing stability.

Figure 8A:
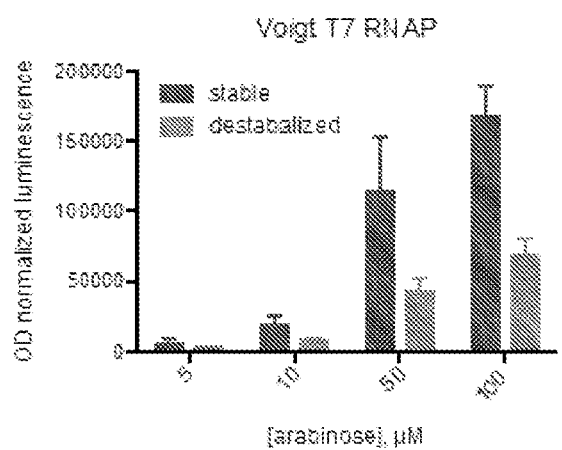
FIGS. 8A-8B show the relationship between T7 RNAP selection and protein stability.
Figure 8B:
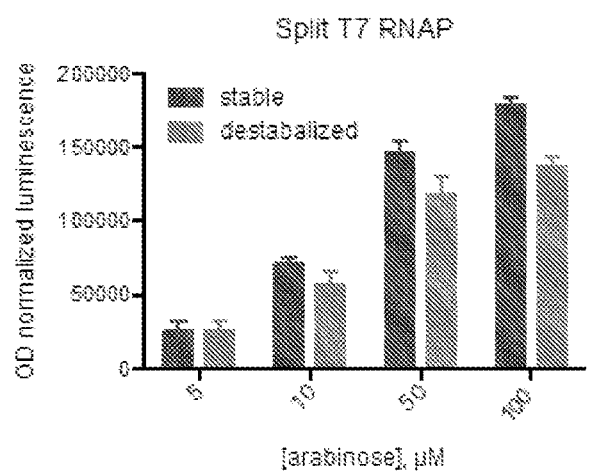

The split T7 polymerase selection system was tested with a different set of proteins with known stabilities (Colicin immunity protein Im7), and attenuated sensitivity was observed, probably due to fusion protein size (Im7~10 kDa vs. MBP ~40 kDa). Supporting this, the fusion using the smaller T7 RNAP fragment ("Voigt T7 RNAP") was more sensitive to Im7 stability (FIG. 8A and FIG. 8B).

Figure 9:
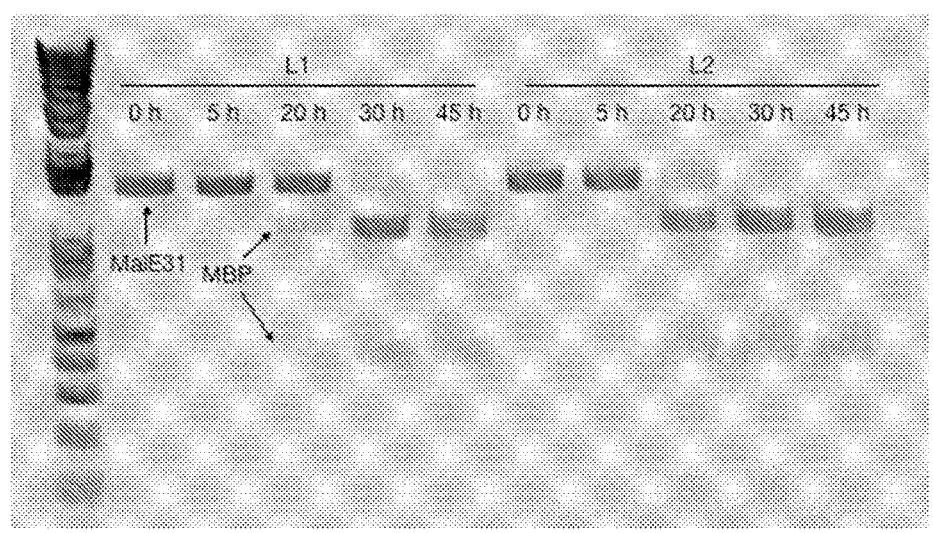
FIG. 9 shows an analytical gel indicating that selection phagemid (SP) encoding MBP outcompete SP encoding misfolded MalE31 during PACE.

MBP/MalE31 split T7 complementation constructs were moved into phage/accessory plasmids (AP). Mock PACE competition experiments with a 1000:1 starting ratio of MalE31 to MBP encoding-selection phagemids (SP) shows enrichment of MBP containing the SPs; however, wild-type contamination was also observed (FIG. 9).

Development of a PACE selection for protein stability based on complementation of a split T7 RNA polymerase has continued. Fusions involving MBP variants showed that the system was able to discriminate between unstable and stable variants. An alternate set of proteins (Im7 variants) with previously measured stabilities were tested in the system. Although the general trend of the more stable protein fusion giving higher T7 RNAP transcriptional activity was observed, the sensitivity of the system was greatly attenuated, likely due to the much smaller size of Im7 vs. MBP. Preliminary mock PACE competition experiments confirm the ability of SP encoding well-folded MBP to enrich over SP encoding poorly folded MalE31.

Figure 10A:
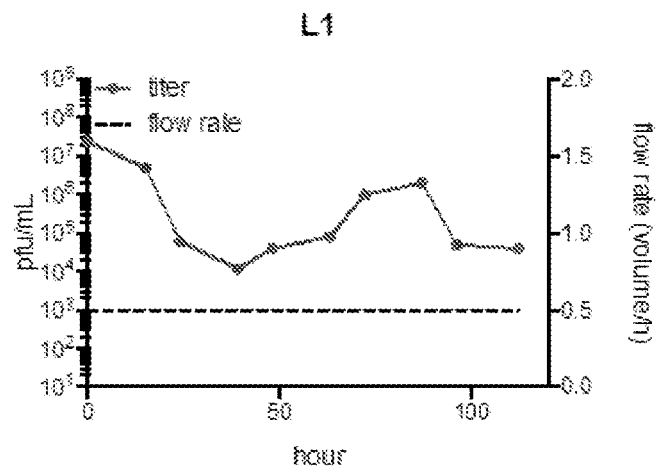
FIGS. 10A-10B show PACE experiments with SP encoding MalE31 folding mutant (G32D/I33P).
Figure 10B:
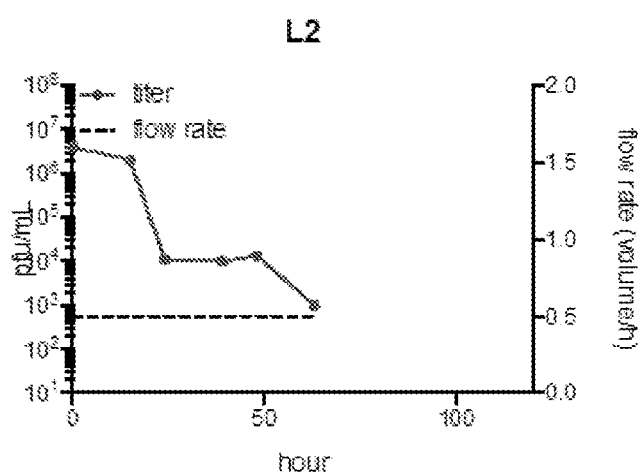

A PACE experiment with SP encoding the MalE31 folding mutant (G32D/I33P) was run to investigate if stabilizing mutations could be observed. Two identical PACE lagoons were set up (L1 and L2); L2 washed out (FIG. 10B), but L1 began recovering after ~60 h (FIG. 10A); some mutations were observed starting at 87 h, as shown in Table 1. The PACE experiment appears to have a low overall mutation rate, indicating that selection pressure is not high. Running the 87 h aliquot in an additional 96 hours of PACE resulted in no new consensus mutations.

TABLE 1

|  | MalE31 | | | | T7 N-term |
|---|---|---|---|---|---|
| 87-1 | P33T | V76I | A167V | V373I | L39F |
| 87-2 | P33T | | | T275I | |
| 87-3 | P33S | | | | A386E |
| 87-4 | P33T | | | | |

Figure 11:
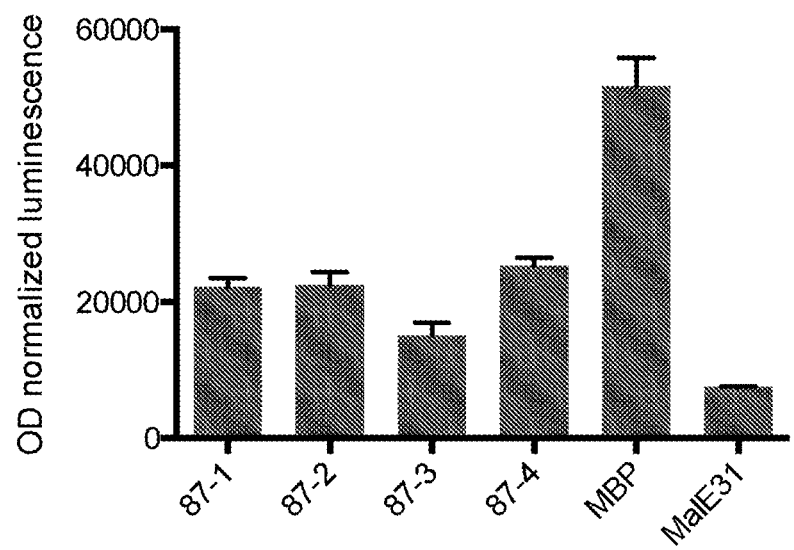
FIG. 11 shows characterization of PACE mutants produced by evolution of MalE31. Luciferase assay data indicate enrichment of MalE31 mutants with increased stability relative to un-mutated MalE31.
Figure 12:
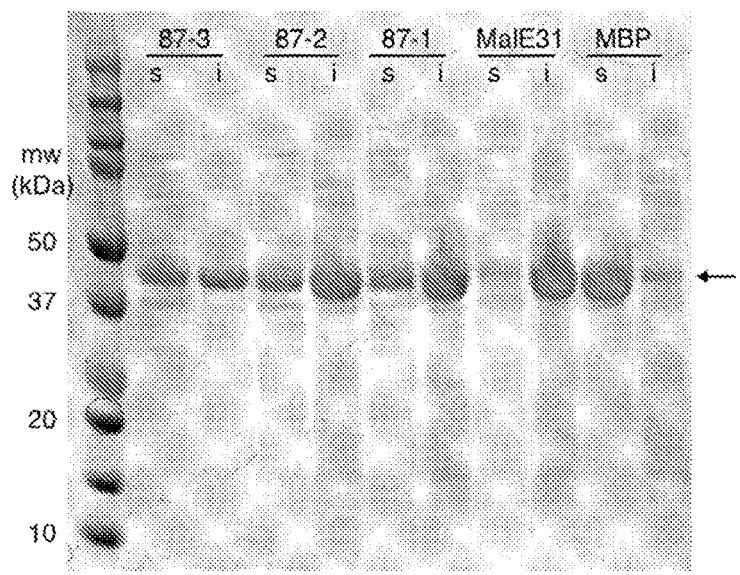
FIG. 12 shows an analytical gel indicating increased expression of MalE31 PACE mutants in the soluble fraction of cell lysates relative to un-mutated MalE31.
Figure 13:
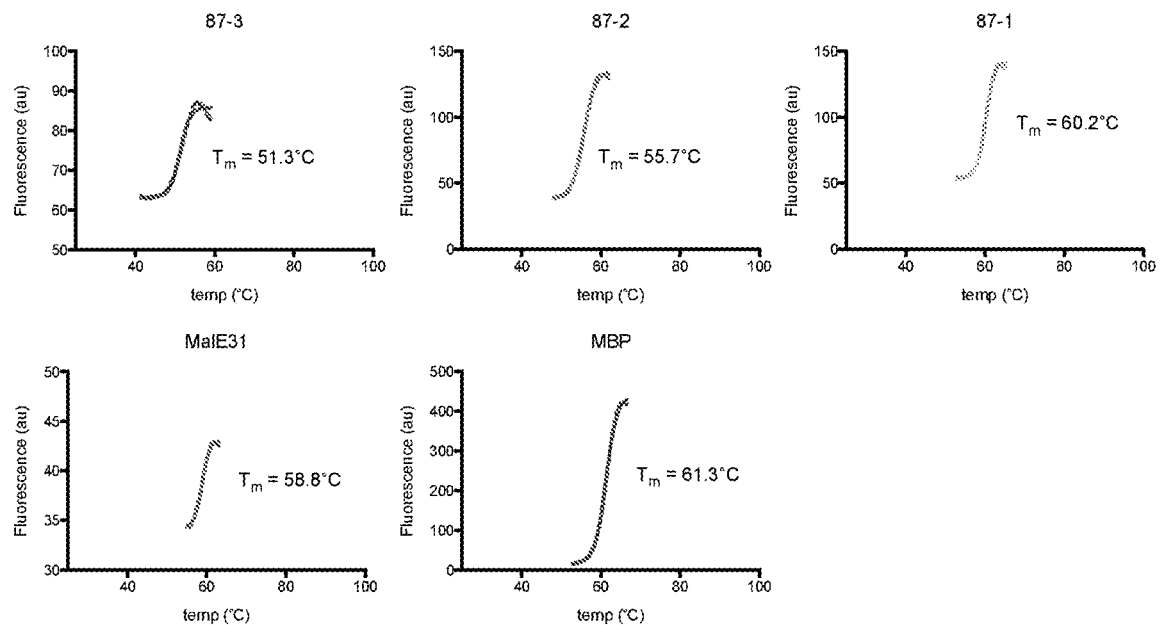
FIG. 13 shows melting temperatures of MalE31 PACE mutants, MBP and un-mutated MalE31.

PACE evolved MalE31 variants were characterized using a Luciferase reporter system. As shown in FIG. 11, increased luminescence was observed for several MalE31 variants, indicating the presence of beneficial mutations. Expression of MalE31 variants in soluble and insoluble cell lysate fractions was also investigated. Increased expression of MalE31 variants was observed in the soluble cell lysate fraction, as shown in FIG. 12. Melting temperature of MalE31 variants was also investigated. Representative data are shown in FIG. 13 and Table 2.

TABLE 2

|  | 87-3 | 87-2 | 87-1 | MalE31 | MBP |
|---|---|---|---|---|---|
| $T_m$ [a] | 51° C. | 55° C. | 60° C. | 58° C. | 61° C. |
| $\Delta\Delta G$ [b] | +1.2 | +0.3 | +4.7 | +6.9 | 0.0 |

[a] Melt temperature
[b] Calculated by fitting to the 2-state model, assuming specific heat capacity of 6.9 kcal/K g (Novokhatny and Ingham, Protein Sci 1997, p. 141) for all variants.

Figure 14:
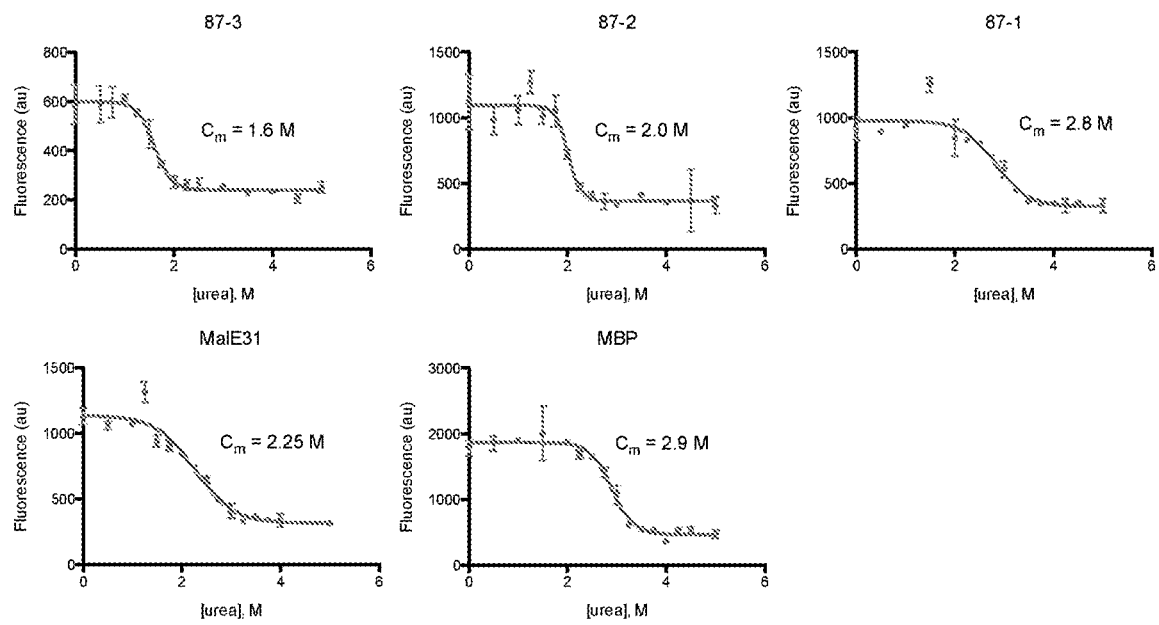
FIG. 14 shows equilibrium urea denaturing for MalE31 PACE mutants, MBP and un-mutated MalE31, as measured by tryptophan fluorescence.
Figure 15:
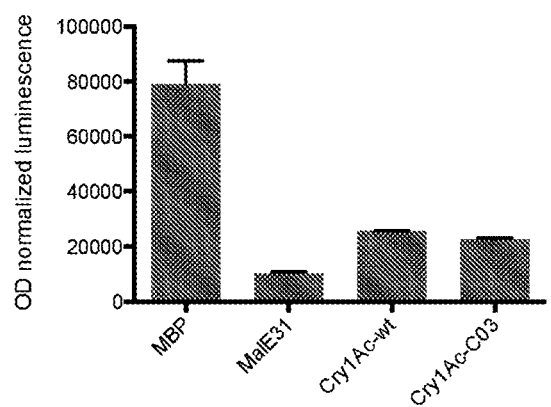
FIG. 15 shows luminescence data for Cry1Ac/T7 N-terminal fusion proteins in the Split T7 RNAP complementation assay.
Figure 16A:
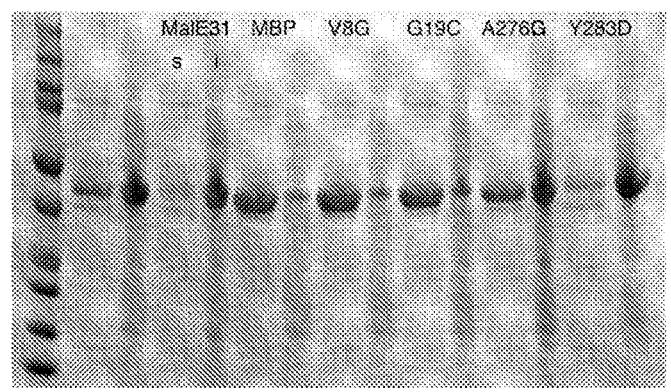
FIGS. 16A-16B show analysis of expression of other MBP variants suggests that the split T7 RNAP system is selecting for soluble protein expression.
Figure 16B:
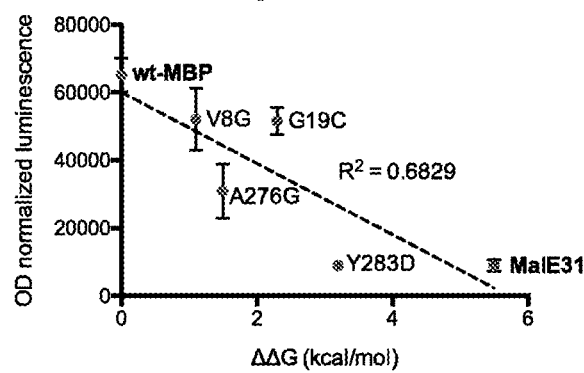
Figure 17A:
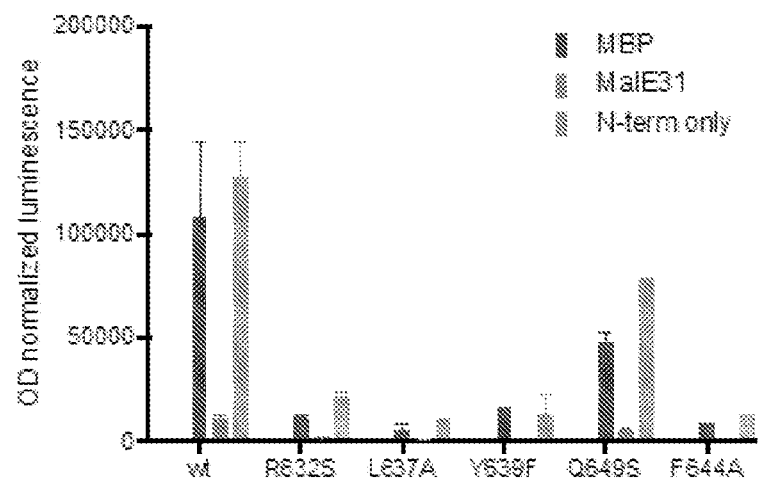
FIGS. 17A-17B show luminescence assay data for MBP PACE using T7 RNAP variants that have reduced transcriptional activity.
Figure 17B:
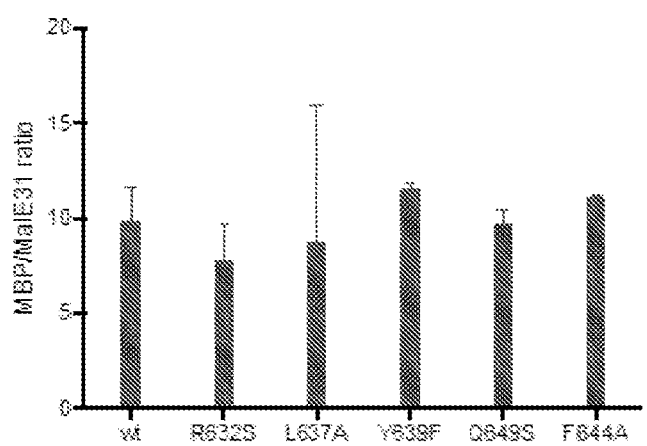
Figure 18:
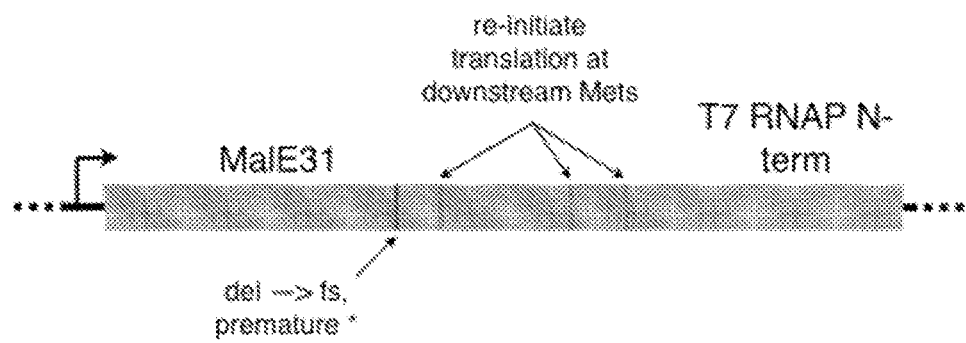
FIG. 18 is a schematic overview of translational re-initiation of T7RNAP downstream of MalE31 during PACE.
Figure 19:
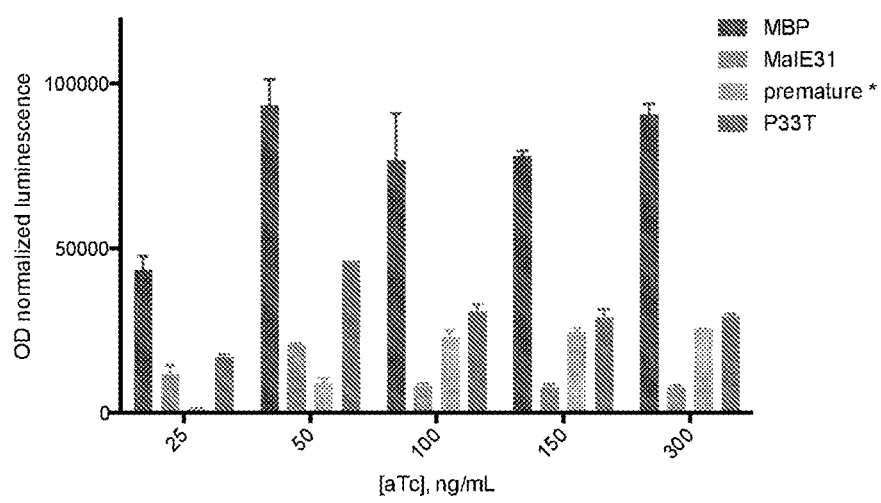
FIG. 19 shows data indicating that translational re-initiation may be compensated for by strong induction. aTc=anhydrotetracycline.
Figure 20:
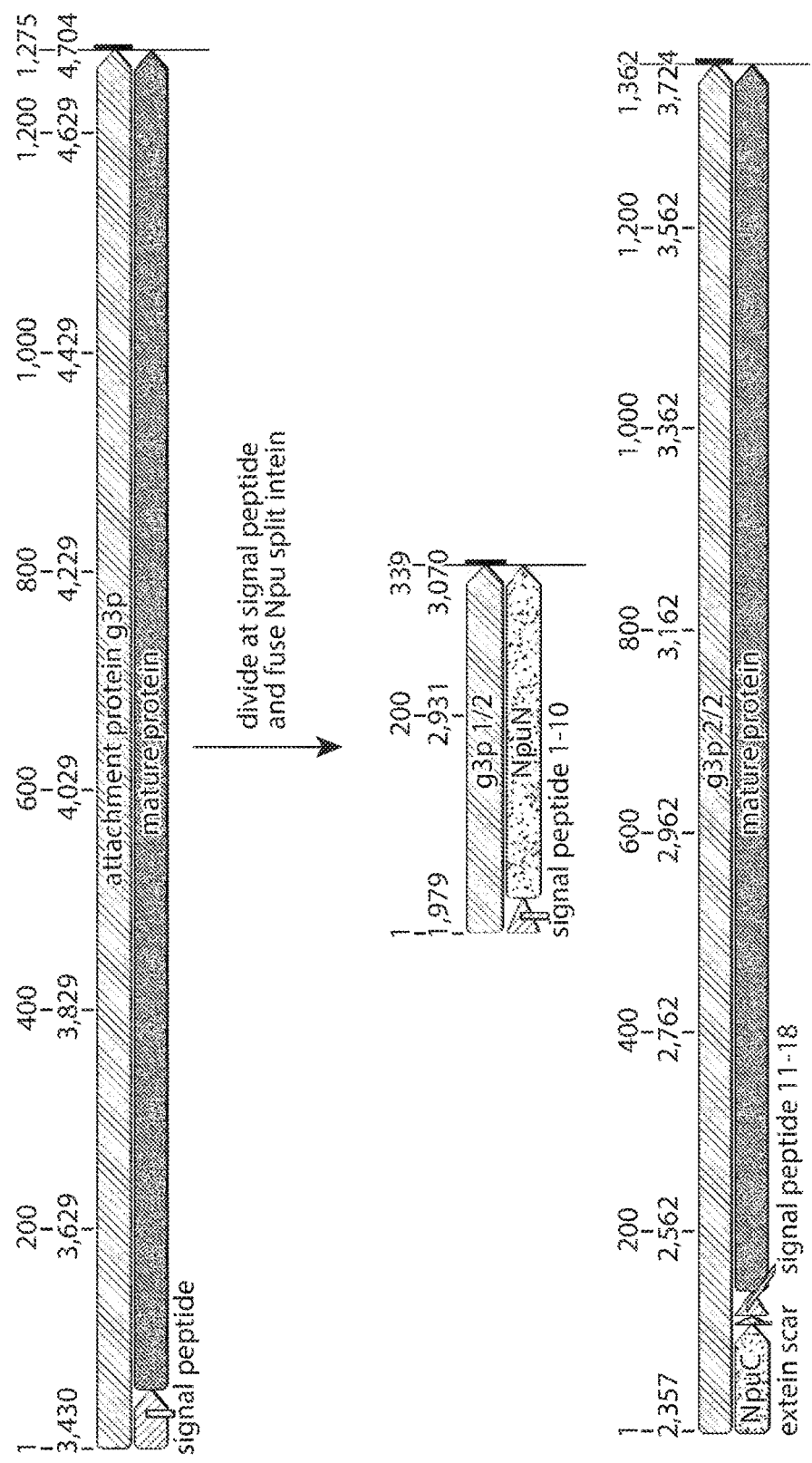
FIG. 20 shows a schematic overview of a split Npu intein selection strategy. Phage protein pIII is localized to the membrane by recognition of an N-terminal signal peptide. The signal peptide of pIII was split in two non-functional halves and fused the N- and C-terminal portions of the Npu split intein to create an "and gate" that requires both intein/g3p fusions to be produced in order to produce infectious phage during PACE.
Figure 21:
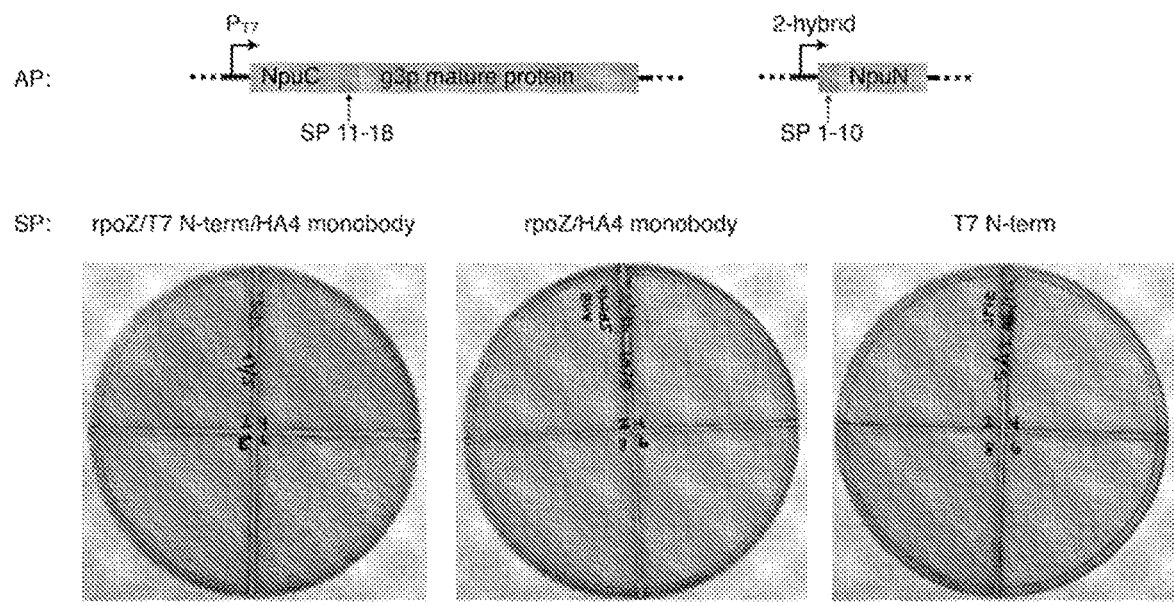
FIG. 21 shows one embodiment of a split Npu intein selection system for PACE. The top panel is a schematic overview of the accessory plasmid (AP) used in this experiment. The bottom panel shows agar plates for each selection phage (SP) used for PACE selection of HA4 monobody variants. Data indicate that expression of HA4 monobody variants requires reconstitution of the pIII mature protein by interaction of the N- and C-terminal portions of the split Npu intein.
Figure 22:
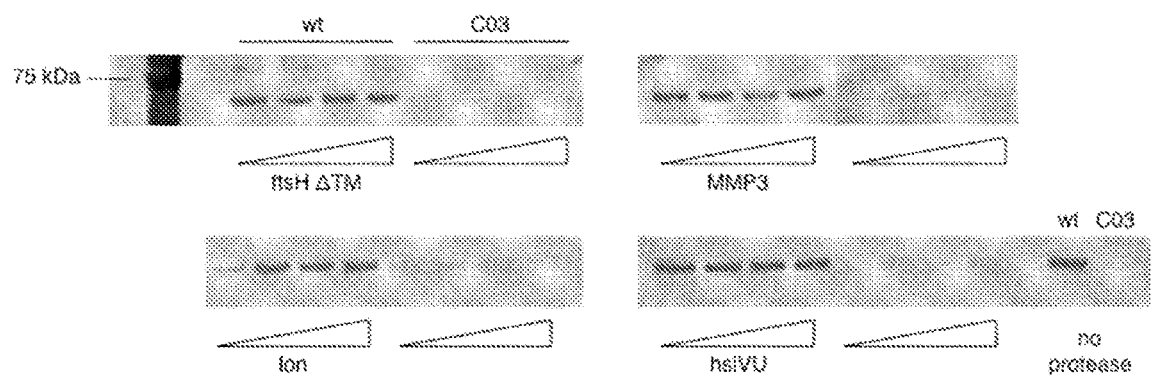
FIG. 22 shows representative Western blots from PACE experiments in which protease (e.g., FtsH, MMP3, Lon, hs1VU) and Cry1Ac (wild-type (wt) and C03 variant) are co-expressed in cells.
Figure 23:
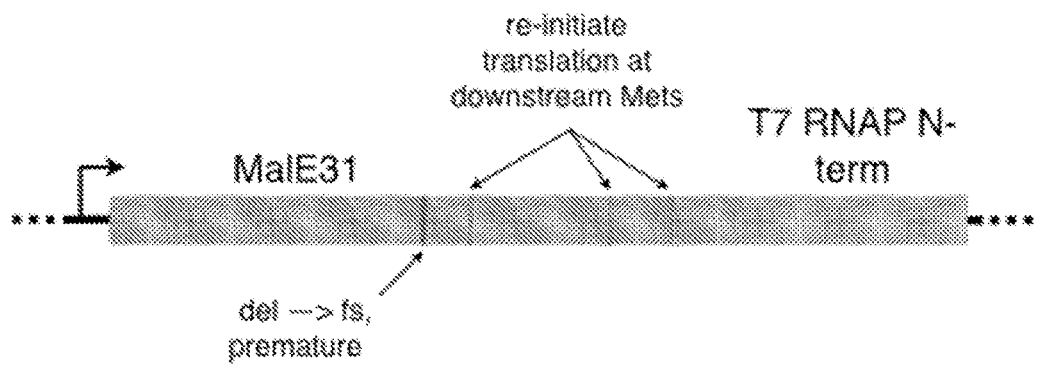
FIG. 23 is a schematic overview of translational re-initiation of T7RNAP downstream of MalE31 during PACE.

Equilibrium urea denaturing by tryptophan fluorescence of MalE31 variants was also measured, as shown in FIG. 14 and Table 3.

TABLE 3

|  | 87-3 | 87-2 | 87-1 | MalE31 | MBP |
|---|---|---|---|---|---|
| $C_m$ [a] | 1.6M | 2.0M | 2.8M | 2.25M | 2.9M |
| $\Delta\Delta G$ [b] | +3.4 | +2.2 | +0.08 | +1.6 | 0.0 |

[a] Urea concentration at midpoint of unfolding
[b] Calculated as a product of $C_m$ and the average slope of $\Delta G$ (calculated by 2-state model) vs. [urea].

Initial studies using Cry1Ac/T7 N-terminal fusions in the split T7 complementation assay were performed. The initial assay uses the exact same format as the MBP/MalE31 system (e.g., the same linkers, T7 C-term induction level, etc.). No differentiation between the mutant and wild-type Cry1Ac were observed in initial experiments. However, the Cry1Ac mutant is not nearly as destabilized vs. wild-type as MalE31 is relative to MBP. It was observed that both Cry1Ac fusions exhibit markedly lower luminescence signal, likely due to larger size relative to MBP (FIG. 15).

In summary, the split T7 RNAP complementation based selection for protein stability has been applied to evolving the MBP G32D/I33P folding mutant (MalE31) in PACE. Mutations occurred primarily at P33, which has previously been identified as the major factor responsible for MalE31 aggregation. The resulting variants exhibited improvements in the luciferase reporter assay and in solubility when expressed. Two variants (87-1 and 87-2) exhibited lower Tm and Cm compared to MalE31, while the third (87-3) was improved over MalE31 (FIGS. 16A-16B).

Example 2

Analysis of Other MBP Variants

Analysis of expression of other MBP variants suggests that the split T7 complementation system is selecting for soluble protein expression. This example describes development of new APs to increase selection stringency.

Mutations in T7 RNAP that have been previously shown to decrease transcriptional activity were observed, as shown in FIG. 17A and 17B. This indicates occurrence of premature stop codon enrichment resulting in translational of the downstream T7 RNAP N-term unburdened by fusion protein, as shown in FIG. 18. For example, PACE on APs containing T7 R632S mutation resulted in enrichment of frameshift mutations resulting in premature stop codons.

Translational re-initiation is inefficient, but may be compensated for through strong induction, as shown in FIG. 19.

Example 3

Development of a Dual Selection System to Prevent Premature Stop Enrichment by Requiring Presence of Functional Fusion Protein One way to prevent enrichment of premature stop codons is to simultaneously select for protein of interest (POI) activity and proper protein folding. In this embodiment, the PACE selection system is arranged such that both POI activity and protein solubility are required before PIII is made.

PIII is localized to the membrane by recognition of an N-terminal signal peptide. The signal peptide was split in two non-functional halves and fused the N- and C-terminal portions of the Npu split intein to create an "and gate" that requires both intein/g3p fusions to be produced in order to produce infectious phage (FIG. 20). For example, in the context of H4A monobody PACE using this selection system, both HA4 monobody binding to SH2/434-cI and active T7 RNAP N-term are required for plaque formation (FIG. 21). Note that a premature stop would result in the RNA polymerase subunit omega (rpoZ) and the HA4 monobody no longer being operatively connected, thus failing the 2-hybrid circuit.

In summary, the N-terminal fragment of a split T7 RNAP was fused to maltose binding protein (MBP) mutants with various known stabilities. The fusions were then evaluated for transcriptional activity through assembling with the other T7 RNAP fragment, and demonstrated a correlation between T7 RNAP transcriptional activity and fusion protein stability. The poorly folding MalE31 folding mutant (G32D/I33P) was evolved in PACE and a consensus mutations at P33 were observed. However, the evolved MBP variants were not significantly thermodynamically stabilized vs. MalE31, but appeared to have greater solubility. Further PACE experiments produced no new consensus mutations, but increasing stringency only resulted in frameshift mutations allowing for translational re-initiation at T7 RNAP N-term (FIG. 23). To address this, a system for dual PACE selection was developed based off pIII split intein.

Example 4

Protease Co-Expression with Cry1Ac wt/C03 Mutant

Co-expression of a protease that is expressible in host cells and preferentially degrades the Cry1Ac C03 mutant was investigated. Proteases were chosen for precedence for expression in *E coli* and for broad substrate scope. Proteases expression was co-induced with Cry1Ac expression in cells, which were then lysed and probed for Cry1Ac by western blot (to N-terminal 6×His tag), as shown in FIG. 22.

Plasmids expressing trypsin that are tolerated by the host strain have been cloned. SP expressing rpoZ fused to either Cry1Ac C03 or C03 reversion (D384Y/S404C) were also cloned and propagated on 2-hybrid (2-H) AP in the presence of increasing protease expression from $P_{rha}$ (which express the proteases hs1VU or bovine trypsin from a rhamnose promoter ($P_{rha}$)). It was observed that hs1VU expression did not differentiate between C03 and C03 reversion. Trypsin expression results are shown in Table 4 and indicate a difference in affinity of the C03 mutant and reversion for the bait. The tryptic core (tc) fragments of Cry1Ac have also been cloned and tested with the T7 selection system.

TABLE 4

| [rhamnose], mM | C03; # plaques @ dilution | reversion |
|---|---|---|
| 0 | 7 @ $10^8$ | 11 @ $10^8$ |
| 1 | 6 @ $10^8$ | 1 @ $10^8$ |
| 10 | 2 @ $10^6$ | 7 @ $10^4$ |

Example 5

Optimized Dual PACE Selection

Figure 24A:
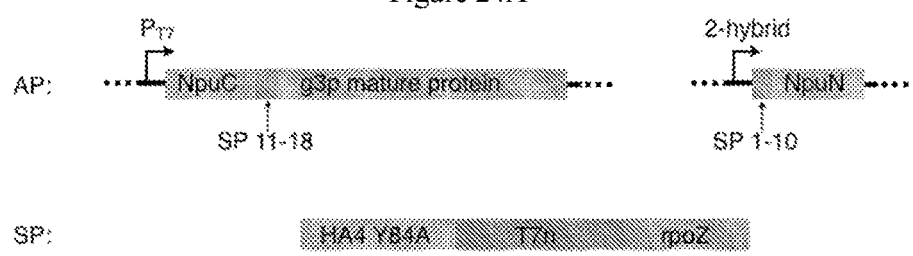
FIGS. 24A-24C show one embodiment of dual PACE selection strategy.
Figure 24B:
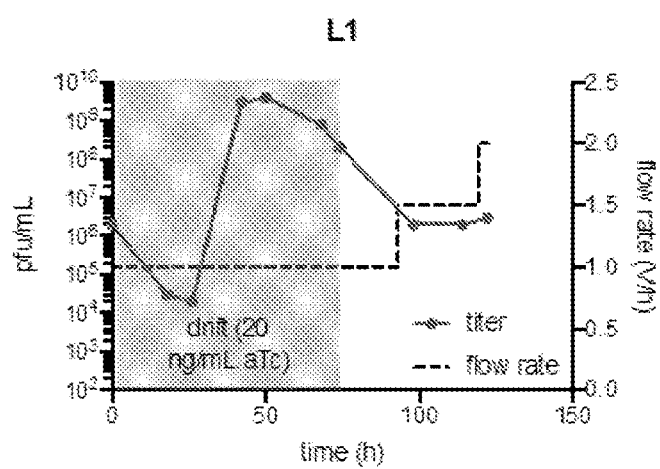
Figure 24C:
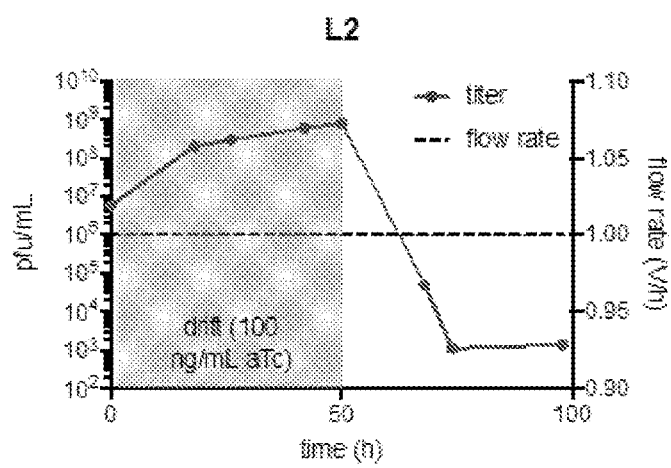

Validation of dual PACE selection with HA4 Y84A monobody was investigated. A SP comprising the Y84A mutation, which ablates HA4 monobody binding to SH2 domain of Abl1 kinase, was produced. This SP is active on the T7 AP, but not on the 2-hybrid AP (FIG. 24A). Overall the ON propagation on this AP combo is ~105 fold lower than the wt HA4 monobody. Results from two PACE lagoons are shown in FIGS. 24B and 24C, which show the titers of phage in this PACE experiment. While L2 phage washed out (shown in FIG. 24C), L1 phage (shown in FIG. 24B) found the mutations shown in Table 5. L1 mutations at 122 h are extremely convergent, as shown in Table 5.

TABLE 5

| | HA4 Y84A | | | T7n | | | | rpoZ | |
|---|---|---|---|---|---|---|---|---|---|
| 1 | V14 | A82E | A84M | K70N | Q103K | S127R | L29 | L57 | |
| 2 | V14 | A82E | A84M | K70N | Q103K | S127R | L29 | L57 | |
| 3 | V14 | A82E | A84M | K70N | Q103K | S127R | L29 | L57 | |
| 4 | V14 | A82E | A84M | K70N | Q103K | S127R | L29 | L57 | |
| 5 | V14 | A82E | A84M | K70N | Q103K | S127R | L29 | L57 | |
| 6 | V14 | A82E | A84M | K70N | Q103K | S127R | L29 | L57 | L67fs |
| 7 | V14 | A82E | A84M | K70N | Q103K | S127R | L29 | L57 | |
| 8 | V14 | A82E | A84M | K70N | Q103K | S127R | L29 | L57 | |

Figure 25A:
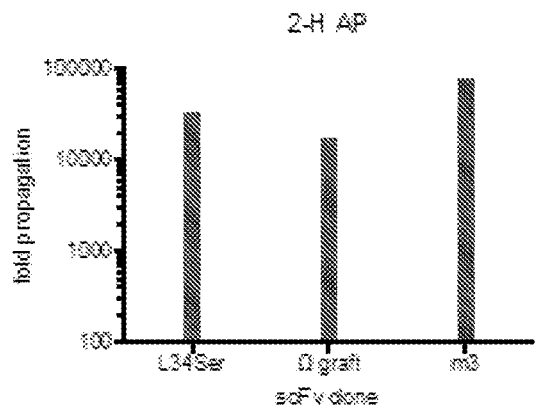
FIGS. 25A-25C show application of a dual selection PACE strategy to protein solubility of GCN4-binding scFvs.
Figure 25B:
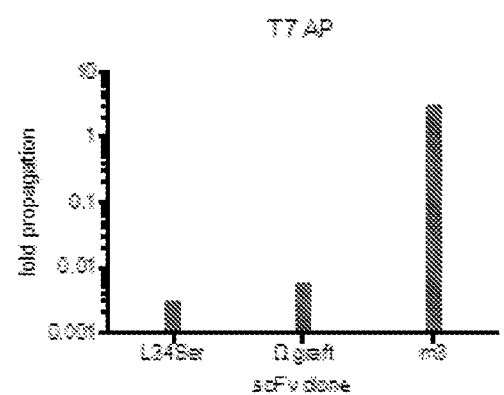
Figure 25C:
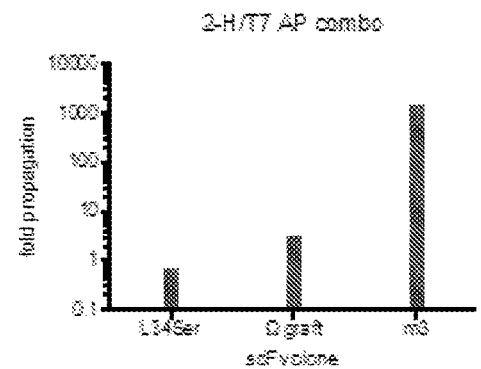

Dual PACE selection was also applied to protein solubility. Several related scFvs bind the yeast tf GCN4 leucine zipper. Reported clones L34Ser, Ωgraft, and m3 exhibit increasing degrees of solubility, with m3 reported to exist mostly in soluble form in E coli cytosol. Propagation assays using dual selection APs show selectivity only on the T7 end, as shown in FIGS. 25A-25C.

Example 6

Development of Alternative, Non-Fusion Based Solubility Selection

A split T7 complementation system generally works in the case where a sandwich fusion can be made where T7 N-terminus is in the middle. This example describes identification of a more general selection system.

The small chaperones ibpA and ibpB are known to associate with inclusion bodies. For example, ibpA-fluorescent protein fusions have been used to image inclusion bodies in E coli. Here, ibpA or ibpB was fused with T7 N-terminus for split T7 RNAP complementation. In this PACE selection system, upon formation of inclusions bodies, ibpA/B is sequestered, preventing transcription of $P_{T7}$-gIII. This reporter was tested in 3 different cell types (clpB works with dnaK to solubilize inclusion bodies) under the following conditions:

AP: T7 C-term driven by $P_{BAD}$

Plasmid 1 (ColE1): ibpA/ibpB T7 N-term fusion driven by $P_{tet}$

Plasmid 2 (CloDF13): MBP or MalE31 driven by $P_{BAD}$

Figure 26A:
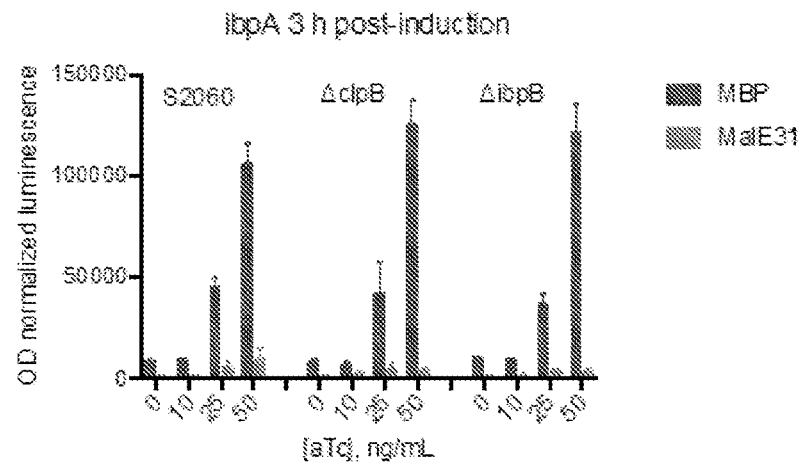
FIGS. 26A-26B show non-fusion-based solubility selection during PACE.
Figure 26B:
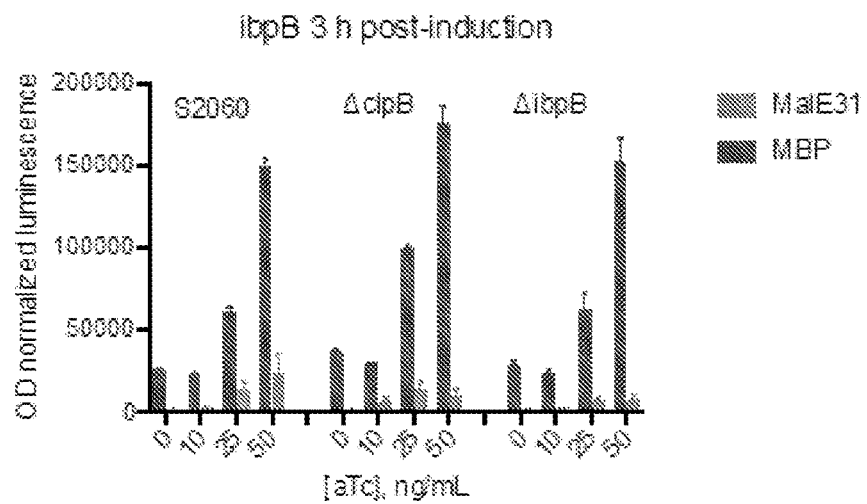

Representative data are shown in FIG. 26A and FIG. 26B. It was observed that this selection system is heavily dependent on the amount of protein of interest (POI) induced, and also the kinetics of POI vs. ibpA/B synthesis.

Example 7

Validation of PACE Selection for Protein Solubility

Figure 27A:
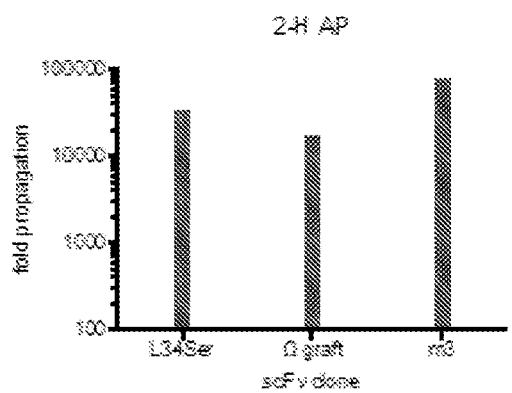
FIGS. 27A-27C show application of a dual selection PACE strategy to protein solubility of GCN4-binding scFvs.
Figure 27B:
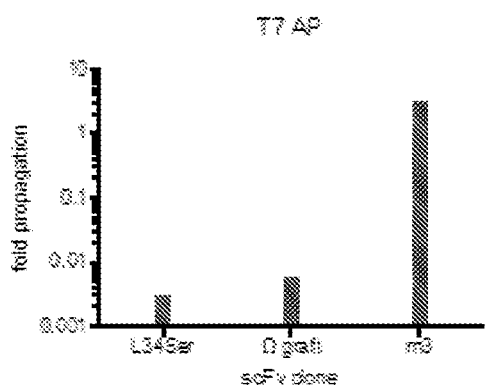
Figure 27C:
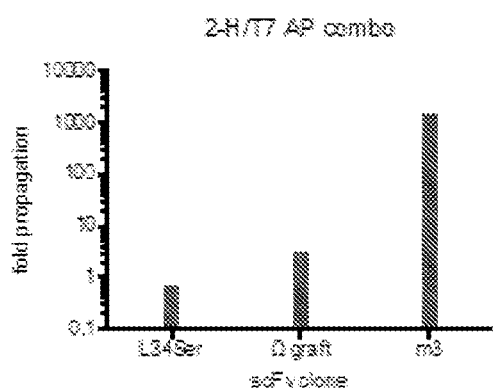

Several related scFvs bind the yeast transcription factor (tf) GCN4 leucine zipper. It has been observed that clones L34Ser, Ωgraft, and m3 exhibit increasing degrees of solubility, with m3 reported to exist mostly in soluble form in E. coli cytosol. Propagation assays using dual selection APs show selectivity only on the T7 end, as shown in FIGS. 27A-27C.

Figure 28:
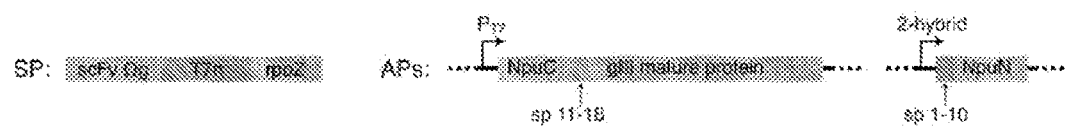
FIG. 28 shows a schematic overview of a split Npu intein selection strategy for PACE of Ωgraft scFv variants having increased solubility.
Figure 29A:
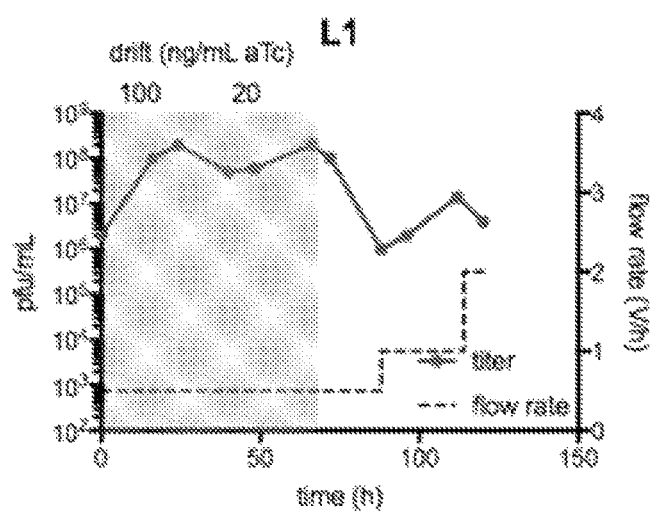
FIGS. 29A-29C show representative data for plaque-forming units (pfus) of Ωgraft scFv variants from three PACE lagoons, L1 (FIG. 29A), L2 (FIG. 29B), and L3 (FIG. 29C).
Figure 29B:
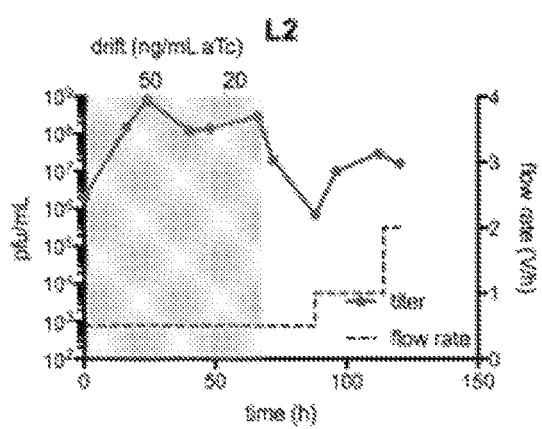
Figure 29C:
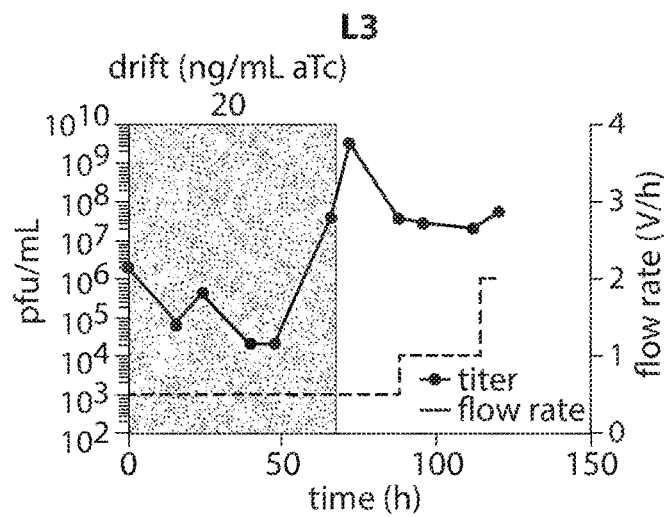

PACE of Ωgraft was performed. The SP and APs used for Ωgraft dual-selection PACE are shown in FIG. 28. Results from three PACE lagoons are shown in FIGS. 29A-29C, which show titers of phage in all three lagoons persisted upon increased flow rates, indicating solutions were found in all three lagoons. Mutations present in both Ωgraft variants (left) and T7n are shown in Table 6. Soluble vs. insoluble expression of Ωgraft variants subcloned from SPs are shown in FIG. 30.

TABLE 6

| | anti-GCN4 Ωg | | | | | | | |
|---|---|---|---|---|---|---|---|---|
| L1-120-1 | | | I71V | | Y96D | | | |
| L1-120-2 | | | | F91Y | A93V | | A172S | A194 |
| L1-120-3 | | | | | Y96C | | | |
| L1-120-4 | | | | F91Y | | G141D | | |
| L1-120-5 | | | | | Y96D | | | |
| L1-120-6 | | | | | Y96D | | | |
| L2-120-1 | | | S38L | | | | V182A | |
| L2-120-2 | | S13L | S38L | | | | V182A | |
| L2-120-3 | I3V | S36L | | | | | | |
| L2-120-4 | | | S368L | | | | V182A | |
| L2-120-5 | | | S38L | | | | | |
| L2-120-6 | | | S38L | | | | V182A | |
| L3-120-1 | | | | A93V | Y96D | | | I183 |
| L3-120-2 | | | | | Y96D | | | |
| L3-120-3 | | | | A93V | Y96D | | | |
| L3-120-4 | | | | | Y96D | | | |
| L3-120-5 | | | | | Y96D | | | |
| L3-120-6 | | | | | Y96D S132I | | | |
| | | | | | T7n | | | |
| L1-120-1 | | | | | | | S127R | |
| L1-120-2 | | | | | | | S127R | |
| L1-120-3 | | | | | | | S127R | |
| L1-120-4 | | | | R49S | | | | |
| L1-120-5 | | | | | | | S127R | |

TABLE 6-continued anti-GCN4 Ωg

| ID | Mutations |
|---|---|
| L1-120-6 | R30C, S127R |
| L2-120-1 | N4, D12, G46D, A67T, K92, Q106K, N130K |
| L2-120-2 | N4, D12, G46D, A67T, Q106K, N130K |
| L2-120-3 | N4, D12, G46D, A67T, Q106K, N130K |
| L2-120-4 | N4, D12, G46D, A67T, Q106K, N130K |
| L2-120-5 | G46D, Q106K, N130K |
| L2-120-6 | N4, D12, G46D, A67T, Q106K, N130K |
| L3-120-1 | S127R |
| L3-120-2 | R49, S127R |
| L3-120-3 | A48E, S127R |
| L3-120-4 | S127R |
| L3-120-5 | S127R |
| L3-120-6 | E62D, S127R |

It was observed that mutations in T7n account for a lot of the overall activity increase. To address this, these PACE experiments were repeated with increasingly stringent T7 APs to try and "max out" T7n evolution. Stringency of the T7 APs was increased by using T7 promoter variants or T7 RNAP C-terminal domain mutants that impaired transcriptional activity. Representative data are shown in Tables 7 and 8.

TABLE 7 anti-GCN4 Ωg

| ID | Mutations |
|---|---|
| L1 PACE 1 | Y96D |
| L1 PACE 2 | A37V, T106M, G129S, D190N, F232L |
| L1 PACE 3 | A37V, S81N, F87S, Y96H, T106M, R112L, G129S, D190N, F232L |
| L2 PACE 1 | S38L, V182A |
| L2 PACE 2 | S38L, Y96H, R112H, L136P, V182A |
| L2 PACE 3 | S38L, Y96H, N98D, R112H, L136P, V182A |
| L3 PACE 1 | A93V, Y96D |
| L3 PACE 2 | E42K, A93V, Y96D |
| L3 PACE 3 | E42K, A93V, Y96D |

TABLE 8

T7n

| ID | Mutations |
|---|---|
| L1 PACE 1 | S127R |
| L1 PACE 2 | G46D, K70E, S127R |
| L1 PACE 3 | G46D, K70E, K97R, Q106K, S127R |
| L2 PACE 1 | G46D, A67T, Q106K, N130K |
| L2 PACE 2 | G46D, A67T, N85K, Q106K, N130K |
| L2 PACE 3 | D96G, G46D, A67T, K70N, N85K, Q103H, Q106K, D129N, N130K |
| L3 PACE 1 | S127R |
| L3 PACE 2 | M45I, S127R, V133I |
| L3 PACE 3 | M45I, L78P, Q103R, S127R, D129G, V133I | rpoZ

| ID | Mutations |
|---|---|
| L1 PACE 1 | |
| L1 PACE 2 | |
| L1 PACE 3 | D7G, V21A |
| L2 PACE 1 | |
| L2 PACE 2 | Y177H |
| L2 PACE 3 | Y177H |
| L3 PACE 1 | |
| L3 PACE 2 | |
| L3 PACE 3 | V19L, F62V, R66L |

Example 8

Revisiting MalE31 with Dual Selection

As described above, PACE experiments were run with the split T7 solubility selection for the MalE31 folding mutant (MBP G32D/I33P). Mutations in the MalE31 mutant and T7n are shown in Table 9.

TABLE 9

| | MalE31 | | | | T7n |
|---|---|---|---|---|---|
| 87-1 | P33T | V76I | A167V | V373I | L39F |
| 87-2 | P33T | | | T275I | |
| 87-3 | P33S | | | | A386E |
| 87-4 | P33T | | | | |

Figure 31A:
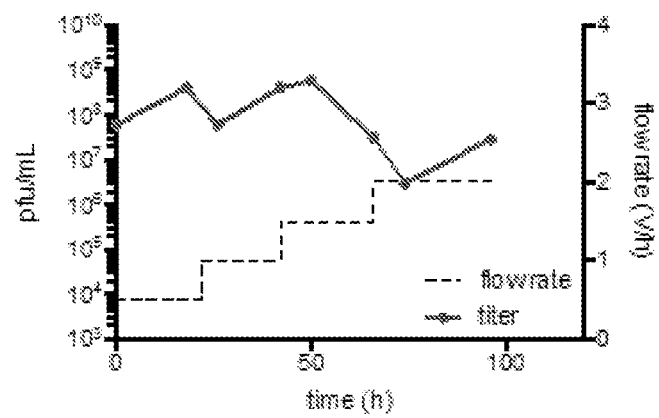
FIGS. 31A-31B show representative data for plaque-forming units (pfus) of MalE31 variants during PACE using split Npu intein.
Figure 31B:
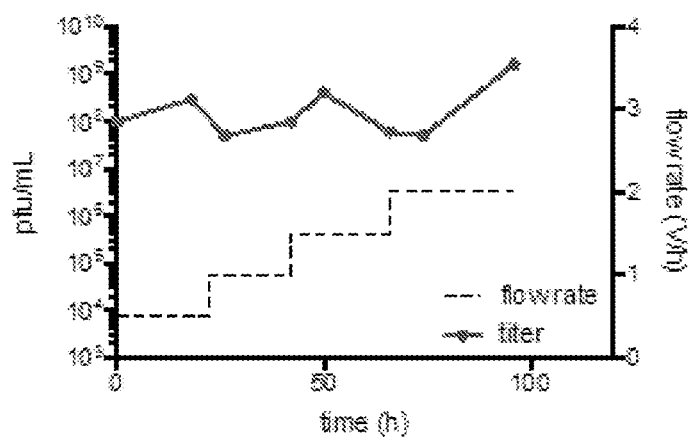
Figure 32:
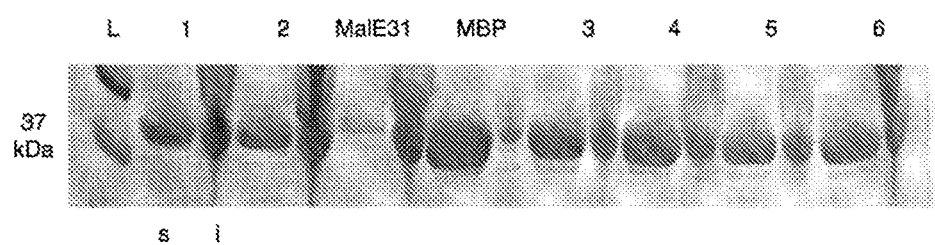
FIG. 32 shows a Western blot indicating MalE31 variants evolved by split Npu intein PACE have increased solubility compared to the starting clones (P33S/A386E and P33T/T275I, respectively). s=soluble fraction; i=insoluble fraction; L=ladder; 1=P33S/A386E (starting clone 1); 2=P33T/T275I (starting clone 2); 3=D32G/P33T/S233L (evolved from clone 2); 4=D32G/P33S/F67L (evolved from clone 1); 5=D32G/P33S/S233L (evolved from clone 1); 6=D32G/P33T/P159L (evolved from clone 2).

This PACE experiment was performed using an anti-MBP monobody for the 2-H selection component. Two clones from the first PACE experiment with MalE31 were evolved to investigate whether their solubility could be further improved. Representative data from the PACE experiment is shown in FIGS. 31A and 31B. Sequencing revealed that the G32D of MalE31 (G32D/I33P) had been reverted by the end of this PACE in both lagoons, as shown in Table 10. The effects of PACE mutation on soluble expression of MalE31 reverted variants was investigated. Data indicate that soluble expression was improved in PACE variants relative to the original clones, as shown in FIG. 32.

TABLE 10

MalE31

| | | | | | | | | | | |
|---|---|---|---|---|---|---|---|---|---|---|
| L3-96-1 | N12S | | P33T | | | G68D | Y99H | | | |
| L3-96-2 | | | D32G P33T | A52V | | | | | K202N | |
| L3-96-4 | | | P33T | | A63T | L89 | Y99H | N100H | | |
| L3-96-5 | | | D32G P33T | | A63E | | | | | |
| L3-96-6 | | | D32G P33T | | | | | | | S233L |
| L3-96-7 | | | P33T | | A63T | | Y99H | | | | S255P |
| L3-96-8 | | | D32G P33T | | | | Y99H | | | N234D |
| L4-96-1 | | | D32G P33S | | F67L | | | | | |
| L4-96-2 | | | P33S | F61I | | | | | | |
| L4-96-3 | | | D32G P33S | | F67L | | | | | |
| L4-96-4 | | | D32G P33S | | | | | | E214G | |
| L4-96-5 | | | D32G P33S | | F67L | | | | | |
| L4-96-6 | | L20 | D32G P33S | | | | | M148I | | S233L |
| L4-96-7 | | K26R | D32G P33S | | | | | | | S233L |
| L4-96-8 | | | D32G P33S | | | | | | | S233L |

T7n | rpoZ

| | T7n | | rpoZ | |
|---|---|---|---|---|
| L3-96-1 | G46S | T132I | D35V | |
| L3-96-2 | K97 | | A1S | F62 |
| L3-96-4 | | | | |
| L3-96-5 | E55 | | | |
| L3-96-6 | G141 | | | |
| L3-96-7 | | | | |
| L3-96-8 | A64E | | | |
| L4-96-1 | | | | |
| L4-96-2 | A48T | T132I | | |
| L4-96-3 | | | | |
| L4-96-4 | E145 A158S | | | |

TABLE 10-continued

| | | |
|---|---|---|
| L4-96-5 | V3A | K11E |
| L4-96-6 | | |
| L4-96-7 | | |
| L4-96-8 | E40G | |

Example 9

PACE of Cry1Ac C03 Tryptic Core

Figure 33A:
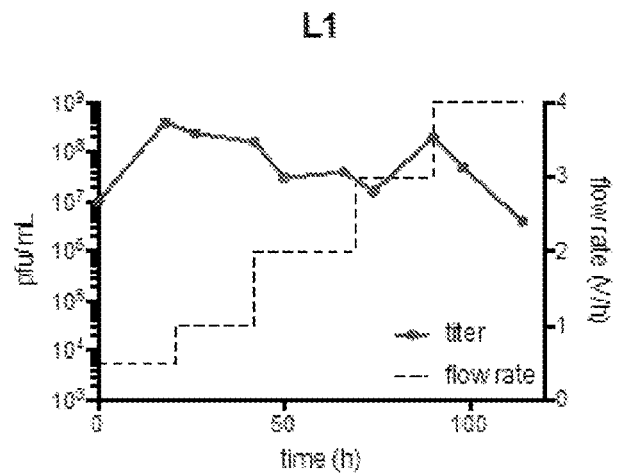
FIGS. 33A-33B show data from two lagoons, L1 (FIG. 33A) and L2 (FIG. 33B) from PACE of the Cry1Ac tryptic core.
Figure 33B:
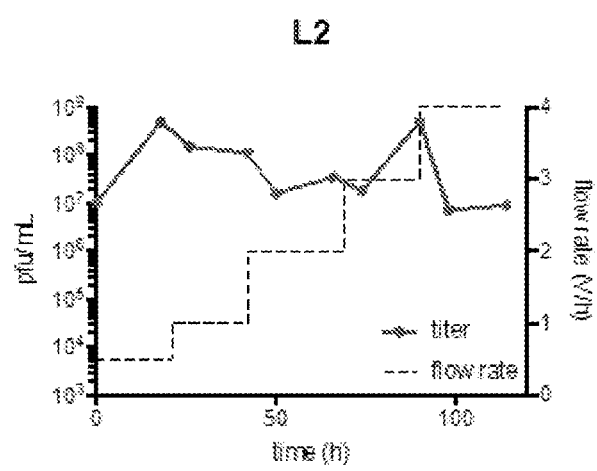

It was previously observed that Cry1Ac tryptic core (tc) fragments show zero propagation on the T7 APs. In this example, PACE of Cry1Ac tc was run with a highly permissive T7 AP. Representative data from the PACE experiments is shown in FIG. 33A and FIG. 33B. Mutations arising from the PACE experiments are shown in Tables 11 and 12.

TABLE 11

| | Cry1Ac | | | | | | | | | |
|---|---|---|---|---|---|---|---|---|---|---|
| L1-114-1 | I2R | | D10N | Q17 | F23S | | | | L209 | N247T |
| L1-114-2 | | | | | | I36R | | | | |
| L1-114-3 | | | D10G | | | I36R | | I118V V128I | | |
| L1-114-4 | | | D10G | | | I36R | | | | |
| L2-114-1 | | Y6 | | I11T | | I36R | | I118V | R154M | |
| L2-114-2 | | G5S | | | | I36R | I37V E89K | V148G | N185 | |
| L2-114-3 | | G5S | | I11T | | I36R | I37V | | | S234F |
| L2-114-4 | | | | I11S | | I36R | | | | |

| | Cry1Ac | | | | | | | | |
|---|---|---|---|---|---|---|---|---|---|
| L1-114-1 | | | | | S416R | S417G | | | |
| L1-114-2 | G305E | | | | S416R | S417G | | | |
| L1-114-3 | G305E | T30I | A318S | | S416R | S417G | | | |
| L1-114-4 | G305E | T307I | | | | | V418G | | |
| L2-114-1 | G305E | | | R375 | S416R | S417G | | I512 | I523V |
| L2-114-2 | F301Y | G305E | | | S416R | S417G | T461T | | |
| L2-114-3 | G305E | | | | S416R | S417G | | | |
| L2-114-4 | G305E | | | G398 | S416R | S417G | | G561 | |

TABLE 12

| | T7n | | | | | | | |
|---|---|---|---|---|---|---|---|---|
| L1-114-1 | | | K70N | I73L | F88V | | | |
| L1-114-2 | | | | | | | | |
| L1-114-3 | M34V | | | | | | A158V | |
| L1-114-4 | | R49L | | R83H | | I144 | | |
| L2-114-1 | | | | I73L | R83H | | | |
| L2-114-2 | | | K70 | | | | | |
| L2-114-3 | | | K70N | | | R127K | | |
| L2-114-4 | S42A | | | | | | | |

TABLE 12-continued

| | | rpoZ | | |
|---|---|---|---|---|
| L1-114-1 | | V19L | | |
| L1-114-2 | | | | |
| L1-114-3 | | | | |
| L1-114-4 | | | | |
| L2-114-1 | | | V21A | |
| L2-114-2 | I12V | | | E55G |
| L2-114-3 | I12V | | | A84S |
| L2-114-4 | | | T45A | |

Figure 34:
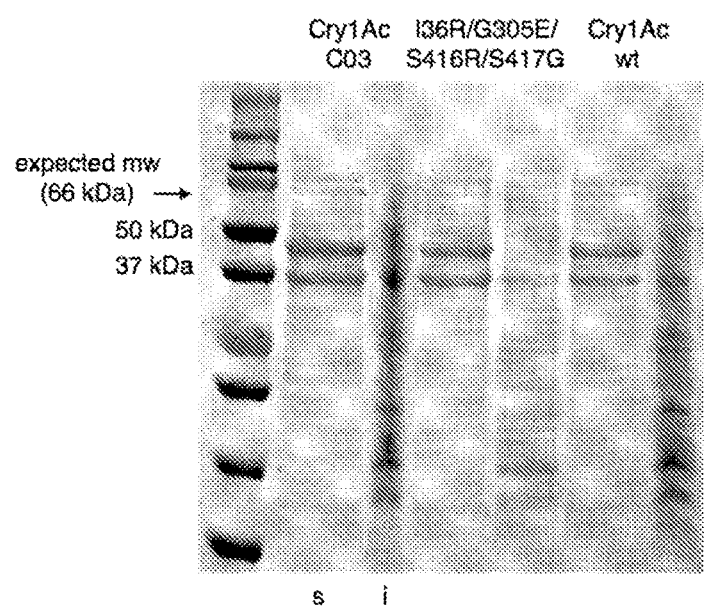
FIG. 34 shows a Western blot of Cry1Ac C03, a PACE-evolved Cry1Ac C03 variant (consensus mutations I36R/G305E/S416R/S417G) and wt Cry1Ac from soluble (s) and insoluble (i) cell lysate fractions.

Consensus mutations in Cry1Ac C03 tc fragment were observed, including I36R/G305E/S416R/S417G. The consensus mutant, Cry1Ac C03 tc and wild-type Cry1Ac (wt) tc fragment were subcloned for expression as follows. Briefly a pET vector expressing 6×His-SSGLVPRGSH-Cry1Ac tc (or other variant) was produced. Using BL21 DE3, cells were grown up to OD 0.4, induced with 1 mM IPTG, and shaken 3 h at 37° C. before protein was extracted using B-per reagent and protease inhibitors. A representative Western blot is shown in FIG. 34. No 65-66 kDa band (e.g., the expected molecular weight of Cry1Ac) was observed; the predominant band observed was at ~47 kDa.

In summary, dual selection for protein binding and protein solubility has been described. Modest increases in solubility were obtained with evolving scFvs, but improvements in T7n are a significant contribution to passing the selection. Cry1Ac C03 tc fragment was also evolved using this system and resulted in the presence of consensus mutations.

Example 10

Application of Evolved T7n to Anti-GCN4 scFv ΩGraft

As described above, improvements in Ωgraft solubility were achieved using PACE selection systems described by the disclosure. However, it was observed that mutations accumulating in T7n dominated the selection. This example describes evolution of T7n through 3 increasingly stringent PACEs to obtain the following consensus mutations, shown in Table 13.

TABLE 13

| L2 PACE 1 | | G46D | A67T | | | Q106K | | N130K |
|---|---|---|---|---|---|---|---|---|
| L2 PACE 2 | | G46D | A67T | | N85K | Q106K | | N130K |
| L2 PACE 3 | D9G | G46D | A67T | K70N | N85K | Q103H Q106K | D129N | N130K |

Figure 35A:
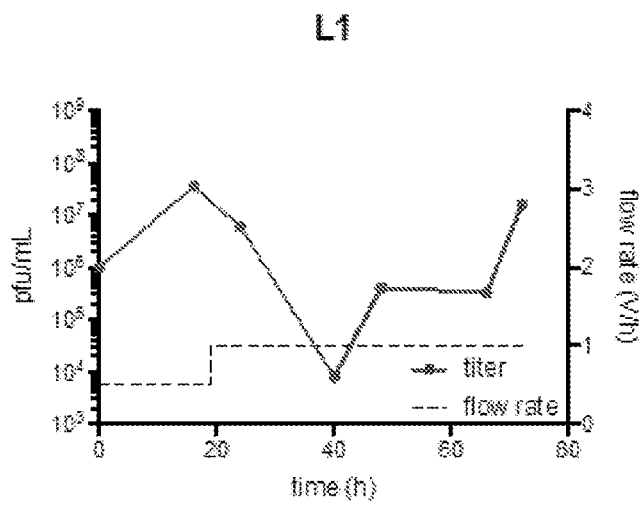
FIGS. 35A-35B show representative data for plaque-forming units (pfus) of Ωgraft scFv variants from three PACE lagoons, L1 (FIG. 35A) and L2 (FIG. 35B).
Figure 35B:
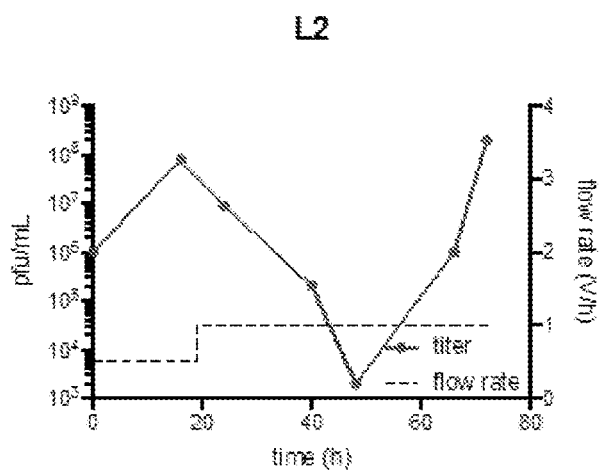

Another PACE experiment was run with wt Ωgraft and T7n from L2 PACE 3 described above. Representative data from the PACE experiments are shown in FIG. 35A and FIG. 35B. No consensus mutations in T7n were observed for L1, as shown in Table 14.

TABLE 14

| | Linker | | | T7n evolved | | | |
|---|---|---|---|---|---|---|---|
| L1-72-1 | S38L | | | F91Y | | | |
| L1-72-2 | S38L | V40I | F87S | | D190N | T131I | K159N |
| L1-72-3 | | | | | | | |
| L1-72-4 | S38L | V40I | F87S | | D190N | | |
| L1-72-5 | | | F87S | G103S | L224V | | |
| L1-72-6 | | | F87S | G103S | L224V | | |
| L1-72-7 | | | F87S | G103S | L224V | | |
| L1-72-8 | S38L | V40I | | | D190N | | |

Figure 36:
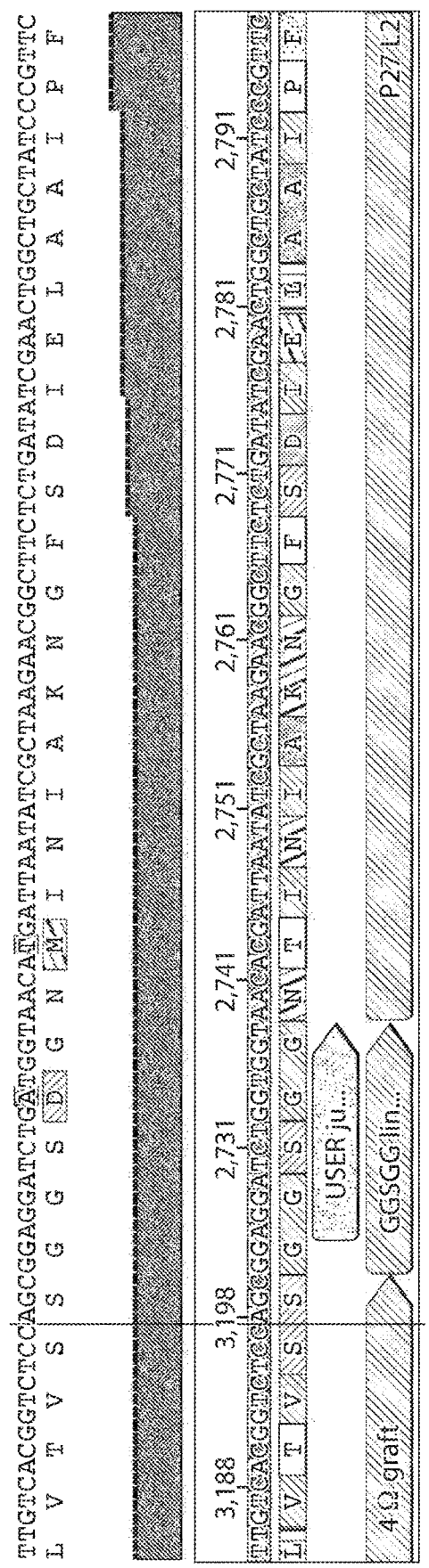
FIG. 36 shows a schematic overview of Ωgraft scFv variants cheating to evolve a secondary translational start site (M) in the L2 lagoon. SEQ ID NOs: 12-16 are shown, top to bottom.

It was observed that L2 cheated by evolving a secondary translational start site (FIG. 36). Taken together, these results indicate that passing the selection by improving T7n is now more difficult, and biases selection towards improvements in the POI to dominate the mutations obtained from the selection.

Figure 37:
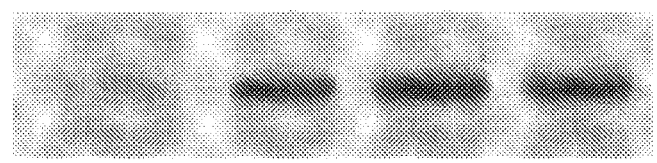
FIG. 37 shows a Western blot indicating Ωgraft scFv variants show improved soluble expression but not improved thermal stability.

The evolved variants from L1 show improved soluble expression, but not improved thermal stability. The yields from protein expression/purification are also increased (0.9 and 1.6 mg/250 mL culture for 29.2 and 29.5, respectively, compared to 0.3 mg for Ωgraft and 0.6 mg for m3), as shown in FIG. 37.

Example 11

Evolution of Anti-htt scFv C4

Figure 38A:
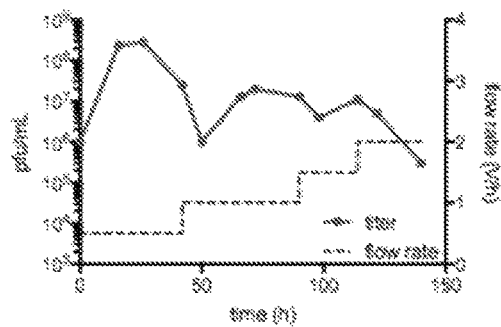
FIGS. 38A-38C show PACE of an anti-huntingtin (Htt) scFv C4.
Figure 38B:
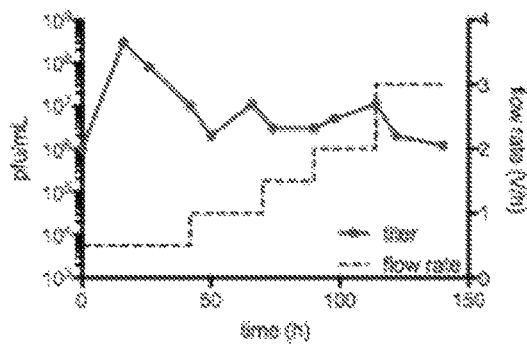
Figure 38C:
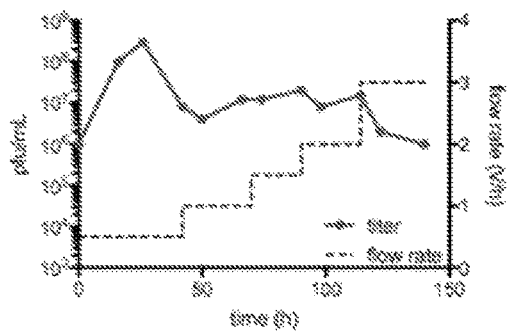

This example describes PACE of a scFv targeting the first 17 amino acids of huntingtin exon 1 (clone C4) to improve its soluble expression in *E. coli* cytosol. A previous computationally-driven attempt at engineering C4 proved unsuccessful and resulted in a more aggregation-prone scFv. Representative data from three PACE experiments are shown in FIGS. 38A-38C. Mutations arising from the PACE experiments are shown in Table 15. Evolved clones show improved soluble expression, as shown in FIG. 39.

which may be desirable when activity-based selections are not available for the protein of interest. Activity-independent solubilization was achieved through use of a GCN4 tagging strategy. Fusion of the leucine zipper domain of the yeast GCN4 transcription factor ("GCN4 tag") upstream of the protein of interest and running dual PACE selections with an protein binding AP encoding the anti-GCN4 scFv m3, which recognizes the GCN4 tag, circumvents the cheating in the same way as an activity-dependent selection. This greatly expands the scope of proteins compatible with the selection. A schematic overview of a GCN4 tagging SP is shown in FIG. 40. A PACE experiment with semi-soluble MBP G32D/I33S was performed and reversion of G32G was observed (FIG. 41 and Table 16), indicating that this strategy allows evolution of proteins independent of activity.

TABLE 16

|  | malE31 |  |  | T7n evolved |
| --- | --- | --- | --- | --- |
| L2-93-1 | G24V | D32G | D33S | R172C |
| L2-93-2 |  | D32G | D33S |  |
| L2-93-3 | G24V | D32G | D33S | R172C |
| L2-93-4 | G24V | D32G | D33S |  |

In summary, PACE selection for soluble protein expression has been shown for a number of examples. This

TABLE 15

| | | | | anti-htt C4 | | | | | |
| --- | --- | --- | --- | --- | --- | --- | --- | --- | --- |
| L1-120-2 | A1V | | | V38F | | | | | |
| L1-120-3 | | | | | | A98T | G107 | G122 | |
| L1-120-4 | A1T | Q6K | | | | | | | S144L |
| L1-120-5 | | | | | | | | | |
| L2-120-1 | | | F30L | V38F | | | | S157 | |
| L2-120-2 | | | | | | A98V | | | S223A |
| L2-120-3 | | | | | | A98V | S126P | | |
| L2-120-4 | | | | V38F | | | | | |
| L4-120-3 | | | | | | | | | |
| L4-120-4 | | Q2K | | | | A98V | | | |
| L4-120-5 | | Q2K | | | | A98V | | | |
| L4-120-6 | A1T | | | V38F | | | | Y163C | |
| | | | | T7n evolved | | | | | |
| L1-120-2 | I3M | | | | | | | | |
| L1-120-3 | | | | | | | | | |
| L1-120-4 | | | | | | | | | |
| L1-120-5 | | | | | | | | | |
| L2-120-1 | | K97R | | | | | | | |
| L2-120-2 | | K97R | | | | | | | |
| L2-120-3 | | K97R | | | | | | | |
| L2-120-4 | | K97R | | | | | | | |
| L4-120-3 | | | | | | | | | |
| L4-120-4 | | | | A135T | K159E | | | | |
| L4-120-5 | E55D | T131I | | | | | | | |
| L4-120-6 | | | | | | | | | |

Example 12

Expansion of POI Scope via "GCN4 Tagging"

This example describes a "GCN4 tag" selection strategy to satisfy protein-protein binding requirement of the 2-H selection system. This strategy was developed to overcome cheaters which evolved a premature stop codon adjacent to an in-frame start codon which circumvents translation of the entire protein of interest—T7 N-terminal domain fusion, and allows the phage to make T7 N-terminal domain only. Coupling the solubility selection to an activity selection (e.g., protein binding) prevents this cheating, but also precludes activity-independent protein solubility evolution, selection improves protein expression in the *E. coli* cytosol as well as yields after protein expression/purification.

SEQUENCES

>SEQ ID NO: 1; *E. coli* sigma 32 (σ32) promoter
CGCTGATAAGGCTTGAAAAGTTCATTTCCAGACCCATTTTTACATCGTAG
CCGATGA >SEQ ID NO: 2; T7 RNAP N-terminal domain
NTINIAKNDFSDIELAAIPFNTLADHYGERLAREQLALEHESYEMGEARF
RKMFERQLKAGEVADNAAAKPLITTLLPKMIARINDWFEEVKAKRGKRPT

AFQFLQEIKPEAVAYITIKTTLACLTSADNTTVQAVASAIGRAIEDEARF
GRIRDLEAKHFKKNVEEQLNKRVGHVYK

SEQ ID NO: 3; T7 RNAP C-terminal domain
MKAFMQVVEADMLSKGLLGGEAWSSWHKEDSIHVGVRCIEMLIESTGMVS
LHRQNAGVVGQDSETIELAPEYAEAIATRAGALAGISPMFQPCVVPPKPW
TGITGGGYWANGRRPLALVRTHSKKALMRYEDVYMPEVYKAINIAQNTAW
KINKKVLAVANVITKWKHCPVEDIPAIEREELPMKPEDIDMNPEALTAWK
RAAAAVYRKDKARKSRRISLEFMLEQANKFANHKAIWFPYNMDWRGRVYA
VSMFNPQGNDMTKGLLTLAKGKPIGKEGYYWLKIHGANCAGVDKVPFPER
IKFIEENHENIMACAKSPLENTWWAEQDSPFCFLAFCFEYAGVQHHGLSY
NCSLPLAFDGSCSGIQHFSAMLRDEVGGRAVNLLPSETVQDIYGIVAKKV
NEILQADAINGTDNEVVTVTDENTGEISEKVKLGTKALAGQWLAYGVTRS
VTKRSVMTLAYGSKEFGFRQQVLEDTIQPAIDSGKGLMFTQPNQAAGYMA
KLIWESVSVTVVAAVEAMNWLKSAAKLLAAEVKDKKTGEILRKRCAVHWV
TPDGFPVWQEYKKPIQTRLNLMFLGQFRLQPTINTNKDSEIDAHKQESGI
APNFVHSQDGSHLRKTVVWAHEKYGIESFALIHDSFGTIPADAANLFKAV
RETMVDTYESCDVLADFYDQFADQLHESQLDKMPALPAKGNLNLRDILES
DFAFA >SEQ ID NO: 4; NpuC-SP11-18-g3p
MIKIATRKYLGKQNVYDIGVERDHNFALKNGFIASNCFNVVPFYSHSAET
VESCLAKPHTENSFTNVWKDDKTLDRYANYEGCLWNATGVVVCTGDETQC
YGTWVPIGLAIPENEGGGSEGGGSEGGGSEGGGTKPPEYGDTPIPGYTYI
NPLDGTYPPGTEQNPANPNPSLEESQPLNTFMFQNNRFRNRQGALTVYTG
TVTQGTDPVKTYYQYTPVSSKAMYDAYWNGKFRDCAFHSGFNEDPFVCEY
QGQSSDLPQPPVNAGGGSGGGSGGGSEGGGSEGGGSEGGGSEGGGSGGGS
GSGDFDYEKMANANKGAMTENADENALQSDAKGKLDSVATDYGAAIDGFI
GDVSGLANGNGATGDFAGSNSQMAQVGDGDNSPLMNNFRQYLPSLPQSVE
CRPFVFGAGKPYEFSIDCDKINLFRGVFAFLLYVATFMYVFSTFANILRN
KES >SEQ ID NO: 5; SP1-10-NpuN
MKKLLFAIPLCLSYETEILTVEYGLLPIGKIVEKRIECTVYSVDNNGNIY
TQPVAQWHDRGEQEVFEYCLEDGSLIRATKDHKFMTVDGQMLPIDEIFER
ELDLMRVDNLPN >SEQ ID NO: 6; ibpA-T7 RNAP N-term fusion
MRNFDLSPLYRSAIGFDRLFNHLENNQSQSNGGYPPYNVELVDENHYRIA
IAVAGFAESELEITAQDNLLVVKGAHADEQKERTYLYQGIAERNFERKFQ
LAENIHVRGANLVNGLLYIDLERVIPEAKKPRRIEINGGSSGGNTINIAKN
DFSDIELAAIPFNTLADHYGERLAREQLALEHESYEMGEARFRKMFERQL
KAGEVADNAAAKPLITTLLPKMIARINDWFEEVKAKRGKRPTAFQFLQEI
KPEAVAYITIKTTLACLTSADNTTVQAVASAIGRAIEDEARFGRIRDLEA
KHFKKNVEEQLNKRVGHVYK >SEQ ID NO: 7; ibpB T7 RNAP N-term fusion
MRNFDLSPLMRQWIGFDKLANALQNAGESQSFPPYNIEKSDDNHYRITLA
LAGFRQEDLEIQLEGTRLSVKGTPEQPKEEKKWLHQGLMNQPFSLSFTLA
ENMEVSGATFVNGLLHIDLIRNEPEPIAAQRIAISERPALNSGGSGGNTI
NIAKNDFSDIELAAIPFNTLADHYGERLAREQLALEHESYEMGEARFRKM
FERQLKAGEVADNAAAKPLITTLLPKMIARINDWFEEVKAKRGKRPTAFQ
FLQEIKPEAVAYITIKTTLACLTSADNTTVQAVASAIGRAIEDEARFGRI
RDLEAKHFKKNVEEQLNKRVGHVYK >SEQ ID NO: 8; pIII signal peptide residues
1-10
MKKLLPAIP >SEQ ID NO: 9; pIII protein lacking SP residues
1-10
VVPFYSHSAETVESCLAKPHTENSFTNVWKDDKTLDRYANYEGCLWNATG
VVVCTGDETQCYGTWVPIGLAIPENEGGGSEGGGSEGGGSEGGGTKPPEY
GDTPIPGYTYINPLDGTYPPGTEQNPANPNPSLEESQPLNTFMFQNNRFR
NRQGALTVYTGTVTQGTDPVKTYYQYTPVSSKAMYDAYWNGKFRDCAFHS
GFNEDPFVCEYQGQSSDLPQPPVNAGGGSGGGSGGGSEGGGSEGGGSEGG
GSEGGGSGGGSGSGDFDYEKMANANKGAMTENADENALQSDAKGKLDSVA
TDYGAAIDGFIGDVSGLANGNGATGDFAGSNSQMAQVGDGDNSPLMNNFR
QYLPSLPQSVECRPFVFGAGKPYEFSIDCDKINLFRGVFAFLLYVATFMY
VFSTFANILRNKES >SEQ ID NO: 10; Voigt RNAP Sequence
NTINIAKNDFSDIELAAIPFNTLADHYGERLAREQLALEHESYEMGEARF
RKMFERQLKAGEVADN >SEQ ID NO: 11 GCN4 tag sequence
MQRMKQLEPKVEELLPKNYHLENEVARLKKLVGER

What is claimed is:

1. A method of phage-assisted continuous evolution (PACE), comprising
   (a) contacting a population of bacterial host cells with a population of M13 phages comprising a gene of interest to be evolved fused to a T7 RNAP and a RNAP omega subunit (rpoZ),
   wherein the M13 phages are deficient in a full-length pIII gene,
   wherein
      (1) the phage allows for expression of the gene of interest in the host cells,
      (2) the host cells are suitable host cells for M13 phage infection, replication, and packaging; and
      (3) the host cells comprise a first expression construct encoding a nucleic acid, comprising a split intein, wherein expression of the pIII gene is dependent on trans-splicing of the split intein N- and C-terminal portions;
   (b) incubating the population of host cells under conditions allowing for the mutation of the gene of interest, the production of infectious M13 phage, and the infection of host cells with M13 phage, wherein infected cells are removed from the population of host cells, and wherein the population of host cells is replenished with fresh host cells that are not infected by M13 phage; and
   (c) isolating a mutated M13 phage replication product encoding an evolved protein from the population of host cells.

2. The method of claim 1, wherein the evolved protein encoded by the replication product isolated in step (c) has increased solubility and/or stability relative to the gene product of the gene to be evolved.

3. The method of claim 1, wherein the split intein is a Nostoc punctiforme (Npu) split intein.

4. The method of claim 3, wherein the nucleic acid comprises a sequence encoding a promoter operably linked to an expression cassette comprising, in the following order:
   (i) a sequence encoding the Npu split intein C-terminal portion; and
   (ii) a sequence encoding a M13 phage gIII protein;
   wherein the sequence encoding the gIII protein lacks one or more nucleic acid bases in its signal peptide domain.

5. The method of claim 4, wherein the promoter is a T7 promoter.

6. The method of claim 4, wherein the sequence encoding the gIII protein lacks nucleic acid bases 1-10 of the signal peptide domain.

7. The method of claim 4, wherein the nucleic acid comprises a sequence encoding a protein as set forth in SEQ ID NO: 4.

8. The method of claim 4, wherein the host cells further comprise a second expression construct comprising a sequence encoding a portion of the gIII protein fused to a sequence encoding the Npu split intein N-terminal portion.

9. The method of claim 8, wherein the sequence encoding the portion of the gIII protein comprises nucleic acid bases 1-10 of the signal peptide domain.

10. The method of claim 8, wherein the second expression construct comprises a sequence encoding a protein as set forth in SEQ ID NO: 5.

11. The method of claim 8, wherein the first expression construct or the second expression construct further comprises a nucleic acid encoding a phage repressor protein.

12. The method of claim 1, wherein the bacterial host cells are E. coli cells.

13. The method of claim 12, wherein the E. coli cells are cells of the genotype F'proA+B+Δ(lacIZY) zzf::Tn10(TetR)/ endA1 recA1 galE15 galK16 nupG rpsL ΔlacIZYA araD139 Δ(ara,leu)7697 mcrA Δ(mrr-hsdRMS-mcrBC) proBA:: pir116 λ.

14. The method of claim 1, wherein the host cells further comprise a mutagenesis plasmid.

15. The method of claim 1, wherein gene of interest is a monobody.

16. The method of claim 1, wherein gene of interest is a single-chain variable fragment (scFv).

17. The method of claim 1, wherein gene of interest is a Cry1Ac.

18. The method of claim 1, wherein gene of interest is a maltose binding protein (MBP).

19. The method of claim 1, wherein the method further comprises a negative selection for undesired activity of the gene to be evolved.

20. The method of claim 19, wherein the host cells comprise an expression construct encoding a dominant-negative pIII protein, wherein expression of the dominant-negative pIII protein is driven by a promoter, the activity of which depends on an undesired function of the gene of interest.

* * * * *

UNITED STATES PATENT AND TRADEMARK OFFICE
CERTIFICATE OF CORRECTION

| | | Page 1 of 1 |
|---|---|---|
| PATENT NO. | : 11,624,130 B2 | |
| APPLICATION NO. | : 16/648162 | |
| DATED | : April 11, 2023 | |
| INVENTOR(S) | : David R. Liu et al. | |

It is certified that error appears in the above-identified patent and that said Letters Patent is hereby corrected as shown below:

In the Claims

In Claim 1, at Column 59, Line 45, the text: "encoding a nucleic acid, comprising a split intein," should be replaced with: -- encoding a nucleic acid comprising a split intein, --.

In Claim 13, at Column 60, Lines 59-63, the text: "The method of claim 12, wherein the E. coli cells are cells of the genotype F′proA+B+Δ(lacIZY) zzf::Tnl10(TetR)/endA1 recA1 galEl15 galK16 nupG rpsL ΔlacIZYA araD139 Δ (ara,leu)7697 mcrA Δ(mrr-hsdRMS-mcrBC) proBA:: pir116 λ." should be replaced with: -- The method of claim 12, wherein the *E. coli* cells are cells of the genotype F′proA+B+ Δ(lacIZY) zzf::Tn10(TetR)/ endA1 recA1 galE15 galK16 nupG rpsL ΔlacIZYA araD139 Δ(ara,leu)7697 mcrA Δ(mrr-hsdRMS-mcrBC) proBA::pir116 λ-. --.

Signed and Sealed this
Fifth Day of September, 2023

Katherine Kelly Vidal
*Director of the United States Patent and Trademark Office*

SEQUENCE LISTING

<160> NUMBER OF SEQ ID NOS: 16

<210> SEQ ID NO 1
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 1
cgctgataag gcttgaaaag ttcatttcca gacccatttt tacatcgtag ccgatga        57

<210> SEQ ID NO 2
<211> LENGTH: 178
<212> TYPE: PRT
<213> ORGANISM: Artificial Sequence
<220> FEATURE:
<223> OTHER INFORMATION: Synthetic Polypeptide

<400> SEQUENCE: 2

Asn Thr Ile Asn Ile Ala Lys Asn Asp Phe Ser Asp Ile Glu Leu Ala
1               5                   10                  15

Ala Ile Pro Phe Asn Thr Leu Ala Asp His Tyr Gly Glu Arg Leu Ala
            20                  25                  30

```
Arg Glu Gln Leu Ala Leu Glu His Glu Ser Tyr Glu Met Gly Glu Ala
         35                  40                  45

Arg Phe Arg Lys Met Phe Glu Arg Gln Leu Lys Ala Gly Glu Val Ala
 50                  55                  60

Asp Asn Ala Ala Ala Lys Pro Leu Ile Thr Thr Leu Leu Pro Lys Met
 65                  70                  75                  80

Ile Ala Arg Ile Asn Asp Trp Phe Glu Val Lys Ala Lys Arg Gly
                 85                  90                  95

Lys Arg Pro Thr Ala Phe Gln Phe Leu Gln Glu Ile Lys Pro Glu Ala
             100                 105                 110

Val Ala Tyr Ile Thr Ile Lys Thr Thr Leu Ala Cys Leu Thr Ser Ala
             115                 120                 125

Asp Asn Thr Thr Val Gln Ala Val Ala Ser Ala Ile Gly Arg Ala Ile
             130                 135                 140

Glu Asp Glu Ala Arg Phe Gly Arg Ile Arg Asp Leu Glu Ala Lys His
145                 150                 155                 160

Phe Lys Lys Asn Val Glu Glu Gln Leu Asn Lys Arg Val Gly His Val
                 165                 170                 175

Tyr Lys

<210> SEQ ID NO 3
<211> LENGTH: 705
<212> TYPE: PRT
<213> ORGANISM: Artificial Sequence
<220> FEATURE:
<223> OTHER INFORMATION: Synthetic Polypeptide

<400> SEQUENCE: 3

Met Lys Ala Phe Met Gln Val Val Glu Ala Asp Met Leu Ser Lys Gly
 1               5                  10                  15

Leu Leu Gly Gly Glu Ala Trp Ser Ser Trp His Lys Glu Asp Ser Ile
             20                  25                  30

His Val Gly Val Arg Cys Ile Glu Met Leu Ile Glu Ser Thr Gly Met
             35                  40                  45

Val Ser Leu His Arg Gln Asn Ala Gly Val Val Gly Gln Asp Ser Glu
 50                  55                  60

Thr Ile Glu Leu Ala Pro Glu Tyr Ala Glu Ile Ala Thr Arg Ala
 65                  70                  75                  80

Gly Ala Leu Ala Gly Ile Ser Pro Met Phe Gln Pro Cys Val Val Pro
             85                  90                  95

Pro Lys Pro Trp Thr Gly Ile Thr Gly Gly Tyr Trp Ala Asn Gly
             100                 105                 110

Arg Arg Pro Leu Ala Leu Val Arg Thr His Ser Lys Lys Ala Leu Met
             115                 120                 125

Arg Tyr Glu Asp Val Tyr Met Pro Glu Val Tyr Lys Ala Ile Asn Ile
             130                 135                 140

Ala Gln Asn Thr Ala Trp Lys Ile Asn Lys Lys Val Leu Ala Val Ala
145                 150                 155                 160

Asn Val Ile Thr Lys Trp Lys His Cys Pro Val Glu Asp Ile Pro Ala
                 165                 170                 175

Ile Glu Arg Glu Glu Leu Pro Met Lys Pro Glu Asp Ile Asp Met Asn
                 180                 185                 190

Pro Glu Ala Leu Thr Ala Trp Lys Arg Ala Ala Ala Val Tyr Arg
             195                 200                 205

Lys Asp Lys Ala Arg Lys Ser Arg Arg Ile Ser Leu Glu Phe Met Leu
```

-continued

```
            210                 215                 220
Glu Gln Ala Asn Lys Phe Ala Asn His Lys Ala Ile Trp Phe Pro Tyr
225                 230                 235                 240

Asn Met Asp Trp Arg Gly Arg Val Tyr Ala Val Ser Met Phe Asn Pro
                    245                 250                 255

Gln Gly Asn Asp Met Thr Lys Gly Leu Leu Thr Leu Ala Lys Gly Lys
                260                 265                 270

Pro Ile Gly Lys Glu Gly Tyr Tyr Trp Leu Lys Ile His Gly Ala Asn
            275                 280                 285

Cys Ala Gly Val Asp Lys Val Pro Phe Pro Glu Arg Ile Lys Phe Ile
        290                 295                 300

Glu Glu Asn His Glu Asn Ile Met Ala Cys Ala Lys Ser Pro Leu Glu
305                 310                 315                 320

Asn Thr Trp Trp Ala Glu Gln Asp Ser Pro Phe Cys Phe Leu Ala Phe
                    325                 330                 335

Cys Phe Glu Tyr Ala Gly Val Gln His His Gly Leu Ser Tyr Asn Cys
                340                 345                 350

Ser Leu Pro Leu Ala Phe Asp Gly Ser Cys Ser Gly Ile Gln His Phe
            355                 360                 365

Ser Ala Met Leu Arg Asp Glu Val Gly Gly Arg Ala Val Asn Leu Leu
        370                 375                 380

Pro Ser Glu Thr Val Gln Asp Ile Tyr Gly Ile Val Ala Lys Lys Val
385                 390                 395                 400

Asn Glu Ile Leu Gln Ala Asp Ala Ile Asn Gly Thr Asp Asn Glu Val
                    405                 410                 415

Val Thr Val Thr Asp Glu Asn Thr Gly Glu Ile Ser Glu Lys Val Lys
                420                 425                 430

Leu Gly Thr Lys Ala Leu Ala Gly Gln Trp Leu Ala Tyr Gly Val Thr
            435                 440                 445

Arg Ser Val Thr Lys Arg Ser Val Met Thr Leu Ala Tyr Gly Ser Lys
        450                 455                 460

Glu Phe Gly Phe Arg Gln Gln Val Leu Glu Asp Thr Ile Gln Pro Ala
465                 470                 475                 480

Ile Asp Ser Gly Lys Gly Leu Met Phe Thr Gln Pro Asn Gln Ala Ala
                    485                 490                 495

Gly Tyr Met Ala Lys Leu Ile Trp Glu Ser Val Ser Val Thr Val Val
                500                 505                 510

Ala Ala Val Glu Ala Met Asn Trp Leu Lys Ser Ala Ala Lys Leu Leu
            515                 520                 525

Ala Ala Glu Val Lys Asp Lys Lys Thr Gly Glu Ile Leu Arg Lys Arg
        530                 535                 540

Cys Ala Val His Trp Val Thr Pro Asp Gly Phe Pro Val Trp Gln Glu
545                 550                 555                 560

Tyr Lys Lys Pro Ile Gln Thr Arg Leu Asn Leu Met Phe Leu Gly Gln
                    565                 570                 575

Phe Arg Leu Gln Pro Thr Ile Asn Thr Asn Lys Asp Ser Glu Ile Asp
                580                 585                 590

Ala His Lys Gln Glu Ser Gly Ile Ala Pro Asn Phe Val His Ser Gln
            595                 600                 605

Asp Gly Ser His Leu Arg Lys Thr Val Val Trp Ala His Glu Lys Tyr
        610                 615                 620

Gly Ile Glu Ser Phe Ala Leu Ile His Asp Ser Phe Gly Thr Ile Pro
625                 630                 635                 640
```

```
Ala Asp Ala Ala Asn Leu Phe Lys Ala Val Arg Glu Thr Met Val Asp
            645                 650                 655

Thr Tyr Glu Ser Cys Asp Val Leu Ala Asp Phe Tyr Asp Gln Phe Ala
        660                 665                 670

Asp Gln Leu His Glu Ser Gln Leu Asp Lys Met Pro Ala Leu Pro Ala
    675                 680                 685

Lys Gly Asn Leu Asn Leu Arg Asp Ile Leu Glu Ser Asp Phe Ala Phe
690                 695                 700

Ala
705

<210> SEQ ID NO 4
<211> LENGTH: 453
<212> TYPE: PRT
<213> ORGANISM: Artificial Sequence
<220> FEATURE:
<223> OTHER INFORMATION: Synthetic Polypeptide

<400> SEQUENCE: 4

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Phe Asn Val Val Pro Tyr Ser His Ser Ala
        35                  40                  45

Glu Thr Val Glu Ser Cys Leu Ala Lys Pro His Thr Glu Asn Ser Phe
    50                  55                  60

Thr Asn Val Trp Lys Asp Asp Lys Thr Leu Asp Arg Tyr Ala Asn Tyr
65                  70                  75                  80

Glu Gly Cys Leu Trp Asn Ala Thr Gly Val Val Cys Thr Gly Asp
            85                  90                  95

Glu Thr Gln Cys Tyr Gly Thr Trp Val Pro Ile Gly Leu Ala Ile Pro
        100                 105                 110

Glu Asn Glu Gly Gly Gly Ser Glu Gly Gly Gly Ser Glu Gly Gly Gly
    115                 120                 125

Ser Glu Gly Gly Gly Thr Lys Pro Pro Glu Tyr Gly Asp Thr Pro Ile
130                 135                 140

Pro Gly Tyr Thr Tyr Ile Asn Pro Leu Asp Gly Thr Tyr Pro Pro Gly
145                 150                 155                 160

Thr Glu Gln Asn Pro Ala Asn Pro Asn Pro Ser Leu Glu Glu Ser Gln
            165                 170                 175

Pro Leu Asn Thr Phe Met Phe Gln Asn Asn Arg Phe Arg Asn Arg Gln
        180                 185                 190

Gly Ala Leu Thr Val Tyr Thr Gly Thr Val Thr Gln Gly Thr Asp Pro
    195                 200                 205

Val Lys Thr Tyr Tyr Gln Tyr Thr Pro Val Ser Ser Lys Ala Met Tyr
210                 215                 220

Asp Ala Tyr Trp Asn Gly Lys Phe Arg Asp Cys Ala Phe His Ser Gly
225                 230                 235                 240

Phe Asn Glu Asp Pro Phe Val Cys Glu Tyr Gln Gly Gln Ser Ser Asp
            245                 250                 255

Leu Pro Gln Pro Pro Val Asn Ala Gly Gly Gly Ser Gly Gly Gly Ser
        260                 265                 270

Gly Gly Gly Ser Glu Gly Gly Gly Ser Glu Gly Gly Gly Ser Glu Gly
    275                 280                 285
```

```
Gly Gly Ser Glu Gly Gly Ser Gly Gly Ser Gly Ser Gly Asp
        290                 295                 300

Phe Asp Tyr Glu Lys Met Ala Asn Ala Asn Lys Gly Ala Met Thr Glu
305                 310                 315                 320

Asn Ala Asp Glu Asn Ala Leu Gln Ser Asp Ala Lys Gly Lys Leu Asp
                325                 330                 335

Ser Val Ala Thr Asp Tyr Gly Ala Ala Ile Asp Gly Phe Ile Gly Asp
                340                 345                 350

Val Ser Gly Leu Ala Asn Gly Asn Gly Ala Thr Gly Asp Phe Ala Gly
                355                 360                 365

Ser Asn Ser Gln Met Ala Gln Val Gly Asp Gly Asp Asn Ser Pro Leu
        370                 375                 380

Met Asn Asn Phe Arg Gln Tyr Leu Pro Ser Leu Pro Gln Ser Val Glu
385                 390                 395                 400

Cys Arg Pro Phe Val Phe Gly Ala Gly Lys Pro Tyr Glu Phe Ser Ile
                405                 410                 415

Asp Cys Asp Lys Ile Asn Leu Phe Arg Gly Val Phe Ala Phe Leu Leu
                420                 425                 430

Tyr Val Ala Thr Phe Met Tyr Val Phe Ser Thr Phe Ala Asn Ile Leu
                435                 440                 445

Arg Asn Lys Glu Ser
    450

<210> SEQ ID NO 5
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 5

Met Lys Lys Leu Leu Phe Ala Ile Pro Leu Cys Leu Ser Tyr Glu Thr
1               5                   10                  15

Glu Ile Leu Thr Val Glu Tyr Gly Leu Leu Pro Ile Gly Lys Ile Val
                20                  25                  30

Glu Lys Arg Ile Glu Cys Thr Val Tyr Ser Val Asp Asn Asn Gly Asn
            35                  40                  45

Ile Tyr Thr Gln Pro Val Ala Gln Trp His Asp Arg Gly Glu Gln Glu
        50                  55                  60

Val Phe Glu Tyr Cys Leu Glu Asp Gly Ser Leu Ile Arg Ala Thr Lys
65                  70                  75                  80

Asp His Lys Phe Met Thr Val Asp Gly Gln Met Leu Pro Ile Asp Glu
                85                  90                  95

Ile Phe Glu Arg Glu Leu Asp Leu Met Arg Val Asp Asn Leu Pro Asn
                100                 105                 110

<210> SEQ ID NO 6
<211> LENGTH: 320
<212> TYPE: PRT
<213> ORGANISM: Artificial Sequence
<220> FEATURE:
<223> OTHER INFORMATION: Synthetic Polypeptide

<400> SEQUENCE: 6

Met Arg Asn Phe Asp Leu Ser Pro Leu Tyr Arg Ser Ala Ile Gly Phe
1               5                   10                  15

Asp Arg Leu Phe Asn His Leu Glu Asn Asn Gln Ser Gln Ser Asn Gly
```

```
            20                  25                  30
Gly Tyr Pro Tyr Asn Val Glu Leu Val Asp Glu Asn His Tyr Arg
        35                  40                  45

Ile Ala Ile Ala Val Ala Gly Phe Ala Glu Ser Glu Leu Glu Ile Thr
 50                  55                  60

Ala Gln Asp Asn Leu Leu Val Val Lys Gly Ala His Ala Asp Glu Gln
 65                  70                  75                  80

Lys Glu Arg Thr Tyr Leu Tyr Gln Gly Ile Ala Glu Arg Asn Phe Glu
                 85                  90                  95

Arg Lys Phe Gln Leu Ala Glu Asn Ile His Val Arg Gly Ala Asn Leu
            100                 105                 110

Val Asn Gly Leu Leu Tyr Ile Asp Leu Glu Arg Val Ile Pro Glu Ala
            115                 120                 125

Lys Lys Pro Arg Arg Ile Glu Ile Asn Gly Gly Ser Gly Gly Asn Thr
130                 135                 140

Ile Asn Ile Ala Lys Asn Asp Phe Ser Asp Ile Glu Leu Ala Ala Ile
145                 150                 155                 160

Pro Phe Asn Thr Leu Ala Asp His Tyr Gly Glu Arg Leu Ala Arg Glu
                165                 170                 175

Gln Leu Ala Leu Glu His Glu Ser Tyr Glu Met Gly Glu Ala Arg Phe
            180                 185                 190

Arg Lys Met Phe Glu Arg Gln Leu Lys Ala Gly Glu Val Ala Asp Asn
            195                 200                 205

Ala Ala Ala Lys Pro Leu Ile Thr Thr Leu Leu Pro Lys Met Ile Ala
            210                 215                 220

Arg Ile Asn Asp Trp Phe Glu Glu Val Lys Ala Lys Arg Gly Lys Arg
225                 230                 235                 240

Pro Thr Ala Phe Gln Phe Leu Gln Glu Ile Lys Pro Glu Ala Val Ala
                245                 250                 255

Tyr Ile Thr Ile Lys Thr Thr Leu Ala Cys Leu Thr Ser Ala Asp Asn
            260                 265                 270

Thr Thr Val Gln Ala Val Ala Ser Ala Ile Gly Arg Ala Ile Glu Asp
            275                 280                 285

Glu Ala Arg Phe Gly Arg Ile Arg Asp Leu Glu Ala Lys His Phe Lys
            290                 295                 300

Lys Asn Val Glu Glu Gln Leu Asn Lys Arg Val Gly His Val Tyr Lys
305                 310                 315                 320

<210> SEQ ID NO 7
<211> LENGTH: 325
<212> TYPE: PRT
<213> ORGANISM: Artificial Sequence
<220> FEATURE:
<223> OTHER INFORMATION: Synthetic Polypeptide

<400> SEQUENCE: 7

Met Arg Asn Phe Asp Leu Ser Pro Leu Met Arg Gln Trp Ile Gly Phe
 1               5                  10                  15

Asp Lys Leu Ala Asn Ala Leu Gln Asn Ala Gly Glu Ser Gln Ser Phe
            20                  25                  30

Pro Pro Tyr Asn Ile Glu Lys Ser Asp Asp Asn His Tyr Arg Ile Thr
            35                  40                  45

Leu Ala Leu Ala Gly Phe Arg Gln Glu Asp Leu Glu Ile Gln Leu Glu
 50                  55                  60

Gly Thr Arg Leu Ser Val Lys Gly Thr Pro Glu Gln Pro Lys Glu Glu
```

```
                65                  70                  75                  80
Lys Lys Trp Leu His Gln Gly Leu Met Asn Gln Pro Phe Ser Leu Ser
                85                  90                  95

Phe Thr Leu Ala Glu Asn Met Glu Val Ser Gly Ala Thr Phe Val Asn
            100                 105                 110

Gly Leu Leu His Ile Asp Leu Ile Arg Asn Glu Pro Glu Pro Ile Ala
        115                 120                 125

Ala Gln Arg Ile Ala Ile Ser Glu Arg Pro Ala Leu Asn Ser Gly Gly
    130                 135                 140

Ser Gly Gly Asn Thr Ile Asn Ile Ala Lys Asn Asp Phe Ser Asp Ile
145                 150                 155                 160

Glu Leu Ala Ala Ile Pro Phe Asn Thr Leu Ala Asp His Tyr Gly Glu
                165                 170                 175

Arg Leu Ala Arg Glu Gln Leu Ala Leu Glu His Glu Ser Tyr Glu Met
            180                 185                 190

Gly Glu Ala Arg Phe Arg Lys Met Phe Glu Arg Gln Leu Lys Ala Gly
        195                 200                 205

Glu Val Ala Asp Asn Ala Ala Ala Lys Pro Leu Ile Thr Thr Leu Leu
    210                 215                 220

Pro Lys Met Ile Ala Arg Ile Asn Asp Trp Phe Glu Glu Val Lys Ala
225                 230                 235                 240

Lys Arg Gly Lys Arg Pro Thr Ala Phe Gln Phe Leu Gln Glu Ile Lys
                245                 250                 255

Pro Glu Ala Val Ala Tyr Ile Thr Ile Lys Thr Thr Leu Ala Cys Leu
            260                 265                 270

Thr Ser Ala Asp Asn Thr Thr Val Gln Ala Val Ala Ser Ala Ile Gly
        275                 280                 285

Arg Ala Ile Glu Asp Glu Ala Arg Phe Gly Arg Ile Arg Asp Leu Glu
    290                 295                 300

Ala Lys His Phe Lys Lys Asn Val Glu Glu Gln Leu Asn Lys Arg Val
305                 310                 315                 320

Gly His Val Tyr Lys
                325

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 8

Met Lys Lys Leu Leu Pro Ala Ile Pro
1               5

<210> SEQ ID NO 9
<211> LENGTH: 414
<212> TYPE: PRT
<213> ORGANISM: Artificial Sequence
<220> FEATURE:
<223> OTHER INFORMATION: Synthetic Polypeptide

<400> SEQUENCE: 9

Val Val Pro Phe Tyr Ser His Ser Ala Glu Thr Val Glu Ser Cys Leu
1               5                   10                  15

Ala Lys Pro His Thr Glu Asn Ser Phe Thr Asn Val Trp Lys Asp Asp
            20                  25                  30
```

Lys Thr Leu Asp Arg Tyr Ala Asn Tyr Glu Gly Cys Leu Trp Asn Ala
            35                  40                  45

Thr Gly Val Val Val Cys Thr Gly Asp Glu Thr Gln Cys Tyr Gly Thr
 50                  55                  60

Trp Val Pro Ile Gly Leu Ala Ile Pro Glu Asn Glu Gly Gly Gly Ser
 65                  70                  75                  80

Glu Gly Gly Gly Ser Glu Gly Gly Ser Glu Gly Gly Thr Lys
                85                  90                  95

Pro Pro Glu Tyr Gly Asp Thr Pro Ile Pro Gly Tyr Thr Tyr Ile Asn
            100                 105                 110

Pro Leu Asp Gly Thr Tyr Pro Pro Gly Thr Glu Gln Asn Pro Ala Asn
            115                 120                 125

Pro Asn Pro Ser Leu Glu Glu Ser Gln Pro Leu Asn Thr Phe Met Phe
130                 135                 140

Gln Asn Asn Arg Phe Arg Asn Arg Gln Gly Ala Leu Thr Val Tyr Thr
145                 150                 155                 160

Gly Thr Val Thr Gln Gly Thr Asp Pro Val Lys Thr Tyr Tyr Gln Tyr
            165                 170                 175

Thr Pro Val Ser Ser Lys Ala Met Tyr Asp Ala Tyr Trp Asn Gly Lys
            180                 185                 190

Phe Arg Asp Cys Ala Phe His Ser Gly Phe Asn Glu Asp Pro Phe Val
            195                 200                 205

Cys Glu Tyr Gln Gly Gln Ser Ser Asp Leu Pro Gln Pro Pro Val Asn
            210                 215                 220

Ala Gly Gly Gly Ser Gly Gly Ser Gly Gly Ser Glu Gly Gly
225                 230                 235                 240

Gly Ser Glu Gly Gly Ser Glu Gly Gly Ser Glu Gly Gly
            245                 250                 255

Ser Gly Gly Ser Gly Ser Gly Asp Phe Asp Tyr Glu Lys Met Ala
            260                 265                 270

Asn Ala Asn Lys Gly Ala Met Thr Glu Asn Ala Asp Glu Asn Ala Leu
            275                 280                 285

Gln Ser Asp Ala Lys Gly Lys Leu Asp Ser Val Ala Thr Asp Tyr Gly
290                 295                 300

Ala Ala Ile Asp Gly Phe Ile Gly Asp Val Ser Gly Leu Ala Asn Gly
305                 310                 315                 320

Asn Gly Ala Thr Gly Asp Phe Ala Gly Ser Asn Ser Gln Met Ala Gln
            325                 330                 335

Val Gly Asp Gly Asp Asn Ser Pro Leu Met Asn Asn Phe Arg Gln Tyr
            340                 345                 350

Leu Pro Ser Leu Pro Gln Ser Val Glu Cys Arg Pro Phe Val Phe Gly
            355                 360                 365

Ala Gly Lys Pro Tyr Glu Phe Ser Ile Asp Cys Asp Lys Ile Asn Leu
370                 375                 380

Phe Arg Gly Val Phe Ala Phe Leu Leu Tyr Val Ala Thr Phe Met Tyr
385                 390                 395                 400

Val Phe Ser Thr Phe Ala Asn Ile Leu Arg Asn Lys Glu Ser
                405                 410

<210> SEQ ID NO 10
<211> LENGTH: 66
<212> TYPE: PRT
<213> ORGANISM: Artificial Sequence
<220> FEATURE:
<223> OTHER INFORMATION: Synthetic Polypeptide

<400> SEQUENCE: 10

Asn Thr Ile Asn Ile Ala Lys Asn Asp Phe Ser Asp Ile Glu Leu Ala
1               5                   10                  15

Ala Ile Pro Phe Asn Thr Leu Ala Asp His Tyr Gly Glu Arg Leu Ala
            20                  25                  30

Arg Glu Gln Leu Ala Leu Glu His Glu Ser Tyr Glu Met Gly Glu Ala
        35                  40                  45

Arg Phe Arg Lys Met Phe Glu Arg Gln Leu Lys Ala Gly Glu Val Ala
    50                  55                  60

Asp Asn
65

<210> SEQ ID NO 11
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 11

Met Gln Arg Met Lys Gln Leu Glu Pro Lys Val Glu Glu Leu Leu Pro
1               5                   10                  15

Lys Asn Tyr His Leu Glu Asn Glu Val Ala Arg Leu Lys Lys Leu Val
            20                  25                  30

Gly Glu Arg
        35

<210> SEQ ID NO 12
<211> LENGTH: 92
<212> TYPE: DNA
<213> ORGANISM: Artificial Sequence
<220> FEATURE:
<223> OTHER INFORMATION: Synthetic Polynucleotide

<400> SEQUENCE: 12
ttgtcacggt ctccagcgga ggatctgatg gtaacatgat taatatcgct aagaacggct      60
tctctgatat cgaactggct gctatcccgt tc                                    92

<210> SEQ ID NO 13
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 13

Leu Val Thr Val Ser Ser Gly Gly Ser Asp Gly Asn Met Ile Asn Ile
1               5                   10                  15

Ala Lys Asn Gly Phe Ser Asp Ile Glu Leu Ala Ala Ile Pro Phe
            20                  25                  30

<210> SEQ ID NO 14
<211> LENGTH: 92
<212> TYPE: DNA
<213> ORGANISM: Artificial Sequence
<220> FEATURE:
<223> OTHER INFORMATION: Synthetic Polynucleotide

<400> SEQUENCE: 14
ttgtcacggt ctccagcgga ggatctggtg gtaacacgat taatatcgct aagaacggct      60

```
tctctgatat cgaactggct gctatcccgt tc                                           92

<210> SEQ ID NO 15
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 15

Leu Val Thr Val Ser Ser Gly Gly Ser Gly Gly Asn Thr Ile Asn Ile
1               5                   10                  15

Ala Lys Asn Gly Phe Ser Asp Ile Glu Leu Ala Ala Ile Pro Phe
            20                  25                  30

<210> SEQ ID NO 16
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 16

Gly Gly Ser Gly Gly
1               5
```